(12) United States Patent
Weaver et al.

(10) Patent No.: US 9,618,369 B2
(45) Date of Patent: Apr. 11, 2017

(54) USES OF ELECTROMAGNETIC INTERFERENCE PATTERNS

(75) Inventors: Jonathan Mark Ralph Weaver, Glasgow (GB); Phillip Stephen Dobson, Glasgow (GB); David Paul Burt, Glasgow (GB); Stephen Thoms, Glasgow (GB); Kevin Edward Docherty, Glasgow (GB); Yuan Zhang, Glasgow (GB)

(73) Assignee: THE UNIVERSITY COURT OF THE UNIVERSITY OF GLASGOW, Glasgow (GB)

( * ) Notice: Subject to any disclaimer, the term of this patent is extended or adjusted under 35 U.S.C. 154(b) by 361 days.

(21) Appl. No.: 13/060,033

(22) PCT Filed: Aug. 25, 2009

(86) PCT No.: PCT/GB2009/002071
§ 371 (c)(1),
(2), (4) Date: Feb. 21, 2011

(87) PCT Pub. No.: WO2010/023442
PCT Pub. Date: Mar. 4, 2010

(65) Prior Publication Data
US 2011/0157599 A1    Jun. 30, 2011

(30) Foreign Application Priority Data

Aug. 26, 2008 (GB) .................................. 0815514.5
Dec. 31, 2008 (GB) .................................. 0823707.5

(51) Int. Cl.
*G01B 11/02* (2006.01)
*G01D 5/26* (2006.01)
(Continued)

(52) U.S. Cl.
CPC ............... *G01D 5/266* (2013.01); *G01D 5/38* (2013.01); *G01D 11/00* (2013.01); *G01J 9/0246* (2013.01);
(Continued)

(58) Field of Classification Search
CPC ..... G01D 5/266; G01D 5/347–5/34792; G01J 2009/0234; G01B 11/25
(Continued)

(56) References Cited

U.S. PATENT DOCUMENTS 3,955,095 A * 5/1976 Gadbois et al. ............... 250/550
4,111,557 A   9/1978 Rottenkolber et al.
(Continued)

FOREIGN PATENT DOCUMENTS

DE   19816951   10/1999
EP   0503176    9/1992
(Continued)

OTHER PUBLICATIONS

Knight et al. (College Physics: A strategic approach), Section 17.2; Copyright 2007 Pearson Education Inc., publishing as Pearson Addison-Wesley.*
(Continued)

*Primary Examiner* — Kara E Geisel
*Assistant Examiner* — Rufus Phillips
(74) *Attorney, Agent, or Firm* — Swanson & Bratschun, L.L.C.

(57) ABSTRACT

Various uses of visible light interference patterns are provided. Suitable interference patterns are those formed by diffraction from patterns of apertures. Typical uses disclosed herein relate to spatial metrology, such as a translational and/or angular position determination system. Further uses include the analysis of properties of the light itself (such as the determination of the wavelength of the electromagnetic (Continued)

radiation). Still further uses include the analysis of one or more properties (e.g. refractive index) of the matter through which the light passes. Part of the interference pattern is captured at a pixellated detector, such as a CCD chip, and the captured pattern compared with a calculated pattern. Very precise measurements of the spacing between maxima is possible, thus allowing very precise measurements of position of the detector in the interference pattern.

14 Claims, 30 Drawing Sheets

(51) Int. Cl.
  G01D 5/38   (2006.01)
  G01D 11/00  (2006.01)
  G01J 9/02   (2006.01)
  G01N 21/45  (2006.01)
  G03H 1/00   (2006.01)

(52) U.S. Cl.
  CPC ...... *G01N 21/45* (2013.01); *G01J 2009/0234* (2013.01); *G03H 1/0005* (2013.01)

(58) Field of Classification Search
  USPC .......................... 356/454, 484, 502
  See application file for complete search history.

(56) References Cited

U.S. PATENT DOCUMENTS

| | | | | |
|---|---|---|---|---|
| 4,173,442 | A | * | 11/1979 | Snyder .......... 356/454 |
| 4,569,590 | A | | 2/1986 | Karny et al. |
| 4,794,384 | A | | 12/1988 | Jackson |
| 4,843,236 | A | | 6/1989 | Okutani |
| 5,189,485 | A | | 2/1993 | Hackel et al. |
| 5,227,862 | A | | 7/1993 | Oshida et al. |
| 5,499,098 | A | | 3/1996 | Ogawa |
| 5,748,316 | A | | 5/1998 | Wakabayashi et al. |
| 6,141,104 | A | | 10/2000 | Schulz et al. |
| 6,493,095 | B1 | | 12/2002 | Song et al. |
| 7,268,889 | B2 | * | 9/2007 | Kulawiec et al. .......... 356/511 |
| 2002/0163943 | A1 | | 11/2002 | Lano et al. |
| 2003/0076508 | A1 | | 4/2003 | Cornsweet |
| 2003/0160964 | A1 | * | 8/2003 | Dallas et al. .......... 356/496 |
| 2004/0004723 | A1 | | 1/2004 | Seko et al. |
| 2004/0061864 | A1 | | 4/2004 | Snyder et al. |
| 2004/0105100 | A1 | | 6/2004 | Shirley |
| 2004/0135209 | A1 | * | 7/2004 | Hsieh et al. .......... 257/368 |
| 2004/0174535 | A1 | | 9/2004 | Kuramoto |
| 2005/0018205 | A1 | | 1/2005 | Braasch et al. |
| 2005/0157311 | A1 | | 7/2005 | Kuchel |
| 2005/0190988 | A1 | | 9/2005 | Feron |
| 2006/0062260 | A1 | * | 3/2006 | Marron et al. .......... 372/20 |
| 2007/0008550 | A1 | | 1/2007 | Tobiason et al. |
| 2007/0229843 | A1 | | 10/2007 | Sesko |
| 2008/0035837 | A1 | | 2/2008 | Hane |

FOREIGN PATENT DOCUMENTS

| | | |
|---|---|---|
| EP | 0572144 | 12/1993 |
| EP | 0729013 | 2/1996 |
| EP | 1063503 | 12/2000 |
| EP | 1106972 | 6/2001 |
| GB | 2272759 | 5/1994 |
| JP | 10090008 | 4/1998 |
| JP | H10-111244 | 4/1998 |
| JP | 2003-194523 | 9/2003 |
| JP | 2005207856 | 8/2005 |
| JP | 2006/170899 | 6/2006 |
| JP | 2008-046037 | 2/2008 |
| WO | WO95/09343 | 4/1995 |
| WO | WO95/15480 | 6/1995 |
| WO | WO02/084223 | 10/2002 |
| WO | 03/021728 | 3/2003 |
| WO | WO03/064971 | 8/2003 |
| WO | WO2004/031686 | 4/2004 |
| WO | WO 2005/065178 | 7/2005 |
| WO | WO2006/067481 | 6/2006 |

OTHER PUBLICATIONS

International Preliminary Report on Patentability, dated Mar. 1, 2011, International application No. PCT/GB2009/002071.
International Search report dated Jul. 7, 2010 for International application No. PCT/GB2009/002071.
Partial International search report dated Feb. 22, 2010 for International application No. PCT/GB2009/002071.
International Search report dated Apr. 29, 2009 for priority application No. GB0823707.5.
Further International search report dated Jul. 20, 2009 for priority application No. GB0823707.5.
International Search report dated Dec. 23, 2008 for priority application No. GB0815514.5.
Combined International search and examination report dated Jan. 29, 2010 of related GB patent application No. GB0914852.9.
J. Hough: "Long Baseline Gravitational Wave Detectors—Status and Developments" in Journal of Physics Conference Series 012002 (2007).
N. Ferralis, A. W. Szmodis, R. D. Diehl: "Diffraction from one- and two-dimensional quasicrystalline gratings" in Am. J. Phys. 72(9) p. 1241-6 (2004).
H. Xue, R. Yang: "Optimal interpolating windowed discrete Fourier transform algorithms for harmonic analysis in power systems" in IEEE Proc. Gener. Transm. Distrib. vol. 150 No. 5 p. 583-587 (2003).
D. M. Holburn, G. A. C. Jones, H. Ahmed: "A pattern-recognition technique using sequences of marks for registration in electron-beam lithography" in Journal of Vacuum Science & Technology, 19(4), pp. 1229-1233 (1981).
L. H. Koopmans: "The Spectral Analysis of Time Series", chapter 2, No. 22 in Probability and Mathematical Statistics—A series of Monographs and Textbooks (1974), Academic Press, New York and London, pp. 33-34.
R. M. Feinberg, R. S. Hargrove: "Overview of Uranium Atomic Vapour Laser Isotope Separation", UCRL ID114-671 (1993).
T. Kurosu: "Frequency stabilization of a 1.54 μm DFB-laser diode to Doppler-free lines of acetylene", Sterr, U. Precision Electromagnetic Measurements Digest, pp. 511-512 (2000).
L. B. Lesem, P. M. Hirsch, J. A. Jordan: "The Kinoform: A new Wavefront Reconstruction Device" in Jr. IBM J. Res. Dev. 13(2) p. 150 (1969).
C. C. Williams, H. K. Wickramasinghe: "Absolute optical ranging with 200-nm resolution" in Optics Letters vol. 14 No. 11, Jun. 1, 2989, p. 542-544.
K. E. Docherty, J. M. R. Weaver: "Improvements to the alignment process in electron beam lithography" in University of Glasgow Engineering Graduate School Postgraduate Conference 2007.
K. E. Docherty: "Improvements to the alignment process in electron beam lithography" 1st Year Progress Report, University of Glasgow 2006.

* cited by examiner

USES OF ELECTROMAGNETIC INTERFERENCE PATTERNS

RELATED APPLICATIONS

This application is a 35 U.S.C. §371 national phase application of PCT/GB2009/002071 (WO 2010/023442), filed on Aug. 25, 2009, entitled "Uses of Electromagnetic Interference Patterns", which application claims priority to GB 0815514.5, filed Aug. 26, 2008, and GB 0823707.5, filed Dec. 31, 2008. Each of these applications is incorporated herein by reference in its entirety.

BACKGROUND TO THE INVENTION

Field of the Invention

The present invention provides various uses of electromagnetic interference patterns, and particularly (but not exclusively) to uses of visible light interference patterns, UV interference patterns and IR interference patterns. Typical uses disclosed herein relate to spatial metrology, such as a translational and/or angular position determination system, and to methods for such position determination. Further uses include the analysis of properties of the electromagnetic radiation itself (such as the determination of the wavelength of the electromagnetic radiation). Still further uses include the analysis of one or more properties (e.g. refractive index) of the matter through which the electromagnetic radiation passes.

Related Art

U.S. Pat. No. 4,111,557 discloses a method for determining the shape or position of an object with respect to the shape or position of a reference object. The reference object may be a master object, a scale model, or an ideal object which is determined only by computation or graphically, or it may be the same object observed at a different time.

In U.S. Pat. No. 4,111,557, light rays from a coherent source are projected as lines and/or point arrangements onto an object using lenses. These lines or point arrangements are transferred to an optoelectronic recording device (e.g. a TV camera or a photodiode matrix) by means of an objective lens. The signals produced by the recording device are converted into digital data for storage and for comparison with the data corresponding to the reference object.

Other known optical positioning systems are discussed below.

WO2004/031686 discloses a laser interferometer system providing position feedback. The interferometer system disclosed in WO2004/031686 requires an external retroreflector target optic and measures changes of position along the axis of the light beam.

WO02/084223 and EP0503176 disclose optical positioning systems using scales that encode absolute position information. It is also known to provide an optical positioning system in which an LED illuminates a periodic linear scale and the reflected light is detected and analysed. The device determines the relative position between the scale and the read-head, which contains the LED and detector.

WO 2006/067481 discloses a 2D pattern and a sensor, moveable relative to one another. The pattern (e.g. an array of dots) is arranged as groups of features, each group encoding an absolute position. For example, one dot of each group may have a distinctive colour for identifying the position of that group.

SUMMARY OF THE INVENTION

Modern aeroplanes, for example, are controlled almost entirely by electronic servomechanisms. A deep hierarchy of measurement systems has been developed to enable this technology. At the bottom of the hierarchy are simple systems based on potentiometers or electrical distance measurement such as Linear Variable Differential Transformers (LVDT). These systems are (usually) inexpensive, quite precise and very inaccurate. Next in the hierarchy are systems based on the measurement of the position of a physical ruler. Such "encoders" are complex systems and are very accurate, but have a precision not much better than a simple LVDT. A particular problem with such systems is that the accuracy of the system is defined by the grating. Thus the measurement of large distances requires the production of a large and precise ruler. These rulers are expensive, massive and often require careful environmental control to prevent them from becoming contaminated. The production of a 2-dimensional grating (for example to measure x-y or rotation) is very expensive and not generally possible for very large scales. At the top of the hierarchy are interferometers. The interferometer, which measures distance in wavelengths of light, is the basis of all standard distance measurements. Interferometers are used for less accurate measurements as well, since accurate laser sources are now relatively cheap and comparison with the interferometers used in standards laboratories is straightforward. With a suitable laser an interferometer may be made arbitrarily large (for example the interferometer being used in an attempt to measure gravitational waves is 4 km in extent [J. Hough "Long Baseline Gravitational Wave Detectors—Status and Developments" *Journal of Physics Conference Series* 66 012002 (2007)]).

Interferometers have a number of problems, however. Firstly the signal produced by a monochromatic interferometer is intrinsically periodic, so that the identification of a particular position ("zero" distance) is difficult. Next, metrological interferometers are intrinsically capable of measuring distance in a single dimension only. If an interferometer is to be used to measure position in three axes one needs to use three independent interferometers together. The angular accuracy of this arrangement is subject to errors in physical construction. Alternatively, position in (for example) x-y may be measured by using a mirror to measure distance in one direction whilst being unaffected by translation in a perpendicular direction. This requires the use of very expensive mirrors.

The present inventors have realized that a novel form of position determination may be based on the use of a two dimensional intensity pattern such as an interference pattern. This is a general aspect of a first development of the invention. Such patterns may provide translational aperiodicity and may provide low rotational symmetry. A truly translationally aperiodic intensity pattern may be defined as a periodic intensity pattern with an infinite period. Thus, the term "aperiodic" or "substantially aperiodic" is intended also to include translationally periodic intensity patterns with a relatively long period, for example where the period of the pattern is comparable with or larger than a dimension of a corresponding detector for capturing part of the pattern. This can enable unique identification of absolute or relative position and orientation of an object within the pattern, even when using only a minority part of the interference pattern. A system operating on this basis may have the simplicity of installation and low cost of an LVDT and yet can measure more than one axis at a time with useful precision and accuracy.

Accordingly, in a first preferred aspect of the first development, the present invention provides a position determination system having: an electromagnetic radiation intensity pattern generator for generating a substantially translationally aperiodic intensity pattern; an object whose position is to be determined; an electromagnetic radiation detector, operable to detect all, part or a minority part of the intensity pattern produced by said generator, wherein the system is capable of determining a position of the object using the detected intensity pattern or part of the intensity pattern.

In a second preferred aspect of the first development, the present invention provides a method of determining the position of an object, the method including the steps: generating an electromagnetic radiation substantially translationally aperiodic intensity pattern; and detecting all, part or a minority part of the intensity pattern to determine the position of the object.

In a third preferred aspect of the first development, the present invention provides a method of determining the location of a minority part of an electromagnetic radiation substantially translationally aperiodic intensity pattern within the intensity pattern including the step of determining the relative locations of maxima or minima in the minority part of the intensity pattern.

In a fourth preferred aspect of the first development, the present invention provides a computer program, optionally recorded on a storage medium, for carrying out the method of the third aspect.

In a fifth preferred aspect of the first development, the present invention provides a computer or other processing means (such as a digital signal processor) operatively configured to carry out the method of the third aspect.

In a sixth preferred aspect of the first development, the present invention provides an optical element for the production of a substantially translationally aperiodic interference pattern for use in a position determination system.

In a seventh preferred aspect of the first development, the present invention provides a refractive index distortion determination system having: an electromagnetic radiation substantially translationally aperiodic intensity pattern generator; an interrogation volume; an electromagnetic radiation detector, operable to detect at least a part of the intensity pattern produced by said generator, wherein the system is capable of determining a refractive index distortion within the interrogation volume using the detected intensity pattern.

The following numbered paragraphs [A1]-[A26], set out particular preferred combinations of features. As will be apparent, other combinations of features are also disclosed herein and are within the scope of the invention.

[A1] A position determination system having:
an electromagnetic radiation intensity pattern generator for generating a substantially translationally aperiodic two dimensional intensity pattern;
an object whose position is to be determined;
an electromagnetic radiation detector, operable to detect a minority part of the intensity pattern produced by said generator,
wherein the system is capable of determining a position of the object using the detected minority part of the intensity pattern.

[A2] A system according to [A1] wherein the intensity pattern is an interference pattern.

[A3] A system according to [A1] or [A2] wherein in use, movement of the object from a first to a second position causes a change of the intensity pattern captured at the detector.

[A4] A system according to any one of [A1] to [A3] wherein the object whose position is to be determined has a fixed spatial relationship with either one of the electromagnetic radiation intensity pattern generator and the electromagnetic radiation detector.

[A5] A system according to any one of [A1] to [A4] wherein the detector is adapted to detect a plurality of maxima and/or minima in the intensity pattern substantially simultaneously in order to provide a position determination.

[A6] A system according to any one of [A1] to [A5] wherein the detector includes an array of detection elements.

[A7] A system according to any one of [A1] to [A6] wherein the detector captures the minority part of the intensity pattern directly.

[A8] A system according to any one of [A1] to [A7] wherein the object is movable by translation along at least one of three orthogonal axes and optionally about at least one of three orthogonal rotational axes, movement of the object along or about any one or any combination of these axes providing a variation in the part of the intensity pattern detected by the detector.

[A9] A system according to any one of [A1] to [A8] wherein the intensity pattern generator includes a coherent light source.

[A10] A system according to any one of [A1] to [A9] wherein the intensity pattern generator includes an optical element, or a plurality of optical elements, to produce the intensity pattern from coherent light.

[A11] A system according to [A10] wherein the optical element includes an arrangement of light-transmitting apertures for the transmission and diffraction of light.

[A12] A system according to [A11] wherein the optical element includes focusing means for directing light preferentially towards the light-transmitting apertures.

[A13] A system according to [A12] wherein the focusing means is at least one zone plate.

[A14] A system according to any one of [A11] to [A13] wherein the optical element includes a light-transmitting substrate having upper and lower surfaces, each surface having a non-light-transmitting layer formed thereon, the apertures and the focusing means being formed by removal or omission of parts of the non-light-transmitting layers.

[A15] A system according to any one of [A1] to [A14] enclosed within a substantially light-proof enclosure.

[A16] A system according to any one of [A1] to [A15] including a second detector, the second detector being for detecting a different part of the intensity pattern than the first detector.

[A17] A system according to [A16] wherein the first detector and the second detector are parts of a single main detector.

[A18] A system according to [A16] or [A17] wherein the refractive index of the optical paths between the intensity pattern generator and the first and second detectors is deliberately made to be different.

[A19] A system according to [A18] wherein a refractive index adjustment layer is included on or close to the second detector.

[A20] A system according to any one of [A1] to [A19] wherein the system is capable of generating at least a second two dimensional intensity pattern, using electromagnetic radiation of different wavelength to the first two dimensional intensity pattern, to be detected with the first two dimensional intensity pattern at the detector.

[A21] A system according to [A20] wherein each wavelength is guided towards corresponding apertures in an optical element in order to generate the intensity patterns.

[A22] A system according to [A20] or [A21] wherein the intensity patterns of differing wavelengths are detected, at least in part, on the basis of wavelength.

[A23] A system according to any one of [A20] to [A22] wherein the intensity patterns of differing wavelengths are detected, at least in part, on the basis of spacing of maxima and/or minima in the patterns.

[A24] A method of determining the position of an object, the method including the steps:
generating an electromagnetic radiation substantially translationally aperiodic two dimensional intensity pattern; and
detecting a minority part of the intensity pattern to determine the position of the object.

[A25] A method of determining the location of a minority part of an electromagnetic radiation substantially translationally aperiodic two dimensional intensity pattern including the step of determining the relative locations of maxima or minima in the minority part of the intensity pattern.

[A26] A method according to [A24] or [A25] further including the step of correlating the minority part of the intensity pattern with a calculated pattern corresponding to the intensity pattern.

The inventors have further realised that the present invention need not necessarily be limited to the use of a substantially translationally aperiodic intensity pattern. Accordingly, the following numbered paragraphs [B1]-[B22] set out particular preferred combinations of features. As will be apparent, other combinations of features are also disclosed herein and are within the scope of the invention.

[B1] A position determination system having:
an electromagnetic radiation intensity pattern generator for generating a two dimensional intensity pattern;
an object whose position is to be determined;
an electromagnetic radiation detector, operable to detect a minority part of the intensity pattern produced by said generator,
wherein the system is capable of determining a position of the object using the detected minority part of the intensity pattern.

[B2] A system according to [B1] wherein in use, movement of the object from a first to a second position causes a change of the intensity pattern captured at the detector.

[B3] A system according to [B1] or [B2] wherein the object whose position is to be determined has a fixed spatial relationship with either one of the electromagnetic radiation intensity pattern generator and the electromagnetic radiation detector.

[B4] A system according to any one of [B1] to [B3] wherein the detector captures the minority part of the intensity pattern directly.

[B5] A system according to any one of [B1] to [B4] wherein the object is movable by translation along at least one of three orthogonal axes and optionally about at least one of three orthogonal rotational axes, movement of the object along or about any one or any combination of these axes providing a variation in the part of the intensity pattern detected by the detector.

[B6] A system according to any one of [B1] to [B5] wherein the system is capable of generating at least a second two dimensional intensity pattern, using electromagnetic radiation of different wavelength to the first two dimensional intensity pattern, to be detected with the first two dimensional intensity pattern at the detector.

[B7] A system according to [B6] wherein each wavelength is guided towards corresponding apertures in an optical element in order to generate the intensity patterns.

[B8] A system according to [B6] or [B7] wherein the intensity patterns of differing wavelengths are detected, at least in part, on the basis of wavelength.

[B9] A system according to any one of [B6] to [B8] wherein the intensity patterns of differing wavelengths are detected, at least in part, on the basis of spacing of maxima and/or minima in the patterns.

[B10] A system according to any one of [B1] to [B9] wherein the intensity pattern generator includes a coherent light source.

[B11] An electromagnetic radiation wavelength detector having:
an electromagnetic radiation intensity pattern generator for generating a two dimensional intensity pattern, said generator including a coherent light source whose wavelength is to be determined;
a first electromagnetic radiation detector, operable to detect a part of the intensity pattern produced by said generator; and
a second electromagnetic radiation detector, operable to detect a part of the intensity pattern produced by said generator,
wherein the refractive index of the respective optical paths between the generator and the first and second detectors is deliberately made to be different by a known amount, the patterns detected by the first and second detectors being usable to determine the wavelength of the coherent light source.

[B12] A system according to [B11] wherein the first detector and the second detector are parts of a single main detector.

[B13] A system according to [B12] wherein a refractive index adjustment layer is included on or close to the second detector.

[B14] A system according to any one of [B1] to [B13] wherein the intensity pattern is an interference pattern.

[B15] A system according to any one of [B1] to [B14] wherein the detector is adapted to detect a plurality of maxima and/or minima in the intensity pattern substantially simultaneously.

[B16] A system according to any one of [B1] to [B15] wherein the detector includes an array of detection elements.

[B17] A system according to any one of [B1] to [B16] wherein the intensity pattern generator includes an optical element, or a plurality of optical elements, to produce the intensity pattern from coherent light.

[B18] A system according to [B17] wherein the optical element includes an arrangement of light-transmitting apertures for the transmission and diffraction of light.

[B19] A system according to [B18] wherein the optical element includes focusing means for directing light preferentially towards the light-transmitting apertures.

[B20] A system according to [B19] wherein the focusing means is at least one zone plate.

[B21] A system according to [B18] or [B19] wherein the optical element includes a light-transmitting substrate having upper and lower surfaces, each surface having a non-light-transmitting layer formed thereon, the apertures and the focusing means being formed by removal or omission of parts of the non-light-transmitting layers.

[B22] A system according to any one of [B1] to [B21] enclosed within a substantially light-proof enclosure.

Furthermore, the inventors have realised that the present invention has more general applicability to the field of measurement of physical properties.

Accordingly, in a first preferred aspect of a second development of the invention, there is provided a measurement system having:

an electromagnetic radiation interference pattern generator for generating an interference pattern including intensity maxima and intensity minima;

an electromagnetic radiation detector, operable to detect at least a part of the interference pattern produced by said generator, the detector having an array of detection elements arranged to detect a plurality of the intensity maxima and/or intensity minima of the interference pattern substantially simultaneously, wherein the system is capable of determining a physical property of the system, or a change in a physical property of the system, based on the detected intensity maxima and/or intensity minima.

In a second preferred aspect of the second development of the invention, there is provided a position determination apparatus including a measurement system according to the first aspect of the second development.

In a third preferred aspect of the second development of the invention, there is provided a wavelength determination apparatus including a measurement system according to the first aspect of the second development.

In a fourth preferred aspect of the second development of the invention, there is provided a use of a device according to the first aspect of the second development for measuring wavelength in a wavelength division multiplexed communications channel.

In a fifth preferred aspect of the second development of the invention, there is provided a refractive index determination apparatus including a measurement system according to the first aspect of the second development.

In a sixth preferred aspect of the second development of the invention, there is provided a method of measuring a physical property including the steps:

using an electromagnetic radiation interference pattern generator to generate an electromagnetic radiation interference pattern including intensity maxima and intensity minima;

using a detector to detect at least a part of the interference pattern produced by said generator, the detector having an array of detection elements, the detector thereby detecting a plurality of the intensity maxima and/or intensity minima of the interference pattern substantially simultaneously; and using the detected intensity maxima and/or intensity minima to measure the physical property, or a change in the physical property.

Preferred and/or optional features of the invention will now be set out. These are applicable singly or in any combination with any aspect of any development of the invention, unless the context demands otherwise. Similarly, any aspect of any development of the invention may be combined with another.

A preferred format for the intensity pattern is an interference pattern. Suitable patterns may be formed by diffraction. In some embodiments, it is possible for the intensity patter to be formed from a hologram. However, in preferred embodiment, the intensity pattern is not formed from a hologram. In the following discussion, the term "intensity pattern" is used interchangeably with "interference pattern".

Typically, the interference pattern occupies a volume of space between the generator and the detector, the detector "seeing" the interference pattern at a section through the interference pattern corresponding to the location of the detector. In principle, the detector can be located at any part of the volume of space occupied by the interference pattern, in order to achieve substantially the same effect. This is because typically the interference pattern does not go in and out of focus with distance from the generator. Instead, typically, at increasing distance from the generator, the spacing between adjacent maxima in the interference pattern increases.

The Nyquist limit for sampling of the interference pattern at the detector is reached when the maxima of the interference pattern are spaced apart at a pitch equal to twice the pitch of the detection elements. This is therefore the preferred lower limit for the relative spacing of the maxima of the interference pattern and the detection elements, corresponding to twice the highest spatial frequency present in the interference pattern. However, suitable measurements may still be obtained when the maxima of the interference pattern are spaced apart at a smaller pitch than this preferred lower limit. The maxima of the interference pattern are preferably spaced apart by up to 5 times, 10 times, 20 times or 100 times the pitch of the detection elements. The use of longer fringe wavelengths (i.e. greater spacing of the maxima, and therefore lower spatial frequency in the interference pattern) has the advantage that the number of measurements of intensity per maximum in the pattern is increased. However, a disadvantage of using longer fringe wavelengths is that the location of a maximum which is less sharp is intrinsically less well defined. In the case that the analysis of the pattern is accomplished by means of transforms such as a Fourier transform, the use of a fringe spacing of less than twice the spacing of the detector elements may result in aliasing. Nevertheless, if the approximate separation of the detector and optic are known, it will be possible to infer the position of optic relative to detector with high accuracy. Aliasing of the pattern makes the determination of position ambiguous without further information being available, but does not render such a determination impossible. Thus the operation of a system in such a case may be envisaged and may be advantageous in some cases, e.g. where the rate of change of detected pattern with displacement is very high. Note that such detection can be carried out without recourse to Fourier transformation, if desired.

The electromagnetic radiation typically has at least one wavelength in the range 200 nm to 12 μm. This corresponds to the region of the electromagnetic spectrum from middle and near ultraviolet to infra red wavelengths for which pixellated detector are available (e.g. for the use of $CO_2$-based lasers and mercury-cadmium-telluride detectors). The upper limit for this range is more preferably 1.6 μm, in order to include at least the important 1.5 μm communications band wavelengths. More preferably, the electromagnetic radiation has at least one wavelength in the range 380-1000 nm (or 380-750 nm, corresponding to the visible light spectrum). This is of significant interest, since detectors suitable for detection of visible light or near infra red are available at low cost but at very high quality, in terms of the arrangement of detection elements. For example, the detector may be suitable for use in a digital camera. One specific wavelength of interest is 860 nm, e.g. available from a DFB laser. A suitable detector may be similar to a commercial digital camera imaging chip, but with any infra red filter removed, where necessary for the wavelength of interest.

At the detector, the interference pattern is preferably a two dimensional interference pattern. By two dimensional, it is intended to mean that the maxima and minima are disposed in an array having variation in at least two dimensions. In this case, it is preferred that the detection elements are arranged in a one dimensional array or in a two dimensional array at the detector. By one dimensional detector array, it is intended that the detectors are arranged in a line, typically a straight line. By two dimensional detector array, it is intended that the detectors are arranged at a surface, typically a plane. The combination of a two dimensional interference pattern with a one dimensional detector has advantages where the system is for on-axis (or near-on-axis) rotational measurement, since rotation of the interference pattern and the detector relative to each other provides an identifiable variation in the part of the interference pattern captured by the detector, and the readout of the detector may be fast, particularly if the total number of detector elements is low. The combination of a two dimensional interference pattern with a two dimensional detector has advantages where the system is for translational measurement or for off-axis rotational measurement, since further information is typically required in these situations in order to determine the relative movement of the interference pattern and the detector.

Alternatively, at the detector, the interference pattern is a one dimensional interference pattern. By one dimensional, it is intended here that the interference pattern has maxima and minima disposed in an array such that minima are disposed between adjacent maxima substantially only along one dimension. In this case, preferably the detection elements are arranged in a two dimensional array at the detector. The combination of a one dimensional interference pattern with a two dimensional detector has advantages where the system is for on-axis (or near-on-axis) rotational measurement, since rotation of the interference pattern and the detector relative to each other provides an identifiable variation in the interference pattern captured by the detector.

The detector may have a three dimensional detector array. Typically, in such an array, there are multiple layers of detection elements, each layer including a two dimensional array of detection elements. For example, suitable three dimensional detector arrays are available from Foveon, Inc. (2880 Junction Avenue, San Jose, Calif. 95134, USA), such as the Foveon X3 14.1 MP image sensor (http://www.foveon.com/article.php?a=222—accessed 19 Aug. 2009).

Preferably, the measurement system further includes an object whose position is to be measured. The object whose position is to be determined may have a fixed spatial relationship with either:
(i) the electromagnetic radiation interference pattern generator, or
(ii) the electromagnetic radiation detector.

Typically, in use, movement of the object from a first to a second position causes a change of the interference pattern captured at the detector. The object may be movable by:
  (i) translation along at least one of three orthogonal translational axes; and/or
  (ii) rotation about at least one of three orthogonal rotational axes,
movement of the object along or about any one or any combination of these axes providing a variation in the interference pattern or the part of the interference pattern detected by the detector. The system may be adapted to detect this variation and to gauge the second position relative to the first position on the basis of this variation. It will be understood here that the movement of the object need not in fact be along or around any of the defined axes, but that the movement of the object can be described in the coordinate system defined by these axes. A typical movement can be described by a suitable combination of components along and/or around these axes.

The distance between the generator and the detector may be fixed. This is of particular utility for on-axis rotational measurement, and for non-movement-based physical measurements (e.g. wavelength determination or refractive index measurement). The generator and the detector may be substantially aligned about a common principal axis, the system being adapted to determine angular position about the common principal axis. In this case, the detector may be aligned (or adjustable to be aligned) perpendicular to the principal axis. Similarly, the generator may be aligned (or adjustable to be aligned) so that a centre of rotational symmetry of the interference pattern is aligned with the principal axis. It may be preferred that the a centre of rotational symmetry of the interference pattern is not, however, coincident with the principal axis, in order to ensure that relative rotation of the interference pattern and the detector from a start position (at 0 degrees) by less than 360 degrees does not provide an identical distribution of the interference pattern at the detector.

Additionally or alternatively, the interference pattern may be provided with at least one intensity marker to provide the overall interference pattern with a lack of rotational symmetry. This intensity marker may be superposed on the interference pattern.

In other embodiments, it may be preferred that the relative positions of the generator and the detector are fixed. This is of particular utility for non-movement-based physical measurements (e.g. wavelength determination or refractive index measurement).

Preferably, the detector is adapted to detect a plurality of maxima and/or minima in the intensity pattern substantially simultaneously in order to provide a position determination. As explained above, the intensity pattern may extend in at least two spatial dimensions. The detector may be adapted to detect substantially simultaneously a plurality of maxima and/or minima at different spatial positions within the intensity pattern. The detector may detect these maxima and/or minima substantially along only one dimension (for each detection event). However, it is more preferred that the detector detects these maxima and/or minima in two dimensions (for each detection event). For example, the detector may detect the maxima and/or minima along a plane intersecting the intensity pattern. Conveniently, known planar sensors (such as a CCD array, typically used in digital cameras) may be used as the detector. The detector may be translated or rotated in a direction out of the plane of the detector so as to detect the intensity pattern in a third spatial dimension.

It is preferred, in some embodiments such as positional (especially translational and/or off-axis rotational) measurement, that the detector captures only a minority part of the interference pattern. The interference pattern may be a substantially translationally aperiodic two dimensional interference pattern.

Preferably, the spacing of maxima and/or minima in the interference pattern is determined. This may be done, for example, by Fourier analysis. In determining the spacing, there is optionally included the step of mapping the detected interference pattern. This may be done by conformally mapping the detected interference pattern, for example. Furthermore, a detected part of the interference pattern may be correlated with a calculated pattern corresponding to the interference pattern.

It is possible to use more than one detector in the system. For example, a second detector may be provided that detects a different part of the intensity pattern (for each detection event) than a first detector. The first and second detectors may be at a fixed spatial relation with respect to each other. This has the advantage of providing further metrological information, for example improving the accuracy of rotational measurements at large optic-sensor separation. It is noted here that further detectors may be used. For example, three detectors may be particularly suitable. Where more than one detector is used to image a single interference pattern, the spatial relationship (e.g. alignment) of the multiple detectors may be determined without the need for precision alignment.

The first and second detectors may be two parts of a single detector array (e.g. a CCD array or similar array). This has the advantage of allowing the spatial relation between the first and second detector to be precisely known, and for the first and second detectors to be coplanar.

Additional metrological information may be obtained by deliberately varying the optical properties of the optical path between the intensity pattern generator and the first and second detectors. For example, the refractive index of these optical paths may be deliberately made to be different. One convenient way to achieve this is to include a refractive index adjustment layer, such as an etalon (or similar), on or close to the second detector, or at least in the optical path between the generator and the second detector. The difference in refractive index in the optical path means that the first detector may be assumed to "see" the "real" depth of the intensity pattern and the second detector may be assumed to "see" the "apparent" depth of the intensity pattern. If the difference in refractive index is known, then it is possible for this arrangement to provide a distance reference for the system. Additionally or alternatively, this arrangement may provide a means for calibrating the wavelength of the coherent light source (e.g. laser). This is highly advantageous, since it may allow the use of a laser with relatively poor wavelength stability, with corresponding reduction in cost and overall package size.

Such an arrangement as described above has particular utility in measurement of wavelength of the electromagnetic radiation.

Preferably, in use, the detector intercepts (and thus has the opportunity to detect) at least 10 maxima and/or minima in a single detection event. By "single detection event" it is meant that the detector is capable of detecting the maxima and/or minima substantially simultaneously. In the case of a detector including an array of detector elements (e.g. a CCD array or similar) then a "single detection event" may be considered to be the same as a frame. It is further preferred that, in use, the detector intercepts (and thus has the opportunity to detect) more than (perhaps significantly more than) 10 maxima and/or minima in a single detection event. For example, this lower limit may be at least 20, at least 50, at least 100, at least 200, at least 300, at least 400, at least 500, at least 1000, at least 10000, at least 100000 or at least 1000000. As the number of maxima and/or minima increases, so the random error of the positional information derived from the system can be very small, corresponding to high precision.

By "minority part" it is intended to mean that the detector is arranged to receive less than half of the available light in the intensity pattern. The available light in the intensity pattern corresponds to the light output from the pattern generator. Preferably, the detector is arranged to receive 40% or less, 30% or less, 20% or less, 10% or less or 5% or less of the available light in the intensity pattern. In some applications, such as wavelength measurement, it is preferred that the detector receives substantially all of the available light in the intensity pattern.

Preferably the detector includes an array of detection elements, referred to herein as pixels. One such class of detectors includes CCD (charge-coupled device) image sensors, which will be well known to the skilled person. An alternative class of detectors includes CMOS image sensors, which will also be well known to the skilled person. Both classes of detectors are used extensively in the photographic camera and camcorder industry, for example.

A particular advantage of using a pixelated detector is that the pixels are typically spatially arranged very precisely on the sensing surface of the detector. This is due to the exacting semiconductor fabrication process used for such detectors. A further advantage is that the sensing surface is typically very flat. These features allow the detector to capture the minority part of the intensity pattern is a manner which is subject to only small errors. A further advantage of using typical pixelated detectors is that the number of pixels in the detector can be very large, e.g. $10^5$ pixels, $3\times10^5$ pixels (corresponding to VGA), or $10^6$ pixels or more. For example, commercial detectors such as the KAF50100 detector from Kodak provides $50.1\times10^6$ pixels.

Preferably, in the system, the detector captures the minority part of the intensity pattern directly. Thus, for some preferred embodiments of the invention, there is preferably no functional optical element (such as a lens) between the intensity pattern generator and the detector. This avoids the introduction of errors due to inevitable aberrations of such a functional optical element. Alternatively, if a reflecting means is used to reflect the intensity pattern towards the detector, preferably there is no further functional optical element (such as a lens) between the reflecting means and the detector. As mentioned above, it is possible for the detector to detect the maxima/minima of the interference pattern without focusing. Still further, other embodiments of the invention are described below which include an etalon in at least part of the optical path between the generator and the detector, the etalon providing technical advantages over embodiments without etalons.

Preferably, the object is movable by translation along 1, 2 or most preferably 3 axes (typically orthogonal axes). The object may additionally or alternatively be moveable about 1, 2 or preferably 3 rotational axes (typically orthogonal rotational axes). It is preferred that a movement of the object along or about any one or any combination of these axes provides a variation in the part of the intensity pattern detected by the detector.

Preferably, the electromagnetic radiation provided by the interference pattern generator is spatially coherent. The coherence length is typically large enough that the maxima/minima of the interference pattern have sufficient visibility to be detected and analysed over the detector for all desired motions of the detector. For example, in the case where the interference pattern is produced by an array of apertures in an optical element, the minimum coherence length is preferably the maximum spacing between the apertures. Taking the example where the apertures are arranged at the vertices of a regular polygon (e.g. 5 apertures arranged at the vertices of the pentagon), then the minimum coherence length is preferably the diameter of a circle coincident with the vertices. Of course, where the apertures are arranged in a less regular arrangement, similar requirements hold, referred to below as the "diameter" of the array of apertures. When the coherence length meets this preferred requirement, the interference pattern extends over all space in front of the generator. A coherence length smaller than this will result in a pattern filling a reduced angle in front of the generator. This may be acceptable or even preferred for some applications. Thus, if it is desired to fill a +/−45 degree cone in front of the detector then a coherence length of <aperture array diameter>*sin(45 degrees). When it is required to fill only a very small angle, however (e.g. in the case of (position measurement over a small range far from the pinholes, e.g. for wind turbine blades) then the coherence length should be small.

Preferably the generator includes a coherent light source, such as a laser. A gas laser is particularly suitable from a technical viewpoint, since such lasers can provide steady wavelength. Typical gas lasers include He—Ne, Ar, Kr, Xe ion, $N_2$, $CO_2$, CO lasers. Infrared lasers such as $CO_2$ and CO lasers can be used, although corresponding infrared detectors (e.g. using mercury-cadmium-telluride) are significantly more expensive than optical detectors, in view of the economies of scale that have been developed for optical detectors. Alternatively, a solid state laser may be used. There are many different types of solid state laser, but YAG-based or YLF-based solid state lasers are preferred (e.g. Nd:YAG) since they can have good temperature stability of centre wavelength. Semiconductor diode lasers are also preferred, especially types having long coherence length such as distributed feedback lasers, distributed Bragg reflector lasers and vertical cavity surface emitting lasers. Fiber optic solid state lasers such as erbium-doped fiber lasers are also preferred sources. Other types of laser can be used. For example, YAG can be doped with Ce, Pr, Sm, Eu, Ho, Er, Tm, Tb and Cr, as well as Nd.

The coherent light source may be operated to provide a pulsed light signal. The frequency of pulsed operation of the signal is preferably at least 10 Hz, more preferably around 25 Hz. This may allow suitable operation of the detector. Of course the coherent light source should produce light of a frequency that can be detected by the detector, preferably at or near the frequency corresponding to the optimum signal-to-noise and/or dynamic range of the detector. Typically, the pulse repetition frequency is limited by the detector. Preferably the detector has sub-regions allowing a rate of at least 10 kHz. Preferably the width of each pulse of the pulse light signal is 50 ns or less, e.g. about 10 ns or about 100 fs.

During operation of the system, it is preferred that there is at least one pulsed light signal for each interrogation of the detector (i.e. "detection event"). Shorter pulse width gives better time resolution. However, shorter pulse width may compromise coherence length, so there is a tradeoff for very short pulses. Note that the present inventors consider that the tradeoff is much less severe than is the case for conventional interferometers. It is preferred that the pulse energy is sufficient to give good signal to noise ratio in the detector.

Pulsing can help to eliminate problems due to any relative motion between the generator and the detector while the measurement is made. Additionally, because the system typically uses beams of light which interfere at an angle, the fringes have longer period. Since the coherence length limits the number of fringes of path difference, the system can measure motions over a distance larger than the coherence length of the light source. This makes it possible to use very short pulse lasers (such as the 100 fs pulse length mentioned above). Pulsing may also reduce the average power input for the same average optical output power.

However, there can in some circumstances be advantages to operating in CW (continuous wave) mode rather than in pulsed mode. For example, the pulsing may cause optic damage, "chirping" during the pulse, and there may be safety issues. An to pulsing of the laser is to use an electronic shutter (already present in many detectors) to gate the detector, instead of the laser.

Preferably the intensity pattern generator includes an optical element (or plurality of optical elements) to produce the intensity pattern from coherent light. Preferably the optical element is in a fixed positional relationship with respect to the coherent light source, at least for the duration of a position determination operation. However, in some embodiments it is possible to provide a moveable optical path between the coherent light source and the optical element, such as an optical fibre arrangement.

Preferably the optical element includes an arrangement of light-transmitting apertures for the transmission and diffraction of light. The apertures may be arranged in a predetermined pattern. The apertures may be pinholes. For example, a regular pentagonal array of 5 pinholes has been found to be suitable for implementing a preferred embodiment of the invention. Similarly, an array of 19 pinholes has been found to be suitable. However, the present invention is not necessarily limited to these and different shapes of apertures and/or different numbers of apertures may be used. The main requirement for some preferred embodiments of the invention is that the resultant intensity pattern is substantially translationally aperiodic, as discussed above. However, this requirement does not necessarily mean that the pattern may have only zero symmetry. The pattern may, for example, have rotational symmetry. Such a pattern may still be used with the present invention, but will be limited in the maximum angle of rotational movement that can be uniquely detected. A further desirable feature of the pattern is that there is a distribution of maxima and minima in the pattern, over a usefully large area of the pattern and measurement space.

The apertures may each be formed of a small area of diffraction grating. For example, each aperture may comprise two or more slits (e.g. rectangular slits). This has the advantage of allowing control over the angular distribution of intensity. Alternatively, elliptical apertures may be used, e.g. in order to allow for polarization effects.

The present inventors have found that useful intensity patterns can be produced using an optical element as set out above. Such an optical element may, for example, be provided by an array of light-transmitting apertures in an otherwise non-light-transmitting member. The non-light-transmitting member may be an opaque film, for example, e.g. formed on a substrate. In order for the pattern to extend into a relatively large measurement space, the apertures must typically be small. The result of this is that a large proportion of the light incident on the optical element is not transmitted, and so the efficiency of the system may be low.

In order to address this problem, it is preferred that the optical element includes focusing means for directing light preferentially towards the light-transmitting apertures. For example, each aperture may be associated with a corresponding focusing means. Preferably the focusing means brings the incident light to a focus or an approximate focus at the light-transmitting apertures. The focusing means may be realised as a phase object. Each focusing means may be a zone plate associated with each aperture. The zone plate pattern may be etched into a dielectric film or an opaque metal film. It is considered that the zone plate formed in a dielectric film may provide higher efficiency. The focusing means may be selected from: at least one zone plate, at least one lens or microlens, at least one mirror, at least one spatial light modulator and at least one hologram.

The optical element may suitably be formed using a light-transmitting substrate having upper and lower surfaces, each surface having a non-light-transmitting layer formed thereon. The apertures and the focusing means may then be formed by removal or omission of parts of the non-light-transmitting layers. For example, this may be carried out using lithographic techniques, such as e-beam lithography. This allows the apertures and the focusing means to be formed with high spatial precision.

The focusing means may be formed by shaping of a surface of the light-transmitting substrate. For example, the focusing means may comprise a phase optic, e.g. a kinoform or a binary phase zoneplate.

In some embodiments, the apertures (i.e. the optical sources for the interference pattern) are preferably located at the focal points of a diffractive optical element, such as a hologram or a kinoform or an array of zone plates. The use of a kinoform in particular is preferred because it allows the suppression of the "−1" order focal spots. One disadvantage of such a system is that the position of the focal spots will depend strongly on the alignment of the laser to the optical element in the generator, and also on the wavelength of the laser.

Where the aperture is a pinhole, the edges of the pinhole can be defined with very high accuracy. In that case, the role of the remainder of the optical element is to ensure that the pinholes are evenly illuminated. However, any means to produce an array of coherently illuminated compact sources can be used. For example, the optical element may comprise a bundle of optical fibres (e.g. single-mode fibers), or an array of microlenses or an integrated optics network with gratings, prisms or facets to couple the light into free space at particular points.

In the system, there are various permutations of the layout of elements of the system with respect to each other.

In one permutation, the coherent light source and the optical element (together forming the intensity pattern generator) may be fixed with respect to each other and the object and the detector may be fixed with respect to each other. This is perhaps the most simple basic layout.

In another permutation, the coherent light source and the optical element and the detector may be fixed with respect to each other. In this case the object may include reflecting means to reflect at least a portion of the intensity pattern to the detector, so that movement of the object can be detected. This has the advantage that the object need not have an active, power-consuming device at its location, and therefore thermal management at the object location is more straightforward.

In another permutation, the coherent light source and the optical element may not be fixed with respect to each other. In this case, the coherent light may be transmitted to the optical element along an optical path such as an optical fibre, for example. In this case, the optical element may be fixed with respect to the object. The detector may be fixed with respect to the coherent light source. Again, in this case, there is the advantage that the object need not have an active, power-consuming device at its location.

The present inventors further consider that the system may be operated using two or more wavelengths of electromagnetic radiation (typically light). The advantage of this is that there may then be provided a corresponding number of intensity patterns. These may be generated by the same generator. However, it is preferred that each wavelength is guided, typically within a single optical element, towards corresponding apertures in the optical element in order to generate the intensity patterns. The intensity patterns of differing wavelengths may be detected, at least in part, on the basis of wavelength (e.g. via filtering). Additionally or alternatively, the intensity patterns of differing wavelengths may be detected, at least in part, on the basis of spacing of maxima and/or minima in the pattern. Conveniently, as the light source, there may be used a laser which is capable of outputting two wavelengths, e.g. a DPY laser. Preferably, the intensity patterns of different wavelengths have different rotational periodicity.

The system may further include path modification means to provide at least two different path lengths for the electromagnetic radiation from the generator to the detector, so as to provide at least two interference patterns at the detector, corresponding to the at least two different path lengths. Typically, the at least two interference patterns at least partially overlap at the detector.

Preferably, the path modification means provides three or more different path lengths for the electromagnetic radiation from the generator to the detector. The path modification means may provide a difference in reflection of the electromagnetic radiation along the respective path lengths. For example, an etalon may be provided between the generator and the detector, the different path lengths being provided in use by different numbers of transits of the electromagnetic radiation across the etalon before reaching the detector. The difference in path length for the different intensity patterns provided at the detector may be used in the determination of the wavelength.

In some embodiments, the electromagnetic radiation may have a coherence length shorter than the double-round-trip path in the etalon. The reason for this is that then subsequent patterns are not be capable of interfering together.

Preferably, in use, the electromagnetic interference pattern generator is operable to generate electromagnetic radiation interference patterns based on electromagnetic radiation with at least two components of different wavelength. The system may further including a wavelength-dependent separator for spatially separating the components of different wavelength towards different parts of the detector, interference patterns corresponding to each component in use optionally partially overlapping at the detector. The wavelength-dependent separator may be a wavelength-dependent dispersion arrangement or a wavelength-dependent filter arrangement. The invention may allow the determination of at least one or both of the wavelengths.

Preferably, the system is enclosed within a substantially light-proof enclosure or operate in low light conditions. This assists in providing a low noise background for the detector.

BRIEF DESCRIPTION OF THE DRAWINGS

Preferred embodiments of the invention will now be described, by way of example, with reference to the accompanying drawings, in which:

FIG. 21A illustrates the first wavelength (e.g. red light) and FIG. 21B illustrates the second wavelength (e.g. green light).

DETAILED DESCRIPTION OF THE PREFERRED EMBODIMENTS, AND FURTHER OPTIONAL FEATURES

Figure 1:
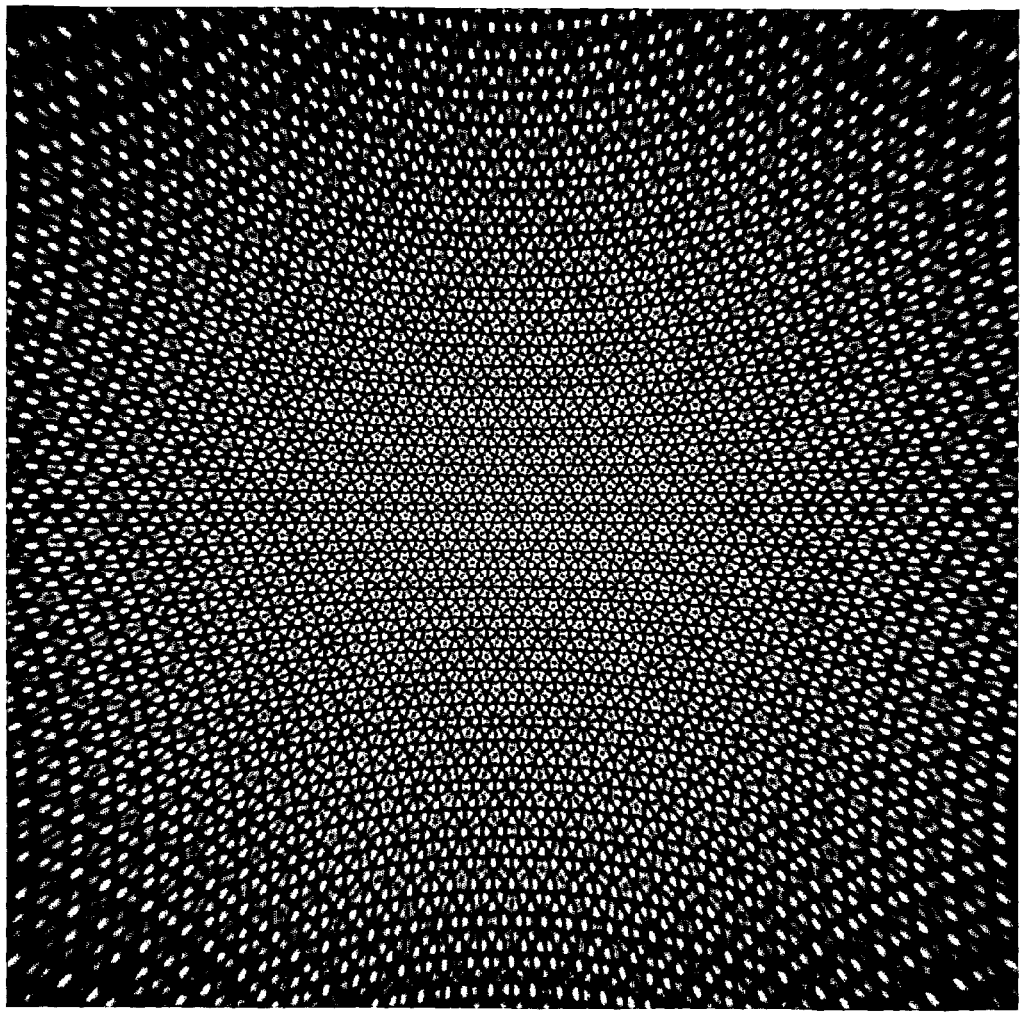
FIG. 1 shows a translationally aperiodic diffraction pattern formed using an optical element having five pinholes, arranged on the vertices of a regular pentagon, for use in an embodiment of the invention.

The measurement of position is a very important task in modern technology. The preferred embodiments of the present invention permit position to be measured with extremely high precision at very low cost. The preferred embodiments provide physically small and highly configurable systems.

We first set out here in simple terms the way in which the system works, based on a notional example of an optical system consisting of a photographic projector and a screen. An image is projected onto the screen. Typically, the picture is slightly smaller than the screen. In a first case, the projector is head-on to the screen, so the image is "square" to the screen. In a second case, if the projector is moved closer to the screen, then the image gets smaller. Thus the size of the image on the screen is a measure of how far away the projector is from the screen. If the size of the image on the screen is measured, this allows the distance from the projector to the screen to be determined.

Other determinations of the relative alignment of the projector and the screen can be made. When the projector is not exactly square-on to the screen, it is typically slightly below the screen, pointing up. In this case the bottom of the image will be small and the top of the image will be large. The image will be distorted into a trapezium shape. The character of the distortion is therefore a measure of the angle at which the projector is pointing relative to the screen.

In the preferred embodiments of the present invention, by examining the magnification, distortion, position (up or down) and rotation of an image, it is possible to infer where the projector is relative to the screen and in what direction it is pointing. The projector can be moved in any direction, but any movement can be defined by suitable combinations of movements in 6 possible directions. These are translations along axes x, y, z and rotations about these axes, and so there is provided an unambiguous measure of position in 6 dimensions (x, y, z, +all 3 rotation axes). The accuracy of the position measurements that may be provided with embodiments of the present invention is of the order of 100 nm in a cubic inch (systematic error), with a random error which is essentially zero. In preferred embodiments, the accuracy may be improved.

It is possible to determine the relative position of the image to the screen even if not all of the image is captured at the screen. If, for example, the projector is moved very far from the screen, then only a small part of the image is captured at the screen. Provided that each part of the image is different from the other parts of the image then it is in principle possible to determine which part of the image has been captured at the screen. However, when parts of the image are highly uniform, or similar to other parts, it can be difficult to make this determination.

Another difficulty with this example is that using a simple projector means that as the projector is moved away from the screen or closer to it, then the image goes out of focus. It is more difficult to identify blurred parts of an image.

Figure 2:
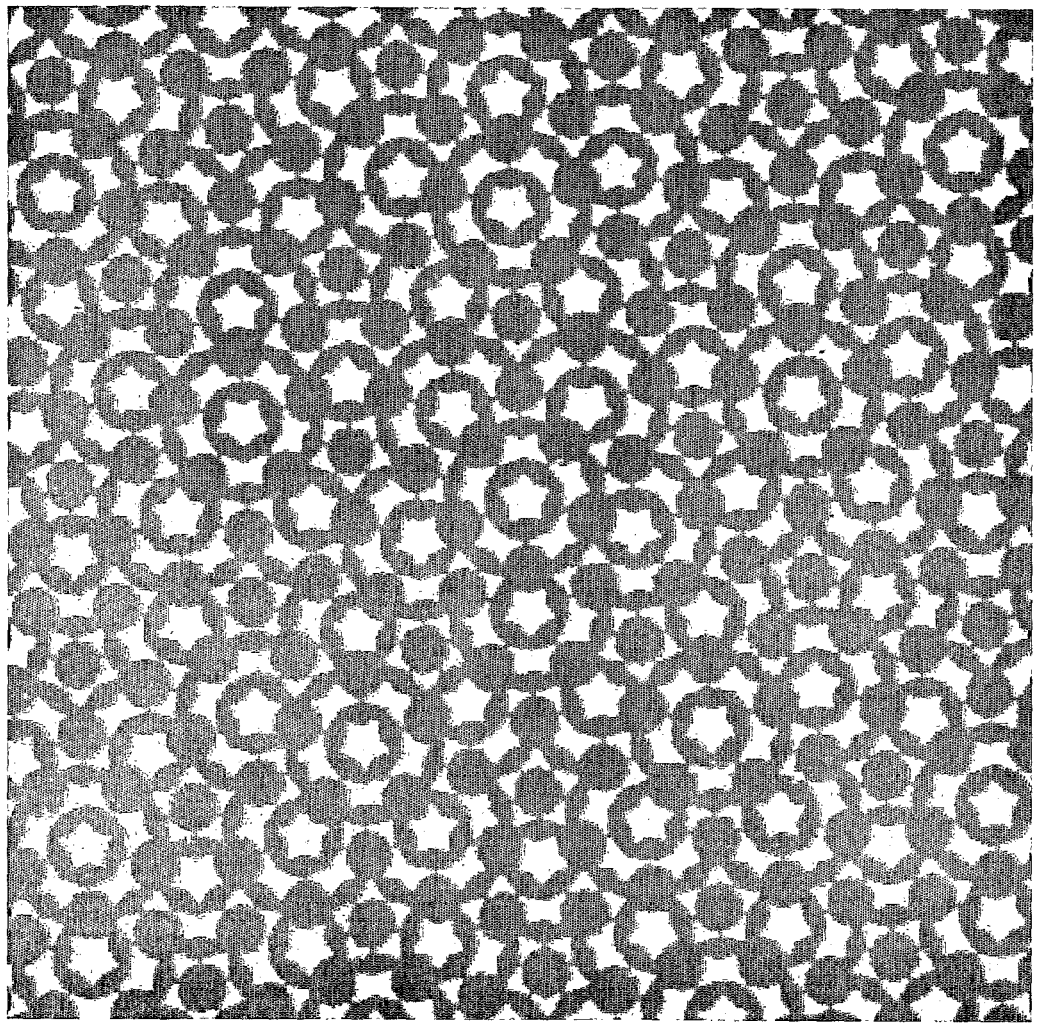
FIG. 2 shows an example of Penrose tiling.

In order to provide a more useful system the "projector" and "image" parts of the system should preferably provide the following properties:

The image should provide a large amount of fine detail, but should be different everywhere
The image should never go out of focus
The image should be one whose structure is known The preferred embodiments of the invention use a translationally substantially aperiodic real space diffraction pattern. A simple example of such a pattern is the diffraction pattern from five pinholes, arranged on the vertices of a regular pentagon. This diffraction pattern is shown in FIG. 1. The pattern shown in FIG. 1 has 5-fold rotational symmetry, which makes it never repeat under translation, just like a Penrose tiling. A typical Penrose tiling is shown in FIG. 2. Such a pattern is translationally aperiodic in that there is no translational symmetry. It can be seen that, locally, certain "themes" repeat, but for a sufficient area of the image there is only one part of the pattern which looks like itself.

Thus the optical field has characteristics similar to a mathematical object called a "Fibonacci pentagrid" ["Diffraction from one- and two-dimensional quasicrystalline gratings" N. Ferralis, A. W. Szmodis, and R. D. Diehl *Am. J. Phys.* 72 (9) p. 1241-6 (2004)]. Since the "map" of the optical field is simply derived from knowledge of the geometry of a simple optical object (e.g. a pinhole array), the position of a detector plane and the wavelength of a laser, it is possible to work backwards from the observed field (which never repeats translationally) and a knowledge of the pinhole geometry and laser wavelength to a knowledge of the position of the plane relative to the optical element.

Since the image of FIG. 1 is a diffraction pattern, it does not go out of focus. Instead, it just fills space like a hologram. Also, since the image is a well defined mathematical object, produced by diffraction from a simple arrangement of holes, it is possible to calculate what any part of the image should look like. Thus, the "map" of the picture is a mathematical formula. Therefore it should not be necessary to store a giant picture in order to match a detected image (corresponding to part of the picture) to tell where in the picture the image is.

The size of the diffraction pattern can be controlled by changing features of the optical element such as the size of the pentagon (in the case of a diffraction pattern such as in FIG. 1) and the diameter of the holes in the optical element. In this way, the diffraction pattern can be caused to fill as large or small a volume of space as is required, and the separation of the maxima (bright spots) in the diffraction pattern can be matched to the resolution of a detector (equivalent to the "screen" in the example above).

Figure 3A:
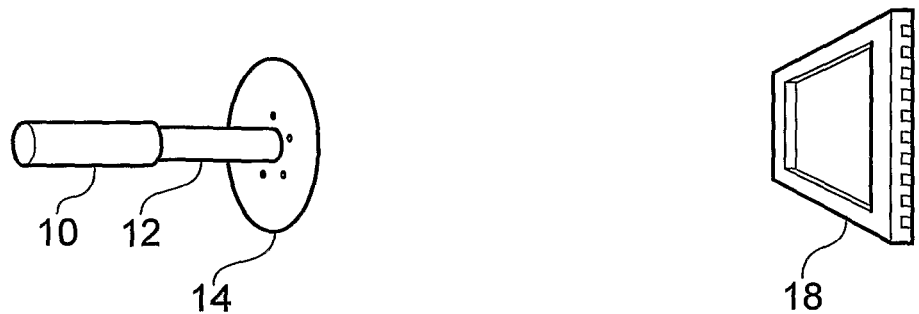
FIG. 3A shows a schematic perspective view of a system according to an embodiment of the invention.
Figure 3B:
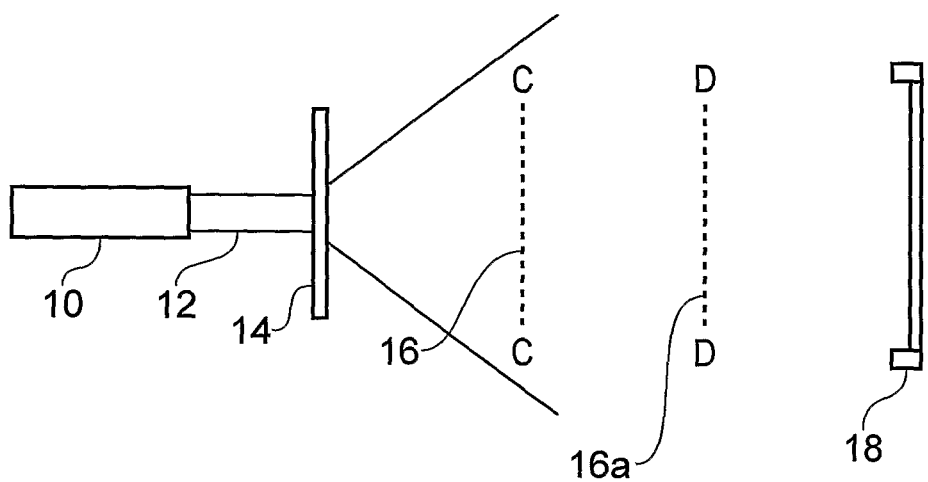
FIG. 3B shows the system of FIG. 3A in cross sectional side view.
Figures 3C, 3D:
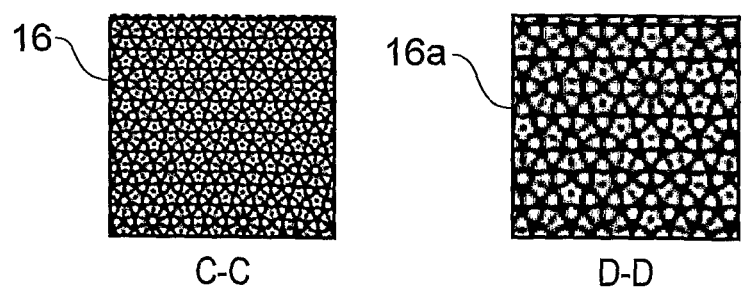
FIGS. 3C and 3D show a front-on schematic view of the diffraction pattern that would be captured at C-C and D-D, respectively, in FIG. 3B.

The physical realisation of the system is illustrated in FIG. 3. The diffraction pattern generator, equivalent to the projector in the example above, consists of a laser onto which is attached (e.g. glued) an optical element in the form of a pinhole array. Typically, the optical element is a small chip of quartz with a non-light-transmitting layer patterned using electron-beam lithography. On the back of the optical element is another pattern (also written by electron beam lithography) which focuses the laser onto the pinholes.

Most of the alignment work involved in fabricating the system is performed at the wafer scale as the pinhole array is fabricated. The choice of laser is unconstrained. For example, one useful laser is a miniature diode pumped YAG laser, similar to those used in laser pointers. These are available in 1 $cm^3$ packages, allowing the system to be compact and robust. The detector (corresponding to the "screen" in the above example) is a solid state camera chip, based on COD or CMOS technology. These are available in a range of sizes and pixel counts. As will be apparent to the skilled person, other types of detector may be used. Typically, the detector will be chosen based on various factors, including the wavelength of the electromagnetic radiation used to create the interference pattern. For example, the detector can be provided in a 1 $cm^3$ package. Since the system operates to determine the complete orientation of the diffraction pattern generator and the detector, no special care needs to be taken to align the two in hardware. Instead the coordinate system of the object being measured may be translated from the coordinate system of the measuring device in software, eliminating cosine error and the need for precise alignment of the measuring system to the physical axes of motion of the measured system.

CCD or CMOS photosensors are routinely produced with pixel placement accuracies of better than 50 nm for a current process (overlay at the 130 nm node is 65 nm over a wafer). Thus a low cost camera chip is (coincidentally) a highly accurate ruler. A typical detector chip suitable for use with the preferred embodiments is a commercially available 1.3 megapixel chip. The skilled person will immediately understand, however, that different detector chips (typically with more pixels) regularly become available and could similarly be used with the present invention.

As mentioned above, the system can be modified in order to change the size of the diffraction field by modifying the pattern on the optical element. Using electron beam lithography to form the pattern on the optical element is advantageous since the pattern formed using modern electron beam lithography machines is determined using software rather than a photolithographic mask. Furthermore, the size and shape of the pinholes can be very accurately defined.

Where the optical element is of large size, it can be preferred to manufacture the optical element via other processes, e.g. using nano-imprint lithography or photolithography. Such processes are capable of forming features of dimensions down to about 20 nm (e.g. using deep ultraviolet lithography), corresponding to random positional errors of about 2 nm.

Typical systems embodying the invention can interrogate volumes of a few tens of cubic centimetres (a few cubic inches). Such systems are suitable for use in optical microscopes and optical stages.

Alternative systems may be configured using a different laser. The advantages of a doubled Neodymium YLF/YAG microlaser are the small size, low power, low cost and yet the beam has a good shape at a well-defined wavelength. There are many possible lasers that could be used. Suitable alternative lasers are listed in Table 1.

TABLE 1

Lasers

| Laser type | Advantages | Size | Cost | Disadvantages |
|---|---|---|---|---|
| HeNe (JDSU) | Closely defined wavelength (about 1 GHz) | 15 cm-50 cm long, 2-5 cm diameter | €300-1000 | Large size, high power, awkward to mount |
| Stabilized HeNe (Newport) | Excellent wavelength accuracy | 40 cm long, 4.5 cm diameter | About €5 k | Large size, high power, awkward to mount and expensive |
| Nonplanar Ring Oscillator YAG (JDSU) | Excellent wavelength accuracy | 20 × 8 × 5 cm | About €15 k | Large size, high power, awkward to mount and expensive |
| Q-switched microlaser (Teem Photonics) | Short pulses: "Stroboscopic" measurement | 12 × 3 × 3.5 cm | [not known] | Expensive |
| F-P Diode | Very cheap, high power | ~1 cm$^3$ | Very low | Poor wavelength accuracy |
| DFB | Tunable very narrow linewidth: air compensation? | ~1 cm$^3$ | About €1000 | Optical feedback |
| Any fiber coupled laser | Ultra small source footprint, low thermal load | 0.02 cm$^3$: optic same diameter as fiber cladding | About €1000 | None |

It is considered that the preferred embodiments of the present invention will operate satisfactorily with any laser type. The detector typically is based on silicon, and visible and/or near-infrared wavelengths typically are required. In particular the requirements for long "coherence length" are very much relaxed, so that (for example) short pulse lasers may be used.

The choice of detector is wide, and is limited mainly by the need to intercept a sufficiently large part of the diffraction pattern to unambiguously locate the region under investigation.

The speed of the system is typically limited by the time taken to read out a complete image of the part of the pattern captured at the detector. For low cost consumer-type CCD and CMOS camera chips this is typically up to 50 frames per second. More complex imaging chips can be read out much more quickly, e.g. 500 frames per second for a full image [for example part number MT9M413C36STM of Micron Technology, Inc., 8000 S. Federal Way, Boise, Id. 83707-0006, USA], or tens of kilosamples per second for a small portion of the image. This is useful for the measurement of motion, where the approximate absolute position is already known, e.g. in the measurement of vibrations over the whole audio frequency range.

In this regard, it is advantageous to use a pulsed light signal. The pulse repetition frequency is basically limited by the detector, not by the laser. As mentioned above, detectors are available with tens of kHz rate for sub-regions. Also the pulse width is useful to "stop" the motion. Since the coherence length need only be equal to the pinhole spacing (as discussed above in relation to the diameter of the arrangement of apertures), not the interrogated area, the preferred embodiments of the invention have significant advantages over known interferometers. For example, a system with a 100 fs pulse length has a coherence length of 30 μm, so a normal interferometer could only measure distances of up to 30 μm. In the case of the present system, using a 500 nm wavelength laser and a 30 μm coherence length there can be provided about 60×60 fringes (maxima and/or minima). However, these can cover any area desired. Thus with a 32 μm period interferometry can be performed over about 2 mm (60×32 μm) with high precision. This has particular utility in wavefront measurement. As mentioned in Table 1 above, small passively Q-switched YLF and YAG lasers are known. These are very similar in construction to the normal green microlasers, but with an additional saturable absorber. These lasers can give a pulse of about 10 ns, allowing sample velocities of up to 30 μm in 10 ns (i.e. 3 ms$^{-1}$).

Other applications are concerned with the measurement of other distortions of the image. A simple motion of the detector relative to the diffraction pattern generator results in well-defined, smooth distortions as described above. On the other hand, if a distorting medium is present between the diffraction pattern generator and the screen, the image will suffer from an additional distortion. An example is the effect seen when observing an object through a heat haze, gently rippling water or antique window glass. The system is able to measure the extent of such additional distortion, producing a map of the variation of refractive index between the projector and the camera chip. The system is capable of doing this to very high accuracy, and hence allows "phase objects" to be imaged quantitatively with great sensitivity. Such phase objects might be due to air flow on a turbine blade, or hot air above an electronic component, or due to a transparent organism or other object in a sample of water. The system can only image phase over an area roughly equal to the size of the camera chip. Since the camera chip typically is not large, the system can only image the phase around small things. On the other hand, the system has a spatial resolution equal to a few pixel spacings (about 10 μm) so can act as a phase microscope.

In one specific application, an embodiment of the present invention is used in a stage position readout for an optical microscope. When using a microscope a user moves the sample around on a stage, looking at different regions. Typically there is a need to get back to a specific location, to record positions and sizes of relatively large objects in a sample at the micron level and to measure focal position, which is a measure of the thickness of the sample. The embodiment described with reference to FIG. 3 is ideal for this application. The provision of sub-nanometer precision and reproducibility is actually more than is necessary for this application. The ease of alignment and small size allows the system to be attached to any convenient part of the microscope. This allows the invention to be used with many different makes and models of microscope, without the need to design and manufacture specific mounts for each. The absolute accuracy of the embodiment of the invention is of the order of 0.1% without calibration. At least an order of magnitude better is achievable with a single measurement (effectively calibrating altitude and laser wavelength). The ability of the embodiment to measure all 6 axes directly means that alignment of the measurement system to the stage may be achieved in software (cosine error compensation). The embodiment also provides an inexpensive retrofittable enhancement for existing microscopes.

Embodiments of the invention find applications in many different technical fields. In addition to those already mentioned, embodiments of the invention may be used in:
  manufacturing robotics (especially in aerospace industry)
  mechanical actuators (especially those requiring precision of motion)
  optics manufacturing
  polishing
  automotive testing
  surgical robotics
  measuring tools (e.g. micrometers and dial gauges)
  micropositioning systems (e.g. lathes, milling machines, lithography tools, optomechanics, precision motion stage measurement)
  electron microscopy stages
  nanopositioning systems
  control systems (robotics, aerospace, automotive)
  quality control and processing (component metrology)
  human interface (joysticks, knobs and levers)
  scientific measurement (e.g. astronomical)
  servo control
  disposable interferometers, e.g. for use in ballistics studies on small particles
  medical interferometry (e.g. quantitative tremor measurement)
  precision contactless controllers (e.g. knobs and joysticks in explosive atmospheres)

The embodiments of the invention combine extreme precision with low cost and multi-axis capability.

Further technical detail about the preferred embodiments of the invention will now be set out.

The operation of the system is described with reference to FIGS. 3A-D. Coherent light 12 is generated by laser 10 and is used to illuminate an optical element 14. For clarity, not all of the optical element is shown illuminated in FIG. 3A, but in practice the pentagonal array of pinholes in optical element 14 would be illuminated by light 12. The optical element 14 generates a system 16 of real-space fringes which are translationally aperiodic within the pattern that is available for detection. Sample C-C of the pattern is taken at the position shown in FIG. 3B. The sampled pattern is shown front-on in FIG. 3C. A sample taken further towards the detector 18, away from the optical element, would have a greater fringe spacing, as shown by sample location D-D and in FIG. 3D. Thus the pattern imaged on the surface of the detector 18 is uniquely determined by the position of the detector within the field. The choice of aperiodic field depends on a number of criteria, discussed in detail below. In general, there is a tradeoff between the "richness" of the diffractive field (corresponding to the number of unique points which may be defined within the image and correlating with the random errors associated with locating the image) and the simplicity of the algorithms which are used to interpret the detected image as a position in space. For a suitable choice it is possible to define all 6 dimensions (3 translational and 3 rotational degrees of freedom) unambiguously. For example, in the case of a 5-fold quasiperiodic diffraction pattern (FIG. 1), there is only one degeneracy, namely the pattern repeats every 72 degrees with respect to rotation around the axis separating the optical element and the detector.

The predicted accuracy and precision of the system is a function of a number of system parameters. The fringe spacing is preferably about twice the pixel spacing of the detector. This is typically in the range 2.2 μm to approximately 20 μm for commercially available cameras. The ability of the detector to locate the maxima in the diffracted field is almost perfect. For example, if the diffracted field were to be set to give an average separation between bright spots of 4 pixel spacing (well oversampled in this naturally bandlimited case), then each image in a small (VGA=640× 480 pixel) photodetector would contain 19200 separate maxima. The identification of the position of each maximum would be limited by the signal to noise of the image (there is no loss of information in sampling a bandlimited signal). For a typical detector (50 dB SNR) a simple quadratic fit to the centre using the maximum pixel and adjacent two in each dimension gives a random error in position of $10^{-3}$ pixel spacings, (analysis performed by MonteCarlo/Excel). The random error in (for example) the translational position of the detector is therefore given by the random error in the position of each peak, reduced by approximately the square root of the number of maxima identified (and, it is conjectured, possibly also reduced by the square root of the number (6) of degrees of freedom), or approximately $$\frac{10^{-3} \cdot \text{pixel spacing} \cdot \sqrt{6}}{\sqrt{19200}} \sim \frac{10^{-3} \cdot 5\mu m \cdot \sqrt{6}}{\sqrt{19200}} = 0.088 \text{ nm}$$

This is simply compared to the precision expected using the same number of photons in a conventional (e.g. Michelson) interferometer. If it is assumed that there are $3 \cdot 10^5$ electrons per pixel (saturation point of a typical high dynamic range COD) then a conventional interferometer would give a positional accuracy of (very roughly λ/square root of the number of photons) about 0.002 nm. This is reassuring, since the detection of the position of a 20 μm "period" fringe pattern must be less precise than detecting the position of a fringe pattern having spacing of half a wavelength, so the analysis is plausible.

The Nyquist limit in this embodiment of the invention is for a pixel spacing equal to half the period of the interference pattern. (Put another way, the spacing between maxima in the interference pattern is equal to twice the pitch of the pixels.) It is possible for data to be extracted for periods of the interference pattern smaller than this, i.e. beyond the sampling limit, but the contrast of the image will diminish.

It is worth noting that the worst case is for the period of the interference pattern to be equal to the pixel pitch, since the amplitude of the detected signal will become zero.

It is useful to consider the effects of dead pixels in the detector. The pattern is developed across the whole image, and the final analysis is generally performed in the Fourier domain. Thus, after suitable distortion in real space of the image, so that the spatial frequencies under consideration are the same across the whole image, the characteristics of the waves of that spatial frequency are extracted using a windowed discrete Fourier transform, as explained in more detail below. This gives the frequency and phase relating to a pair of pinholes of the optical element. The procedure is then repeated for all pairs of pinholes. Therefore the real signal from operable pixels will all be brought together onto a single pair of points in the Fourier plane. In contrast, the signal from a dead pixel will occupy a single point in real space. The transform of a single point is a uniform amplitude over the whole of the transform. From the Wiener-Khinchine theorem, the energy in the two domains is the same. Thus the uniform sinusoidal fringe has a large total energy which is concentrated into a single spot in the Fourier plane. The defect (dead pixel) has a very small energy which is then smeared out as thinly as possible over the whole Fourier plane. Since the measurement is made by considering only the transform values near to the peak of the sine wave signal transform, the effect of a single pixel defect is therefore filtered away.

We consider now in more detail the relationship between the pixel spacing in the detector and the maxima/minima spacing in the diffraction pattern. This can be considered in three parts: (I) calculation of precision in normal operation; (II) calculation of precision for vibrometry; and (III) calculation of required proportion of pattern to determine position. A fuller discussion of random errors in the system is set out later in the description.

(I): Calculation of Precision in Normal Operation

Assuming that the 5-pinhole generator of FIG. 3 is used, the interference pattern needs to be detected without aliasing by the pixellation of the detector. Thus if we have a sinusoidal modulation of intensity we need the pixels to be spaced closer together than half a period of the sine wave (sampling theorem). The 5-pinhole array produces a pattern which is the sum of a number of sinusoids. Thus the interference pattern is intrinsically band-limited. This means we can sample very close to the Nyquist limit and lose no information whatsoever. When at its closest approach to the generator, therefore, we expect the shortest period sine wave to have a period of (say) 2 pixels on the pixel diagonal. (Note that if a colour detector chip is used, green pixels (for example) only half fill the detector area.) Thus, taking a conservative approach and allowing for only one useable pixel per 4 present and a peak-peak spacing of just over the active pixel spacing multiplied by two multiplied by the square root of two, we get one maximum for every 32 pixels. Therefore a 1 megapixel colour detector may detect 32768 maxima. Using a monochrome sensor increases this by a factor of 4 (131072 maxima). Each maximum gives 2 positions accurate to a small fraction of the pixel spacing. Thus, with a monochrome detector it is possible to make calculations based on 262144 numbers into 6 coordinates. It is for this reason that the present inventors consider that the system has only a very small random error (high precision). The number of maxima in the total pattern is determined by the wavelength and the pinhole spacing only. Thus the optic is easily defined to fill the detector with maxima at the preferred (average) working distance. The precision with which each maximum may be determined is limited by statistics. Thus a typical pixel on a detector is "full" when it has about $10^5$ electrons on the pixel. The variance of the number of electrons is the square root of the number of electrons or about 300. This is large relative to the readout noise (which is a factor only for underexposed regions in normal photographic applications, typically a few electrons). Now we define the peak position by fitting a curve to the (sampled) values. If the peak is centred exactly between two pixels, at the Nyquist limit the peak width is the same as the width of one pixel. Then if the peak is moved by just 1% of the pixel separation we expect 1% of the total electrons more to go into one pixel and out of the other. Thus the situation before moving is: Pixel A has 50,000 electrons. Pixel B has 50,000 electrons. After the move Pixel A has 1% of 100,000 electrons more and pixel B has 1% of the total 100,000 less. Thus after the move Pixel A has 51,000 electrons and Pixel B has 49,000. This is a difference which is 3× the variance of about 300 electrons. So it is possible to detect about a movement corresponding to about 0.3% of a pixel spacing. Typical pixel spacings are 2-20 μm, with 7 μm being a normal value. Thus, the minimum detectable motion from one peak in x-y direction in this example is about 0.3% of 7 μm=20 nm. If 262144 measurements are averaged into 6 coordinates then an improvement is obtained of the square root of (262144/6). This is therefore an improvement of about 200 times. Thus, the precision is about 0.1 nm.

(II): Calculation of Precision for Vibrometry

In some cases it is preferred to measure small, rapid changes in position, either vibrations or smooth continuous motion. Interrogating 4 small regions at the corners of the detector chip, and assuming a normal data rate (about 50 megapixels per second) then we have 1000 pixel values read out at 50 ksamples (assuming that the intensity of the pattern is sufficient and that a suitable detector is used). This gives a precision of the square root(1000/6)×20 nm, i.e. about 1.6 nm with a bandwidth of 25 kHz or 0.01 nm/Hz$^{-1/2}$.

(III): Calculation of Required Proportion of Pattern to Determine Position

The question to be addressed here is: how much of the interference pattern needs to be intercepted before the positional definition is unique (for practical purposes)? Mathematically, there are an infinite number of copies of any arbitrary sub-region of a Penrose pattern contained within an infinite Penrose pattern. However, since for practical purposes the present embodiments use a finite pattern, this mathematical proof does not apply strictly. Also, note that none of the preferred embodiments actually use a strict Penrose pattern. For vibrometry, there are being measured only changes in position. Thus this consideration is not a major issue in vibrometry. However, for absolute position measurement it is advantageous to address this issue. Firstly, it may not be necessary to rely solely on the detected pattern for absolute position measurement. Coarse indications of position may be used, e.g. simply by remembering roughly the position of the stages used, or using a non-coherent pattern projector or simple target imaging, etc. In relation to the pattern itself, it is expected that the pattern is brighter as one moves towards the central region (the whole pattern is modulated by the Airy diffraction pattern of the individual pinholes, as will be well-understood by the skilled person), so that the "envelope" of the pattern forms an indication of the direction towards the centre of the pattern. Secondly, in typical embodiments of the invention the detector intercepts a large number of maxima and/or minima. There will be few cases of all (say) 10000 maxima all being in the same relative position even in a very large diffraction pattern in more than one location in the pattern. As the skilled person will appreciate, the algorithms used to distinguish between different candidate regions in the pattern may be tuned to the nature of the pattern and the size and type of detector used. In practical systems, there will typically be required some calibration in order to assess the effect of any defects in fabrication. However, such defects (e.g. deliberately introduced) may be an advantage. In the case of a "pure" system of 5 circular pinholes, the diffraction pattern has rotational symmetry) (72°. This can eliminated by a deliberate modification of the pattern, for example the use of uniaxially oriented elliptical pinholes.

Another method for the identification of the approximate location of the detected part of the interference pattern within the whole interference pattern is to use nonlinear distortions present in the fringes resulting from each pair of pinholes when considered in turn. For a single pair of pinholes the diffraction pattern maxima trace out a set of nested hyperboloidal surfaces whose foci are the pinhole positions. Thus a measurement of the curvature of the fringes from each pair of pinholes considered in turn can be used to infer the location of the pinholes relative to the imaging plane. The diffraction patterns resulting from each pair of pinholes are distinct in the Fourier domain, and as a result may easily be isolated by spatial filtering of the image.

In a first mode of operation, the interferometer is used in a control system to hold the position of two elements to within 0.088 nm. Examples include microscopes and other analytical techniques, e.g. long-duration backscatter channelling maps.

In a second mode of operation, the interferometer is used to measure the vibration of a system around a specific position either stroboscopically (pulsed laser/detector) with 0.088 nm RMS error in 6 axes or else by monitoring the signal from a few pixels in realtime (about 5 nm RMS in single axis with very high bandwidth). This latter mode typically requires a camera chip optimised for high frame rate, for example part number MT9M413C36STM of Micron Technology, Inc., 8000 S. Federal Way, Boise, Id. 83707-0006, USA.

The fact that the pattern is substantially unambiguous (aperiodic) allows the identification of the absolute position of the detector in the diffraction field. Systematic errors in the determination of absolute precision are associated with errors in the accuracy with which the diffraction field may be defined.

The pixel spacing of the camera is lithographically defined and assumed perfect. Also thermal expansion of mountings of camera and optical element can be corrected or compensated by competent design (see below). The diffracted field represents a magnification of the positional errors associated with the optical element. For e-beam-defined apertures it is possible to position the apertures to within about 5 nm. This corresponds to a fringe shift of $\lambda/100$ for green light, or a shift in a 20 µm period fringe of 20 µm/100 (about 200 nm). Extreme care in aperture definition allows this number to be reduced to about 2 nm in the lithographic process, and therefore about 80 nm fringe accuracy. Drift in the phase shift across the optic can become a problem. For a tilt in the incident laser of $\lambda/100$ using a pentagon at 150 µm diameter, it is necessary to provide a pointing stability of about 50 µrad. This is within the capabilities of a HeNe laser, but diode and YAG lasers are typically worse by a significant margin. A solution is to use a two-layer optical element in which a spatial filter and the diffractive element are combined into a single monolithic structure. Finally, the size of the fringes scales directly with wavelength. Thus, in order to interrogate a volume of a cubic inch with a positional accuracy of 100 nm, the laser wavelength is preferably stable to about 4 ppm. This is within the capabilities of a HeNe laser. For a YAG laser [H. G. Danielmeyer, "Progress in Nd:YAG Lasers," in *Lasers*, A. K. Levine and A. J. DeMaria, eds. Marcel Dekker, New York, 4 (1976)] a drift of 0.04 $cm^{-1}K^{-1}$ is expected at the fundamental wavelength, i.e. 4 ppm $K^{-1}$, so that metrological accuracy is expected to demand the use of a gas laser for moderately large distances. Over a laboratory temperature range of ±5 K it should be noted that a YAG laser is capable of measuring distances to within 1 µm absolute in a volume of a cubic inch, or else 100 nm in a volume of 0.1 inches cubed. There is scope for trading off accuracy and cost/size.

In a third mode of operation, the interferometer measures absolute separation in 6 degrees of freedom to within 100 nm, video rate readout over one cubic inch, at moderate expense (a HeNe laser costs around $400).

In a fourth mode of operation, the interferometer can measure to 1 µm in a cubic inch at very low cost/low size (the cost of a YAG laser is about from $10).

Other volumes can be interrogated with a proportional scaling of accuracy. Very large volumes may need a better laser, then 100 nm accuracy in cubic meters is possible, subject to atmospherics.

The laser is typically selected from:

HeNe (e.g. small cavity red HeNe ca. 0.5 mW at 632.8 nm: Example Melles Griot, model 05 SRP 810-230, $430 each quantity 1). Such lasers are large and mains powered (about 18 W electrical power). They provide excellent optical quality and linewidth. They provide turnkey operation and there are no significant environmental requirements.

Doubled YAG (532 nm wavelength). Such lasers need to be doubled if photons are to be detected using a silicon sensor. Coherence length 15 mm, wavelength shift (modal) 1 µm in 1 inch (Fabry—Perot cavity shift during warm-up), and similar temperature drift in gain wavelength. These lasers are cheap (Laser pointers cost about $10, CE certified scientific modular cost around £70). Such lasers can be very small (e.g. 9 mm TO can sp3plus GDL 6001), and are DC powered (2.5 V, 1 W). They provide good optical quality, but are mechanically less good, (drift is likely to be mrad level, see below).

Diode Laser. Such lasers provide very poor thermal drift in wavelength, but are very low cost and small. Such lasers need only enough coherence length to span the optical element (typically <1 mm). The positional accuracy is typically only about 1%. Such lasers provide the basis of a very low cost vibrometer, especially in reflective mode. If the diode laser used is single mode (for example a DFB laser or VCSEL), then high accuracy, comparable to that obtained using a gas laser, may be achieved by a simple measurement of wavelength. As is discussed below, this is readily achieved at low cost by a simple modification of the system.

In the system shown in FIG. 3, there are two powered modules (laser 10 and detector 18) connected (e.g. bolted) to the two objects (not shown) whose relative position is to be determined. These modules may therefore be relatively large, and both dissipate heat. Another option (not shown) is to couple the laser to the optical element 14 using single mode fiber (pigtailed YAG or diode laser can be used here). Then the detector and the laser can be located at the same object, and thus not move relative to each other, therefore providing only one source of heat. In this case, the optical element can be made to be very small and passive. A volume of equivalent to a 5 $mm^3$ cube is typical. This allows the optical element to be mounted very close to the reference point of the moving element, providing advantages for the thermal expansion error budget, mass loading in a closed-loop system etc. Another format (not shown) is to place the camera and optic into the same housing, and to use a mirror to reflect the field into the camera. In this case the measurement is limited to separation and two tilts. Another format (not shown) is to fill a large volume (several cubic meters) with the diffraction field, and then to have a (optionally handheld) camera, with a ball (or other contact device) on the end. The position of the camera (x, y, z and three tilts) uniquely defines the position of the ball in 3 dimensions. The ball can then be used to map out the shape of a large three dimensional object. In this case there are some specific issues to address including optical hazards (note that the intensity a 5-fold field is almost uniform and may be about 1 $\mu$W cm$^2$, which is close to class 1). In this embodiment, there can be a need for a rapid centimetric positioning (in order to provide a starting point for the more precise positional measurement). This can be achieved using an ultrasonic transducer. The ball may, for example, be wielded by a robot, thereby addressing each of these issues.

Figure 4:
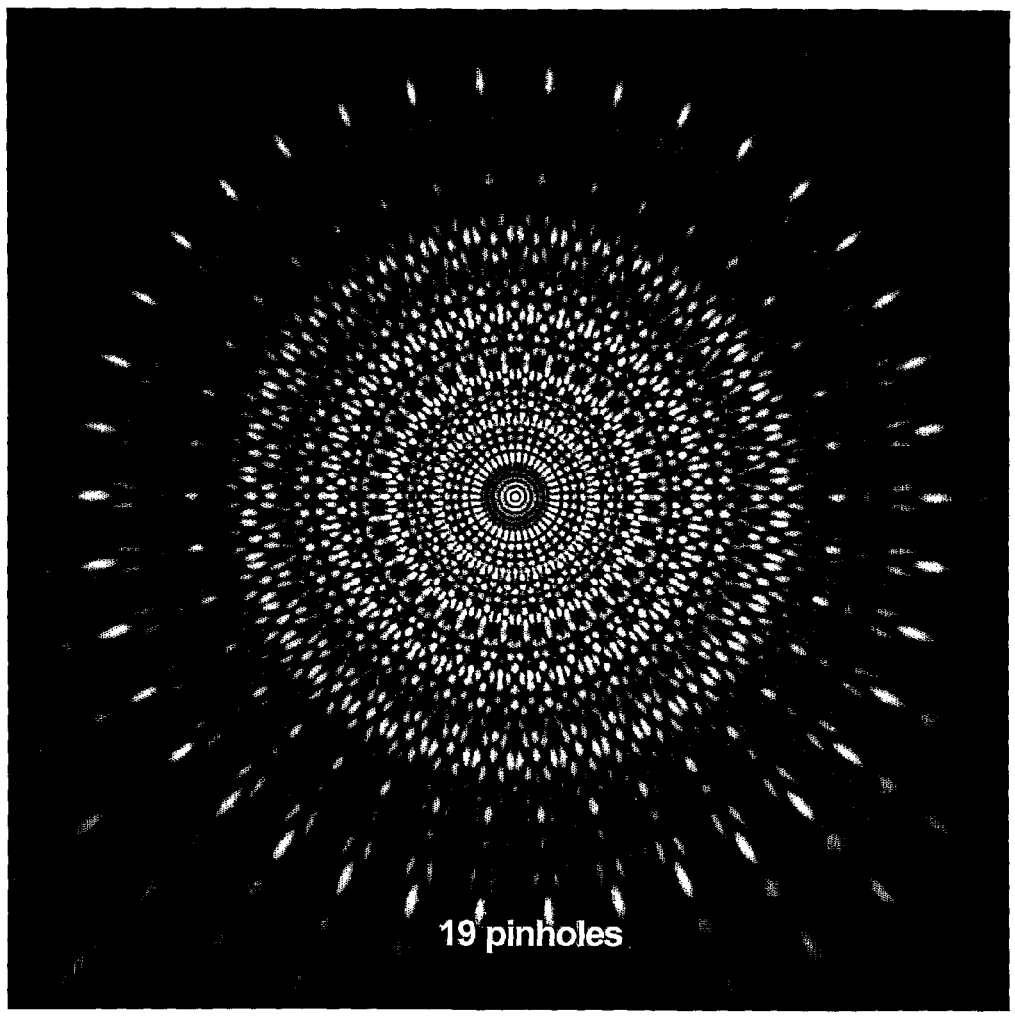
FIG. 4 shows a diffraction pattern from a ring of 19 pinholes, for use in an embodiment of the invention.

The optical element can be designed in various ways. The choice of the class of aperiodicity is quite open. A 5-fold (Penrose-like) pattern has the advantage of a dense array of maxima, which are fairly uniform over the field. Such a pattern can be generated in a straightforward manner from an array of pinholes in the shape of a regular pentagon. This improves the statistics of location and allows the use of low dynamic-range detectors, but can require a complex algorithm. Any other substantially translationally aperiodic pattern may be used, however. An example shown in FIG. 4 is the diffraction pattern from a ring of 19 pinholes. The advantage of the 19-fold array is that it has a readily identified central spot, and more obvious long-range structure.

The advantage of a pinhole array in the aperiodic field generator is that the dimensional tolerance of the structures is very easily specified and toleranced. However, in order for the diffracted field to fill a large volume, the pinholes must be small, leading to a low optical throughput. An alternative approach is to use an optical system with good throughput, such as an off-axis array of zone plates, microlenses, prisms, etc. The dimensional accuracy of highly structured optical fields, however, may be low, and there may be problems due to speckle, large intensity dynamic range etc.

Figure 5A:
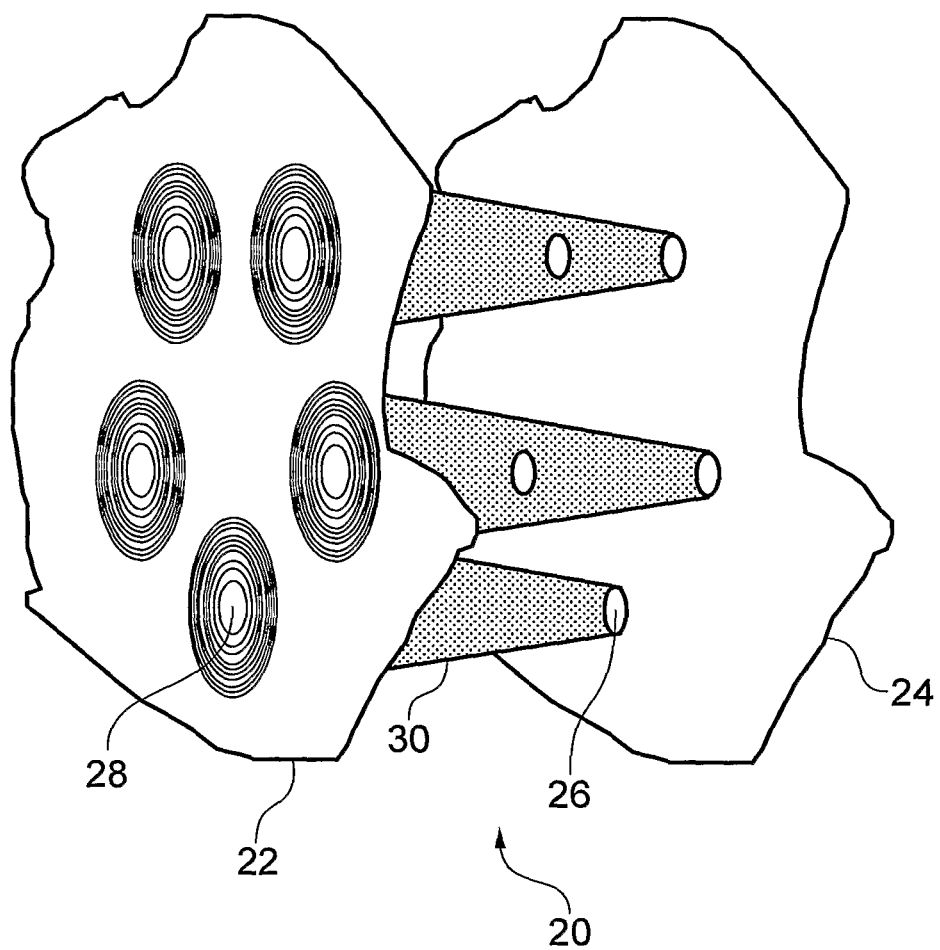
FIG. 5A shows the central part of an optical element for use in an embodiment of the invention.

In a preferred embodiment, a composite optical element is provided. An example is shown in FIG. 5A, which schematically shows the central part of an optical element 20 formed from a quartz wafer. The total area of the quartz wafer may be about 1 mm$^2$. On the reverse side of the quartz wafer is formed layer 22 of tungsten 150 nm thick. Other metals can also be used, such as aluminium. On the front side of the quartz wafer is formed another layer 24 of tungsten 150 nm thick. Pinholes 26 are formed in the front of side tungsten layer 24, at the vertices of a notional regular pentagon, using electron beam lithography. Zone plates 28 are formed in the reverse side tungsten layer 22, at the vertices of a corresponding notional regular pentagon, again using electron beam lithography. The effect of the zone plates is to focus the incident light from the reverse side towards the front side and onto the pinholes 26 (see light rays 30). This improves the efficiency of the system by using more of the incident light to generate the diffraction field.

Figure 5B:
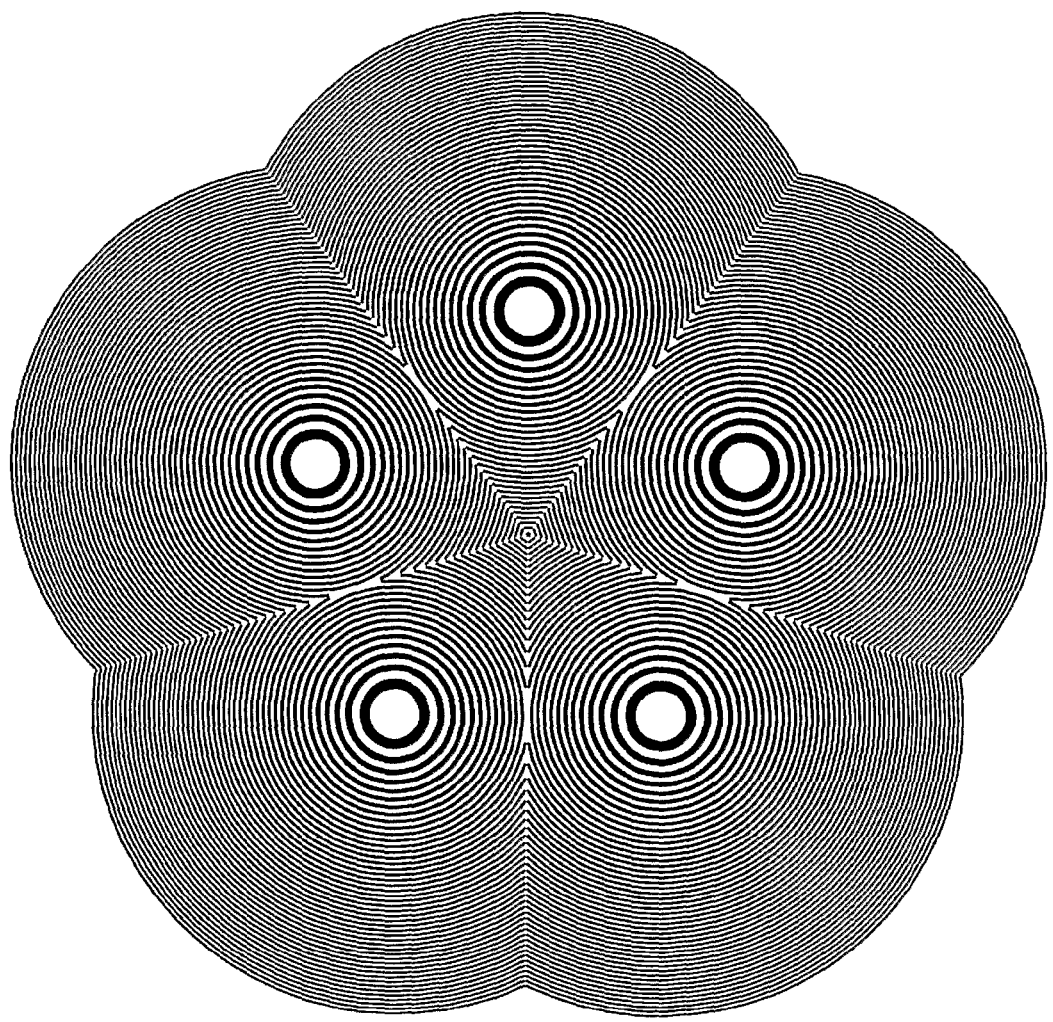
FIG. 5B shows a more detailed view of one side of the optical element.

FIG. 5B shows a more detailed view of a suitable zone plate array for use on the optical element 20. This is in effect a simple "condenser" so that the laser is focused onto the five pinholes (in this embodiment) by five zone plate lenses.

Note that a real optic may have many more "zones" than the one shown in FIG. 5B. It is also possible to calculate an optic which holographically collimates the beams, rather than defining a set of five separate zone plates—this is described in more detail below.

The use of the monolithic optical element has the advantage of retaining the precise alignment between the zone plates and the pinholes. The optical element may be incorporated onto a fiber alignment hole or a spatial filter to suppress pointing angle drift. The zone plates can be generated via software control of a suitable e-beam lithography machine. Therefore off-axis operation can be achieved if needed. Similarly, collimation from a single point source (e.g. fiber or laser diode facet) onto many pinholes can be achieved. Microlens arrays, holograms or small mirrors can be used to replace the zone plates, and prisms, gratings or mirrors can be used to form the interfering field. Note that the volume of space filled with a diffraction pattern can be modified in a straightforward manner. The angle over which the light exiting an individual pinhole is scattered is controlled by the diameter of the pinhole. The fringe spacing within the illuminated volume is controlled by the spacing between pinholes, typically the diameter of the circle enclosing the pentagonal array of pinholes in the optic as shown (26) in FIG. 5A. Thus, the diameter of the pinhole array should be smaller than the area illuminated by a ratio of the fringe spacing (e.g. about 20 $\mu$m) and half the wavelength. A 1 m cubed volume would require a pinhole array having a diameter of about 1 inch. This would typically require more significant optics to ensure accurate illumination of the array than would be needed for the illumination of a cubic inch (½ mm diameter optical element). Alternatively, the fringe spacing could be allowed to increase (using a smaller diameter optic). This would be the preferred route, since the accuracy of measurement of a large volume would in any event be compromised by atmospheric pressure variations, convection, lack of definition of the laser wavelength, etc. The error budget is very flexible and allows many trade-offs to be made as regards accuracy, precision and cost.

As an example, the total power required to "fill" a VGA CCD to 300,000 electrons is 1 $\mu$W at 30 fps, so the optical efficiency of the optical element needs only to be 0.1%.

Blurred zone plates may be used to improve alignment tolerance. Additionally or alternatively, it is possible to power cycle the laser to reduce heat load and/or enable stroboscopy.

Additionally, it is possible to utilise a further optic between the laser output and the generator optic. Such a further optic preferably includes a further zone plate, allowing more tolerance in the alignment of the laser output with the generator optic shown in FIG. 5A.

The detector is typically monochrome. The use of a CCD as the detector may be expected to give more uniform sensitivity per pixel, which may give slightly lower noise in the measured position (although this noise is typically very small anyway). The detector requires screening from external light sources using (e.g.) a bellows. It is preferred that the detector should not incorporate a lens, as the geometric precision of the positioning of the detector pixels is crucial to the operation of the system. (However, as discussed below, other embodiments may use an etalon for additional functionality. Still further, other embodiments may use one or more lenses for specific functionality.) If a custom CMOS camera is used, then it may be possible to re-configure the camera to interrogate the intensity around a few optical maxima at much higher data rate. This allows wide bandwidth vibrations to be measured, as discussed above. The precision of the measurement improves as the pixel spacing is reduced, but the accuracy is almost totally determined by the accuracy with which the aperiodic field is generated. Sensitivity is not a significant problem, but the data rate for positional measurement is equal to the camera frame rate, so the use of a fast camera can be advantageous.

In the processing of the data received from the detector, the number of calculations required is typically not significantly greater than those used in image compression (e.g. JPEG). In the case of a 5-fold pinhole pattern, a typical processing algorithm is hierarchical, starting with the identification of all maxima in the field, the identifying (on the basis of distance to nearest neighbour maxima) the location of the various motifs present in the image. Next mapping the motif distribution onto a calculated field distribution to identify the position of the camera in the field and finally identifying the scale and geometric distortions of the pattern which correspond to tilt and pinhole-to-camera separation. As the output data rate can be low (6 numbers, 30× per second and status flags), the interface can use, for example, USB and text format for position readout, as the skilled person will readily appreciate.

An alternative method for the determination of the position of the pattern makes use of 2-dimensional Fourier transforms (2-dFT) to achieve processing substantially in the spatial frequency domain. Such an algorithm starts by measuring the spatial frequencies locally present in the pattern by performing 2-dFTs on small patches of the pattern, for example in the centre and corners of the pattern. Next the pattern is distorted in real space to reverse the geometric effects of tilt between optic and detector. The measurement of local frequency can be very accurately accomplished by means of an interpolation algorithm and the choice of suitable windowing functions. See, for example, "Optimal interpolating windowed discrete Fourier transform algorithms for harmonic analysis in power systems" H. Xue and R. Yang, IEEE Proc. Gener. Transm. Distrib. Vol. 150 No. 5 p. 583-587 (2003). Such a process is accomplished in an iterative fashion until the spatial frequencies present in the pattern become substantially uniform. The distortion required is then a measure of tilt between optic and detector. Next a 2-dFT can be performed on the whole image, again using an appropriately windowed transform.

The location of the maximum spatial frequencies then gives a direct measure of distance between sensor and optic and the rotation of the two about the optical axis. The phases of the measured transform are determined and the translation required such that all phases would have been the zero value determined. This translation distance represents the motion of the components in the plane perpendicular to the optic axis.

This method also allows the measurement of wavelength using an etalon to cover the whole detector (unlike the half-covered detector discussed later). In this case, using an etalon, multiple passes of light appear as a number of replicas of the transform of the pattern, corresponding to distances spaced by double the etalon optical thickness. Such an etalon permits continuous wavelength measurement during normal operation of the interferometer. This technique for wavelength measurement is discussed in more detail below.

The system may be calibrated against an interferometer of known precision as a check on the overall system accuracy.

Figure 6:
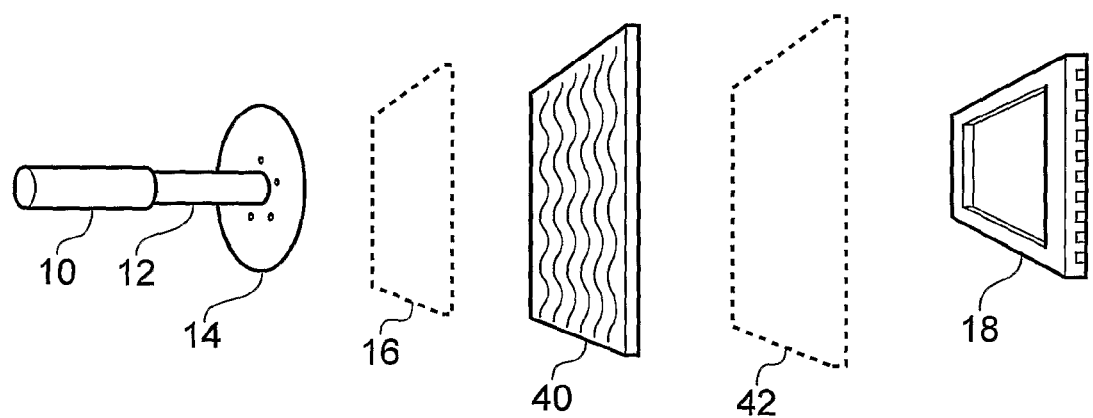
FIG. 6 shows a schematic view of a modified system compared with FIG. 3.

The system may be configured to act as a system for the quantitative measurement of variations in the differential phase of an optical wavefront over an extended area (e.g. similar to the qualitative results obtained from Schlieren systems). This is illustrated in FIG. 6, which shows a modified system compared with FIG. 3. Similar features are given similar reference numbers and are not described again.

In FIG. 6 (schematically similar to FIG. 3A), a phase object 40 is interposed between the generator (10, 12, 14) and the detector 18, the pattern sampled at plane 42 after passing through the phase object 40 is distorted, compared with the pristine pattern that would be seen at plane 16. Thus if the baseline distortions associated with position are removed (using software), any remaining distortions of the pattern will reflect local changes in refractive index in the space interrogated. Plotting these distortions (the "residuals" from the position measurement algorithm) gives a direct, quantitative map of index, much like a Schlerein image or a map obtained using a Mach-Zehnder interferometer. A key advantage here is that the "alignment" of the system is performed in software. Hence, instead of carefully aligning mirrors, knife edges, etc., all that is required is to fix the position of the generator and detector and then start to measure immediately. This lack of an alignment requirement, coupled with quantitative measurement of arbitrarily strongly curved wavefronts is very attractive. Examples of applications include ballistics (using pulsed lasers), "mirage effect" measurements of chemical or thermal processes, imaging and detection of transparent microscopic objects (such as plankton), centration of cemented optical systems (such as aspheric lenses), evolution of flame fronts and combustion in internal combustion engines, etc. Since the systems can be manufactured at low cost and since the "gearing" effect of the optical element allows the use of low coherence (short pulse) sources, the systems will be well-suited to the acquisition of large numbers of measurements around an object for tomographic measurements, or else extremely high speed video. One difficulty with this phase measurement system is that the size of the interrogated region is intrinsically less than the size of the image sensor. Thus this application (unlike the positioning application) will require the use of large-format sensors, which are expensive, but becoming cheaper.

In the differential phase measurement system of FIG. 6, the maxima of the interference pattern form a series of (hyperbolic) paths through the volume between the generator and the detector. When the medium 40 has (spatially) variable refractive index, then the phase relationship between the pinholes of the optical element 14 will be differentially modulated, distorting the curves defining the "paths" of the intensity maxima positions. Thus, if a planar glass sheet is placed between optical element 14 and detector 18, with the glass sheet half covering the detector area, then the diffraction pattern in the area covered by the glass will appear to be characteristic of a pattern, for example, closer to the detector than where the glass is not present. This is described below in more detail with reference to FIGS. 20a and 20b. Prisms will appear to provide a tilt in the detector plane. Lenses will result in a local change in curvature. Thus a small gradient in index will be readily measured as a "residual" map of displacement of maximum positions after the bulk of the pattern is fitted to a simple 6-axis orientation of detector to pinhole array.

Since the system can be composed of inexpensive, compact components, a tomographic phase imaging system is readily achieved by pointing a number of sources at a single detector (or duplicating a number of complete systems to pan around an object). The spatial resolution approximates to the spatial frequencies present in the pattern. Time resolution for a moving object is easily achieved by the use of pulsed lasers. For example, Q-switched YAG lasers are relatively cheap and the reduced coherence length requirements of the system allows the use of very short pulse length systems; e.g. a 1 ps laser has a coherence length of some 500 wavelengths, approximately the maximum phase difference used in the discussion of the "cubic inch" interferometer system, above. Thus a series of systems may be arranged around the interrogated volume to form a complete 3-dimensional image of the index variation. An example application of such a system is a 1 inch diameter pipe through which water is pumped at a rate of 25 cubic inches per second. The plankton present in the pipe may be detected (transparent phase objects) and imaged (stroboscopic exposure) with a resolution approximating the fringe spacing. This requires the use of large detectors. "Full frame" detectors [http://www.canon.com/technology/canon_tech/explanation/cmos.html and http://www.kodak.com/US/en/dpq/site/SENSORS/name/ISSProductFamiliesRoot_product] are available at the time of writing at reasonable cost (about £1000) which have a size of 36 mm×24 mm (35 mm film equivalent) or larger. Note that such sensors tend to be slow (9 fps for the Nikon D3, which is state of the art at the time of writing), so that the data rate (not the time resolution, which is defined by the laser) will be constrained. Other applications are investigation of the air pressure close to the surface of a (convex) aerofoil, the evolution of reaction products above a surface (electrochemical reactions, dissolution etc), flame/combustion studies (especially in internal combustion engines), ballistics etc. Temperature and concentration gradients in fluids (process control, mixing) and micro refractometry. Inexpensive (even disposable, which is useful in ballistics applications), compact, precise and quantitative substitutes are thereby provided for expensive interferometers and Schlerein cameras.

The detection of a refractive index distortion relies on the fact that the pattern that would be detected in the absence of such distortion is known or calculable. Thus local changes in refractive index within the interrogated volume result in a distortion of the pattern which is distinguishable from that arising due to gross relative motion of the detector relative to the generator. Typically, the intensity pattern generator is of relatively small spatial extent (the pixel spacing of the detector is typically greater than or much greater than the wavelength of the light), there is typically intrinsically a magnification of the interrogated volume as projected onto the detector. Thus the detector should normally be at least as big as the projection of the interrogated volume, otherwise not all of the "interrogated" volume will be interrogated. For example, a 1 inch square detector cannot be used to measure local refractive index changes in a volume which is projected at the detector as an area larger than 1 inch square.

Another potential application is in the imaging of differential expansion over a distributed reflective object. In this case the system is pointed at an object which is structured with a number of "patches". The interferometer is then be used to measure the change in relative height of the patches in response to a measurand. For example, a homogenous material with a surface which has different heights will expand as a function of temperature, permitting measurement of temperature in challenging environments. The method may be extended. For example, the expansion of a material which is sensitive to humidity allows the measurement of humidity. Chemical binding to functionalised patches (porous or surface functionalised) allows the detection of particular chemicals, such as pollutants, biochemicals etc. A number of patches (functionalised and reference) may be applied to a surface and several measurands detected at once. Transparent patches deposited onto a transparent substrate allow measurement from the back of the sensor in a "window" configuration for use in challenging environments.

The preferred system is typically compatible with sources having low temporal coherence, especially short pulse lasers. In particular, the diffractive optical element may be optimised to allow the interferometric interrogation of a volume much larger than the coherence length of the source used. This is important for the investigation of fast processes, such as ballistics.

As the skilled person will appreciate, interferometry is the gold standard of position measurement and the preferred embodiments of the present invention provide greater accuracy and precision than existing systems. The inventors note that embodiments of the present invention can measure all 6 axes with one system and that there is no existing technology that has this capability. The ability of the system to measure absolute position in an interferometric context is a major advantage, eliminating the need for precision definition of a "zero" point on starting up a system. The preferred embodiments can be built into existing systems (requiring simple external packaging changes only). The systems can be manufactured at relatively low cost compared with competing technologies, and the most basic system envisaged herein has precision comparable to the best present technology and has high accuracy. Furthermore, the present invention may have the ability to make quantitative phase measurements over a large volume using a low temporal coherence source, such as a ps or fs laser system. The preferred embodiments of the invention provide turnkey position measurement. They can operate on a noncontact basis and are environmentally flexible.

In a specific embodiment, the system is used within a controller such as a joystick. Typically, if redundancy is required in measurement of a joystick (e.g. in an aeroplane), multiple sensors are typically put on the joystick. Since such sensors measure a single degree of freedom, they are typically paralleled on the same axis/bearing. The interferometer system of the embodiment, in contrast, can measure the total displacement of the joystick from top to base in one go. Since the measurement is independent of the bearing system used to realise and constrain the motion, redundant measurements are obtained by locating more interferometers anywhere on the joystick.

The interrogation of the data from the detector is accomplished using suitable software. In essence, this step is a data-fitting step—fitting the detected image to a calculated "map" of the diffraction pattern. There are many possible ways to achieve this. In particular, preferred embodiments make use of the low spatial frequency terms, such as global brightness variation/Airy function or the curvature of the fringes which make up the pattern in order to guide an initial positional estimate. Motif recognition can be used, and or a binned peak separation map. Alternatively, a "brute force" least squares correlation may be used.

In one embodiment, the position of the detected image within the overall diffraction pattern is determined using software developed for detecting the alignment of wafers in electron beam lithographic processes.

The fabrication of all functional semiconductor devices requires multiple lithographic exposures, each of which is followed by some process that alters the areas of the sample as defined by that exposure. It is critical that the structures defined in these different lithographic exposures are positioned accurately with respect to each other. A simplistic example of this would be in the fabrication of a field effect transistor where the drain and source are patterned during the first lithographic exposure and a subsequent exposure is used to define the gate of the transistor which must be accurately positioned between the already defined drain and source regions to produce a working device. This process of positioning a pattern during exposure so that it is matched to some existing features is known as alignment.

As devices become increasingly smaller and more densely packed, the tolerances allowable on all stages of nanofabrication consequently become more stringent. Alignment being one of the fundamental stages of device fabrication is no different and therefore improvements to the current method are of profound interest to all fields of semiconductor fabrication.

Alignment can be thought of as relating the design to be exposed to the layers already patterned on the wafer. In general terms, it is convenient to think of positions on each of the two layers to be aligned as being described by different co-ordinate systems. The design has an idealised, undistorted co-ordinate grid which is what we expect to observe on the wafer after exposure. However, due to the distortions of the wafer and just the rotational and translational errors associated with mounting the sample, this idealised coordinate system, when measured on the sample's surface is offset, rotated, stretched and skewed and subjected to more complex keystone, barrel and pin cushion distortions. The process of alignment can then be thought of as finding a way to mathematically transform from one co-ordinate frame to the other, so that when subsequent layers of the design are exposed, the idealised co-ordinate system of the design is distorted to exactly match the distortion of the existing exposed layers.

As the skilled person will appreciate, rotation and translation of the imaging plane (detector) in the diffraction field is susceptible to a similar analysis, as are distortions brought about by refractive index variations in the interrogated volume.

Mathematically this transformation can be achieved by the use of a projective transform to convert the ideal co-ordinates on the design to match the actual positions as measured on the wafer. The general expressions for a projective transform from the (x, y) co-ordinate frame of the design to the (X, Y) co-ordinate frame on the sample are given by Equations 1 and 2 below, with the relationship between the coefficients and physical distortions as detailed in Table 2.

$$X = \frac{a + cx + ey}{1 + gx + hy} \quad (1)$$

$$Y = \frac{b + dy + fx}{1 + gx + hy} \quad (2)$$

TABLE 2

Details of coefficients

| Coefficient | Distortion |
|---|---|
| a, b | X, Y offset |
| c, d | X, Y scale |
| e, f | X, Y rotation (shear) |
| g, h | X, Y keystone |

Figure 8:
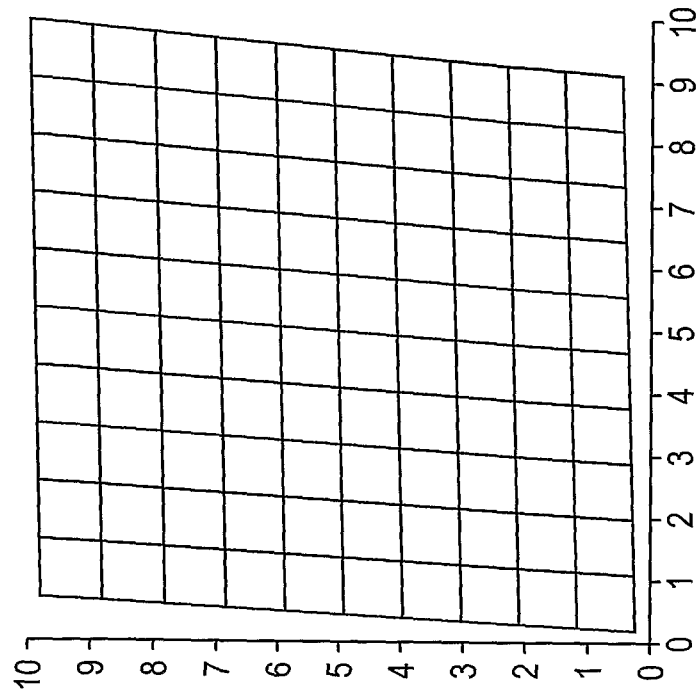
FIGS. 7 and 8 show how an idealised co-ordinate grid (FIG. 7) can be distorted by a projective transform to give a misshapen co-ordinate grid (FIG. 8).
Figure 7:

An example of how the projective transform affects a co-ordinate system is shown in FIGS. 7 and 8 which show how an idealised co-ordinate grid, FIG. 7, can be distorted by a projective transform to give a misshapen co-ordinate grid, FIG. 8.

To be able to calculate the eight coefficients for a projective transform at least four references points must be used. Measuring the positions of these four points on the wafer and comparing them to their expected positions, which we know from the design, gives enough information to fully calculate the projective transform coefficients. In practice for alignment in the context of electron beam lithography this is done by designing and fabricating markers on the first level of a pattern to be aligned. Currently markers are simple geometric shapes such as squares, octagons or crosses, and can either be formed by depositing a material with a different atomic number or by creating topographical features such as etched pits into or raised regions on top of the substrate. The markers can then be detected by scanning the electron beam across and examining the backscattered electron signal as a function of position.

While the current alignment methods have provided sufficiently accurate alignment for a wide range of devices there are several facets that limit the accuracy which is ultimately attainable when using this process of alignment. A fundamental problem with this technique is that only the edges of the marks contain useful information about their position, and hence only the edges of the marks contribute to the alignment. Therefore the accuracy is directly related to how well the edges of the pattern have been defined during fabrication and is susceptible to a host of errors. Furthermore, to find the edges, more than the whole area of the mark must be interrogated, yet only a very small region around each mark edge contains any useable information relating to the position of the marker. The interrogation of such a large area necessarily leads to the exposure of this area of resist and hence the marker becomes exposed to whatever the subsequent process step requires. This almost inevitably results in the marker being destroyed or damaged to beyond a usable state. This leads to another fundamental inaccuracy in the current alignment method: when multi-stage alignments are required, different alignment marks must be used for each alignment and this introduces a further source of errors into the process.

In order to address these problems, Holburn et al. [Holburn, D. M., Jones, G. A. C. and Ahmed, H. (1981) "A pattern-recognition technique using sequences of marks for registration in electron-beam lithography, *Journal of Vacuum Science & Technology*, 19(4), pp. 1229-1233] exploited techniques from the image registration and pattern recognition fields and used an alignment algorithm based on the process of correlation.

Correlation, in image processing terms, is a process that measures the similarity between two images. As such, it can be used to locate a marker by comparing a reference image of an ideal marker within an image of the marker as exposed on the wafer with the associated distortions present. One of the main advantages of using a correlation method is that information is retrieved from the whole of the interrogated area since the whole image is used to locate the marker.

Mathematically, correlation is closely related to convolution as can be seen from equation 3, the correlation integral for two functions f(r) and g(r), where "*" denotes correlation.

$$f(\vec{r}) * g(\vec{r}) = \int f(\vec{s}) g(\vec{r} + \vec{s}) d\vec{s} \quad (3)$$

Convolution is often expressed in a more convenient form using Fourier transforms and a similar relationship exists for correlation, as shown in Equation 4, where F(k) and G(k) denote the Fourier transforms of functions f(r) and g(r) respectively and F{ }, where "$\mathfrak{F}$" denotes a Fourier transform.

$$f(\hat{r})*g(\hat{r}) = \mathfrak{F}\{F(\hat{k})\overline{G}(\hat{k})\} \quad (4)$$

From Equation 4, it can be seen that the correlation of two functions in the spatial domain is equal to the multiplication of their Fourier transforms in reciprocal space. The complex conjugation, denoted by the over-bar, of one of the functions in the Fourier domain is due to the sign change in the correlation integral with respect to the convolution integral.

The autocorrelation of a function, which is the correlation of a function with itself, has an important relationship to the power spectral density of a function. The Wiener-Khintchine theorem states that the autocorrelation and the power spectral density of a function are a Fourier transform pair [Koopmans, L. H. (1974). *The Spectral Analysis of Time Series*, chapter 2, number 22 in Probability and Mathematical Statistics—A Series of Monographs and Textbooks, Academic Press, New York and London, pp. 33-34]. This is demonstrated if we consider how Equation 4 changes in the case of correlating two equal functions.

$$f(\hat{r})*f(\hat{r}) = \mathfrak{F}\{F(\hat{k})\overline{F}(\hat{k})\} = \mathfrak{F}\{|F(\hat{k})|^2\} \quad (5)$$

Turning now to the graphical interpretation of correlation, the practical outcome from these mathematical properties means that correlation provides a measure of similarity between two functions as one is displaced relative to the other. Therefore, using two dimensional functions (or images) and correlating them, a measure of the relative offset, between the two images, which gives the greatest degree of similarity can be obtained. As such, it can be used to locate a reference pattern within another image, which may be noisy, imperfect or distorted in some way.

Figure 9:
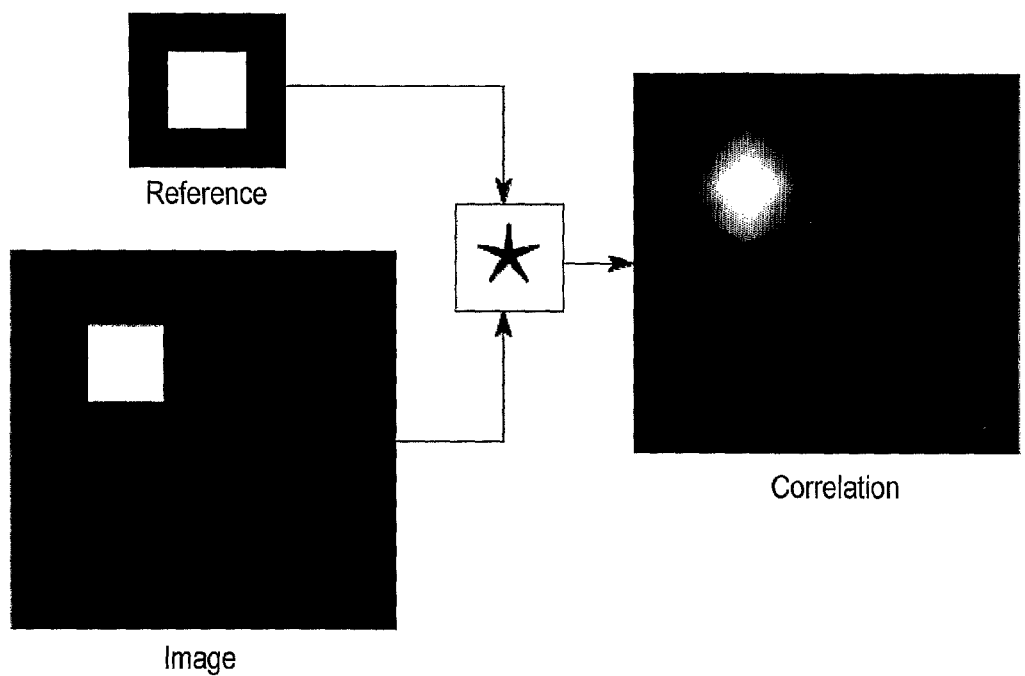
FIG. 9 shows how a simple square reference pattern can be located within a larger image, by finding the point with the greatest brightness in the correlation which corresponds to the offset with the largest value for the similarity.

Schematically this is illustrated in FIG. 9, which shows how a simple square reference pattern can be located within a larger image, by finding the point with the greatest brightness in the correlation which corresponds to the offset with the largest value for the similarity.

Using correlation to perform alignments removes the limitations of using simple geometric shapes as markers, since locating the markers no longer relies on a method of edge detection. This opens up the possibility of investigating the use of more sophisticated patterns as markers, and indeed this is one of the most important factors affecting the accuracy of correlation based alignment.

To facilitate the evaluation of a pattern, or more importantly its autocorrelation, a figure of merit has been derived. For alignment, the most necessary feature is a sharply peaked autocorrelation and there are several so-called peak sharpness measures that aim to give an indication of how this relates between different autocorrelations. The most applicable of the peak sharpness measures is the peak-to-correlation energy ratio or PCE. This relates the energy contained in the central peak of the correlation to the total energy contained in the correlation plane. As such, it gives a direct measure of the sharpness of the central peak of an autocorrelation: a sharp peak will contain a larger proportion of the total energy within the central peak than a more widely spread out peak. Mathematically it is given by Equation 6, where A(x, y) is a mathematical representation of the correlation and (0, 0) is the location of its maximum.

$$PCE = \frac{|A(0,0)|^2}{\iint_{-\infty}^{\infty}|A(x,y)|^2\,dx\,dy} \quad (6)$$

The best alignment would result from a sharply peaked autocorrelation function that, in the best-case scenario, could be approximated by a 2D delta function. This gives a PCE close to 1 (equal to 1 for a delta function) for the autocorrelation. Using the Wiener-Khintchine theorem, Equation 5 which relates the autocorrelation to the Fourier transform of the power spectral density, leads to possible patterns with good autocorrelation properties. The Fourier transform of a 2D delta function is a constant value, which, using the Wiener-Khintchine theorem, implies that the power spectral density of the ideal marker would also have a flat profile. In an image this implies that every possible separation between pixels is represented a constant number of times, ideally only once, in the image. That is a perfectly aperiodic pattern, with a good sampling of frequencies throughout its extent.

Figure 11:
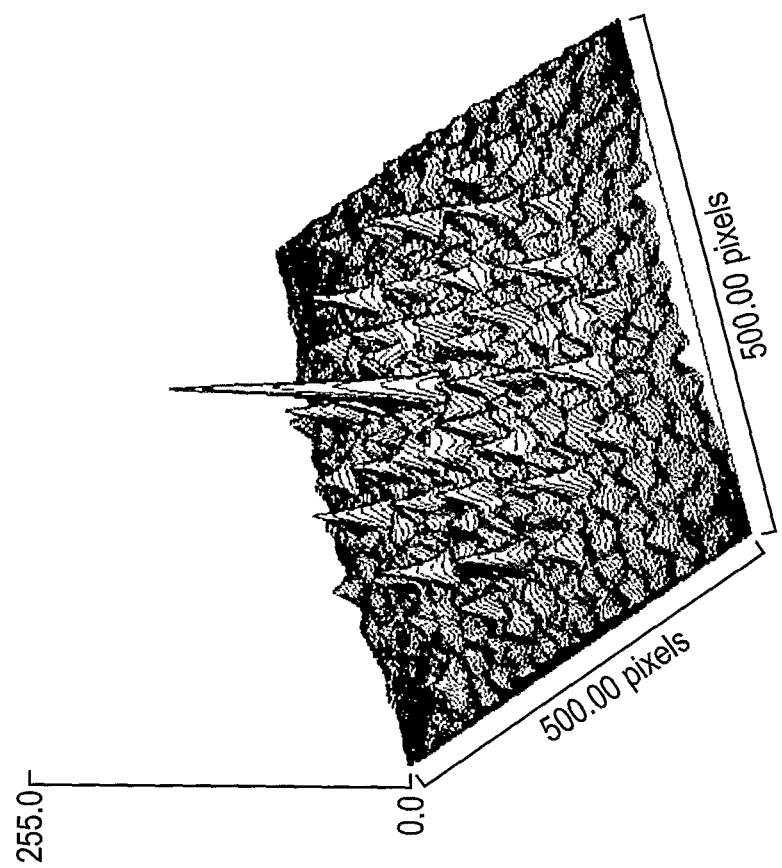
FIG. 11 shows the autocorrelation of the pattern of FIG. 10.
Figure 10:
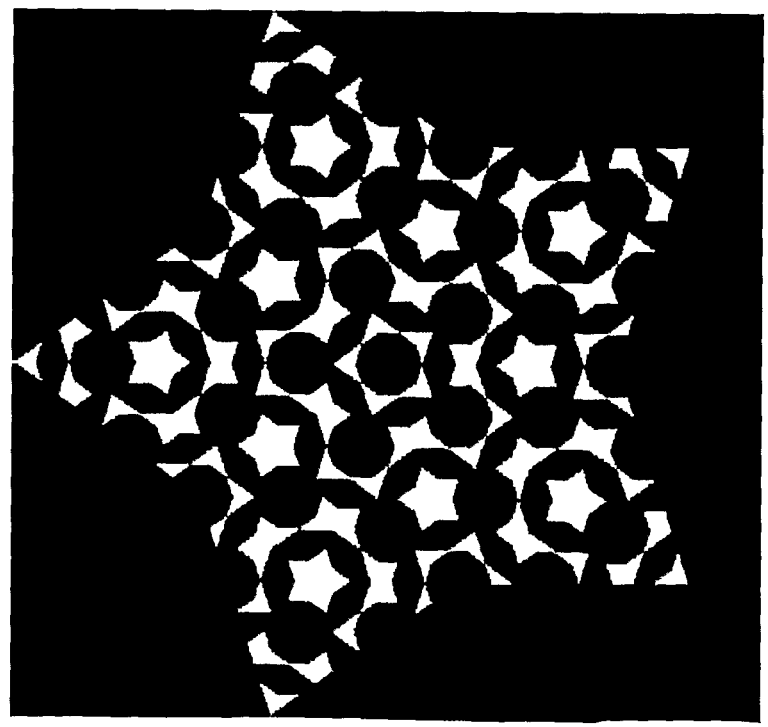
FIG. 10 shows an example pattern of Penrose tiling.

It is found by the present inventors that the diffraction patterns discussed above have good autocorrelation properties. Consider again the example of Penrose tiling. These tilings are based on only two fundamental tiles that can be used to perfectly cover an infinite plane with an infinite period. This means that any part of a tiling will never reappear within the pattern no matter how big a translational shift is introduced. There are an infinite number of possible patterns to choose from and an example pattern is shown in FIG. 10, along with its autocorrelation, shown in FIG. 11.

Figure 12:
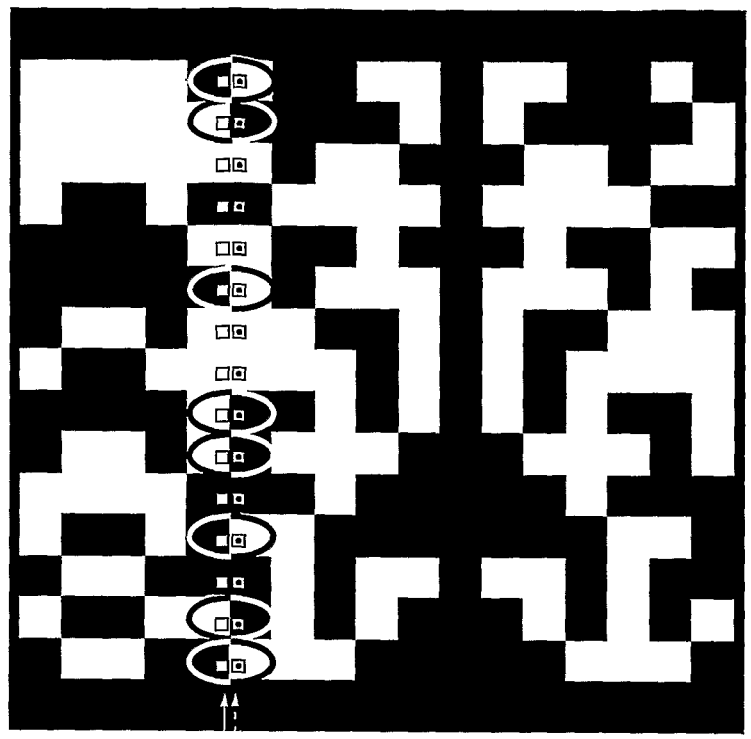
FIG. 12 shows sampling of a pseudo-random noise sequence (PN) array.
Figure 13:
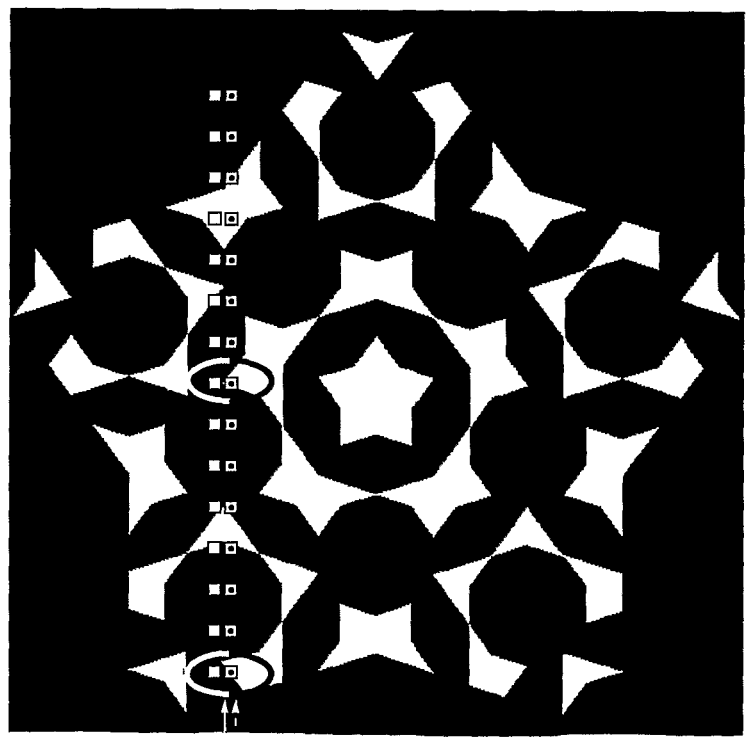
FIG. 13 shows sampling of a Penrose pattern.

An interesting feature of Penrose patterns stems from the fact that their general shape cannot be easily described by an orthogonal grid. This is because Penrose tilings are not formed from square nor rectangular elements but rather are formed from rhombic or triangular shaped elements, as can be seen in FIG. 13. For comparison, FIG. 12 shows a pseudo-random noise sequence (PN) array. This feature provides an advantage when we consider what happens when the pattern is interrogated, or sampled at regular points on an orthogonal grid space. If we assume that the grid has a spacing between points which is similar to the periodicity of the pattern then as the grid is shifted by small amounts relative to the pattern it is desirable that the results of the sampling are not greatly affected.

To illustrate this one vertical line of a possible sampling grid has been drawn on the images of FIGS. 12 and 13 as a series of dots [shown as unfilled square dots, left side of the column of dots]. A second vertical line of dots represents the same line in the sampling grid after a small shift in location [shown as partly filled square dots, right side of the column of dots]. The ellipses highlight the points where the small shift in location produces a discrepancy in the sampled pattern and are much worse for the square base pseudo-random noise sequence pattern, with more than half of the sampling points all changing at once, whereas only a small fraction of the sampling points change given the same shift on the Penrose pattern.

To gain some practical insights into how well the correlation base alignment can measure small positional variations several experiments to measure the small drift in stage position over time have been performed. To do this the system is set-up to be positioned on an area of a Penrose marker, and then images of the region were regularly captured over a period of about two hours. As each image was obtained, the correlation program produced the correlation of that image with the first image taken, and from that calculated the relative displacements or drift of the stage in both the x and y directions. These measurements of the stage drift were compared with those measured by the conventional alignment or mark locate routines performed at the same time as each of the correlations. The graphs of FIGS. 14A and B show the relation between the drift in the x and y directions as measured using the two methods.

Figure 14A:
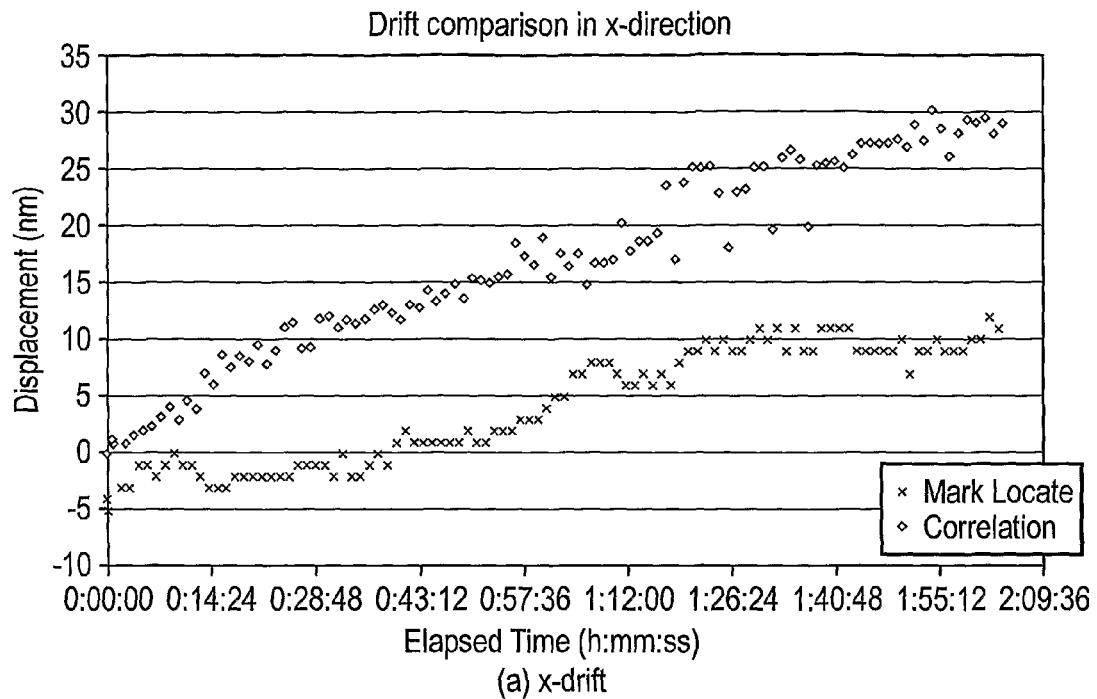
FIGS. 14A and 14B show a comparison between the x (FIG. 14A) and y (FIG. 14A) drift as measured by mark locate and correlation based methods.
Figure 14B:
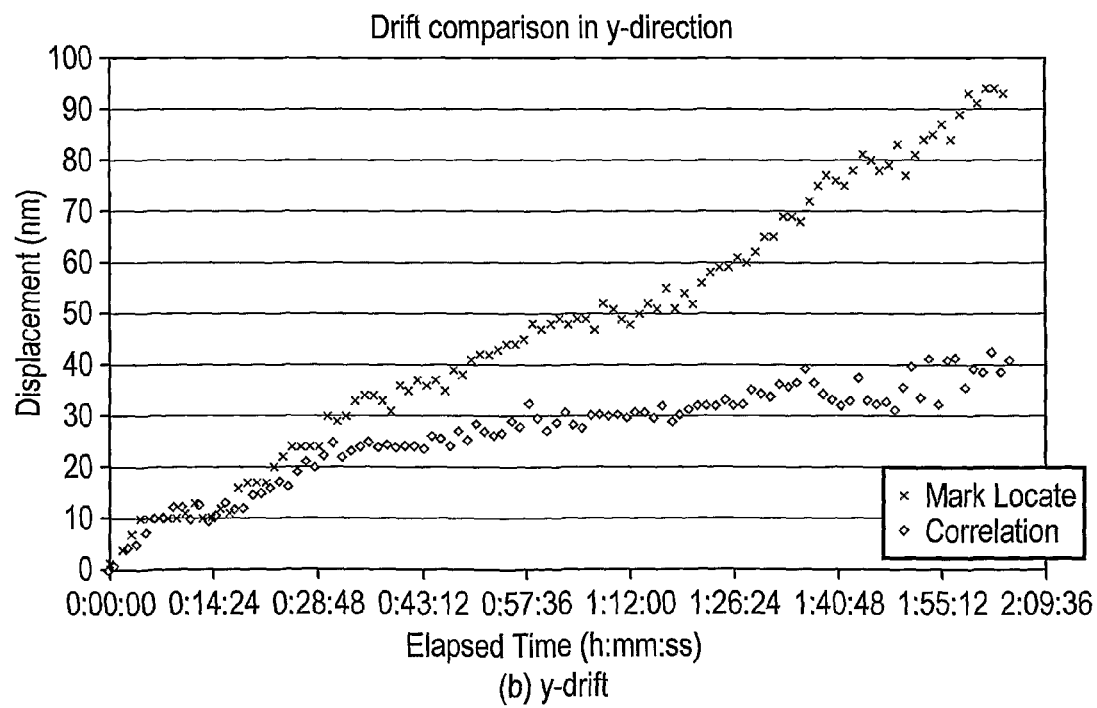

FIGS. 14A and B give a good indication that the correlation method can provide a measure of small displacements. However, it is hard to interpret how accurate these measurements are from these graphs. It is possible however to note the quantisation of the results from the mark locate algorithm particularly from the x-drift graph (FIG. 14A), and it is possible to see why this may limit the accuracy attainable from the conventional algorithm.

An estimation of the accuracy of the correlation based alignment was obtained by least squares fitting a $5^{th}$ order polynomial to the data and then measuring the deviation of the points from this curve. The standard deviation of the measured points gave a value of 0.5 nm in the x-direction and 1.1 nm in the y-direction, suggesting an initial estimate on the accuracy attainable.

To give a more direct measure of the possible accuracy of the correlation method a similar experimental set-up was used. However two Penrose patterns were used and two correlations were performed on each iteration. This allows systematic errors common to both correlations to be eliminated, in particular it allowed the stage drift to be removed from the data. This leaves a measure of inaccuracies of the alignment process, including the inaccuracies of the algorithm used. The graphs of FIGS. 15A and B show the results from such an experiment and compare the variation of the built-in mark locate routine to that of the correlation algorithm for both the x- and the y-directions.

Figure 15A:
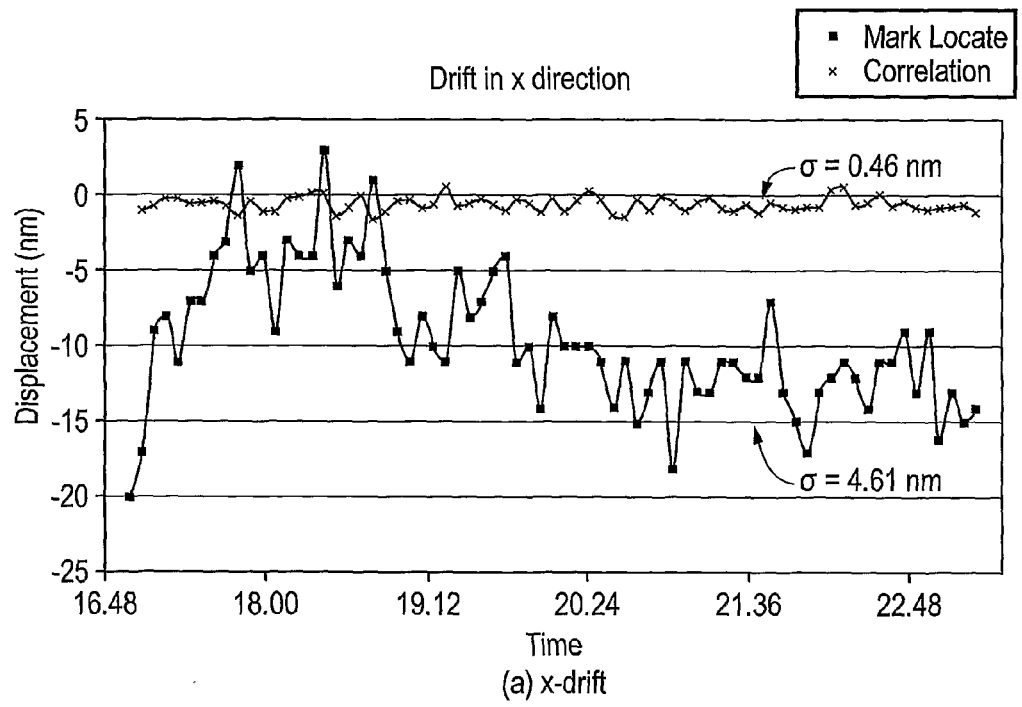
FIGS. 15A and 15B show a comparison between the x (FIG. 15A) and y (FIG. 15B) drift variations of the mark locate and correlation based methods.
Figure 15B:
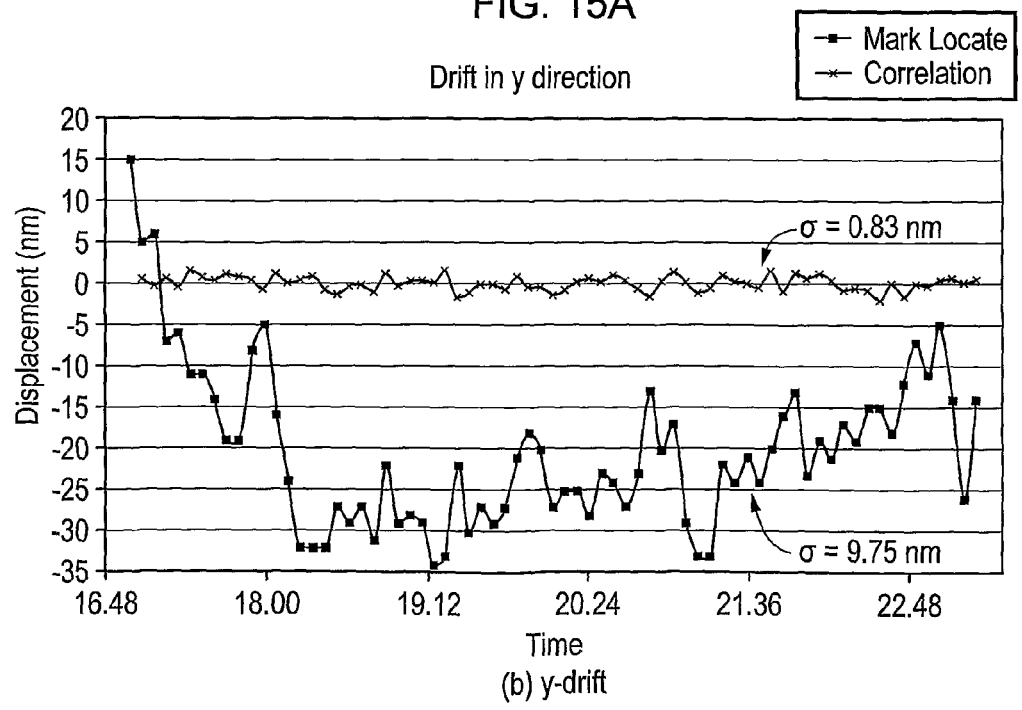

The σ values quoted on the graphs of FIGS. 15A and B show the standard deviation of each of the curves and since the curves only vary with errors in the algorithm this give a direct measure of the attainable accuracy of the correlation and mark locate routines. There is a marked difference between the x and the y-directions, with the values in the y-direction generally being worse. This can most likely be attributed to the presence of about 3 nm of wobble on the beam in this direction. In comparison with the mark locate results the correlation algorithm produces around ten times better accuracy, 0.46 nm as opposed to 4.6 nm in the x-direction, and 0.83 nm as opposed to 9.8 nm in the y-direction. These figures show the possibility of sub-nm alignment using a correlation based method.

The skilled person can therefore implement a suitable correlation-based processing technique in order to identify the position of a captured image within the diffraction pattern. Similar techniques allow the identification of distortions in the captured image compared with the non-distorted diffraction pattern.

Figure 16:
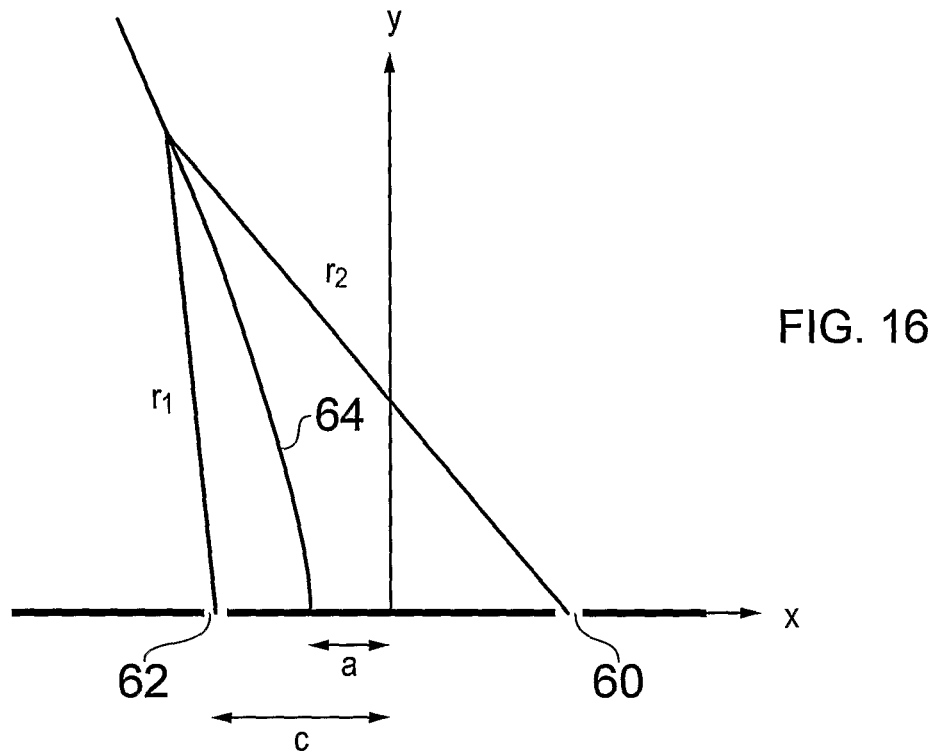
FIGS. 16 and 17 show schematic views of the "Young's slits" experiment.

It is useful to consider how the spacing of the maxima and minima (fringes) in the diffraction pattern varies with distance from the pattern generator. FIG. 16 shows a schematic view of the well-known "Young's slits" experiment. The fringes arise due to constructive interference between light from two or more apertures (slits 60, 62). As a consequence, the relationship between the spacing between any two maxima as a function of distance can be calculated. Considering only two sources (slits 60, 62) as in FIG. 16, when light of wavelength λ illuminates two apertures spaced by distance b, then the illumination on a screen at perpendicular distance y from the slits is bright if the distance from one slit to the screen is the same as that from the other slit, plus or minus a whole number of wavelengths. Thus $r_1-r_2=n\lambda$. The path over which this relationship holds true is a hyperbola, as shown by the curved line 64 in FIG. 16, in view of the fundamental definition of a hyperbola.

Considering the path differences at y=0, we have that $r_1-r_2=n\lambda=2a$. Substituting in for the values of $r_1$ and $r_2$:

$$\sqrt{(x-c)^2+y^2} - \sqrt{(x+c)^2+y^2} = 2a$$

$$\Rightarrow \sqrt{(x-c)^2+y^2} = 2a + \sqrt{(x+c)^2+y^2}$$

$$\therefore x^2-2xc+c^2+y^2 = \frac{4a^2+4a\sqrt{(x+c)^2+y^2} +}{x^2+2xc+c^2+y^2}$$

simplifying $-4a\sqrt{(x+c)^2+y^2} = 4a^2+4xc$ squaring again: $a^2(x^2+2xc+c^2+y^2) = a^4+2a^2xc+x^2c^2$ rearranging $a^2c^2-a^4 = x^2c^2-x^2a^2-y^2a^2$ $\Rightarrow a^2(c^2-a^2) = x^2(c^2-a^2)-y^2a^2$ so $1 = \frac{x^2}{a^2} - \frac{y^2}{c^2-a^2}$ define $b^2 \equiv c^2-a^2$ and the equation is in standard form: $\frac{x^2}{a^2} - \frac{y^2}{b^2} = 1$ Re-writing in terms of λ we have that $$1 = \frac{x^2}{\left(\frac{n\lambda}{2}\right)^2} - \frac{y^2}{c^2-\left(\frac{n\lambda}{2}\right)^2}$$

Hence sequential maxima are found on confocal hyperbolae, corresponding to increments of n.

If y is large with respect to c (typically the case for the embodiments of the present system), then the hyperbolae tend to their asymptotes:

$$\frac{x^2}{\left(\frac{n\lambda}{2}\right)^2} = \frac{y^2}{c^2-\left(\frac{n\lambda}{2}\right)^2} \Rightarrow \frac{x}{y}$$

$$= \sqrt{\frac{\left(\frac{n\lambda}{2}\right)^2}{c^2-\left(\frac{n\lambda}{2}\right)^2}}$$

$$= \sqrt{\frac{1}{\frac{c^2}{\left(\frac{n\lambda}{2}\right)^2}-1}}$$

$$= \sqrt{\frac{1}{\frac{(2c)^2}{(n\lambda)^2}-1}}$$

The conventional result for twin-slit interference is obtained by making the assumption that x<<y, so that:

$$\frac{x}{y} = \sqrt{\frac{1}{\frac{(2c)^2}{(n\lambda)^2}-1}} \approx \sqrt{\frac{1}{\frac{(2c)^2}{(n\lambda)^2}}} = \frac{n\lambda}{2c}$$

Figure 17:
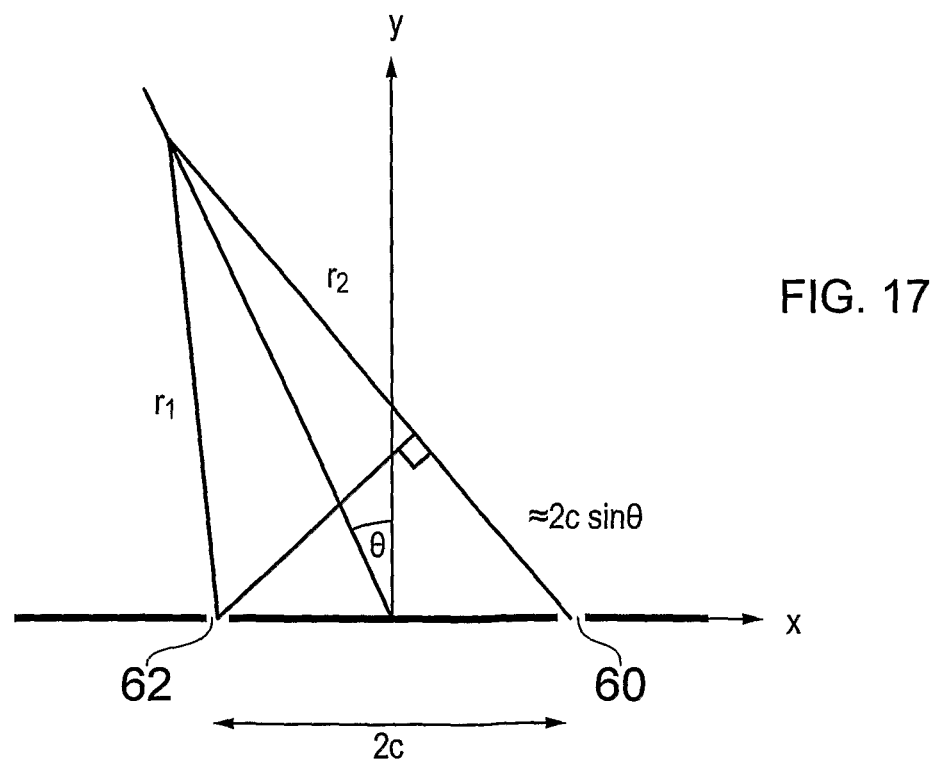

This is readily compared with the results conventionally obtained for the twin-slit system, as shown in FIG. 17. So for small λ and y>>x we have that the path difference is:

$$n\lambda \approx 2c\sin\theta \approx 2c\frac{x}{y}$$

And hence the spacing between fringes is given by:

$$\frac{x}{y} \approx \frac{n\lambda}{2c} \Rightarrow \frac{\delta x}{y} \approx \frac{(n+1)\lambda}{2c} - \frac{n\lambda}{2c} = \frac{\lambda}{2c}$$

Figure 18:
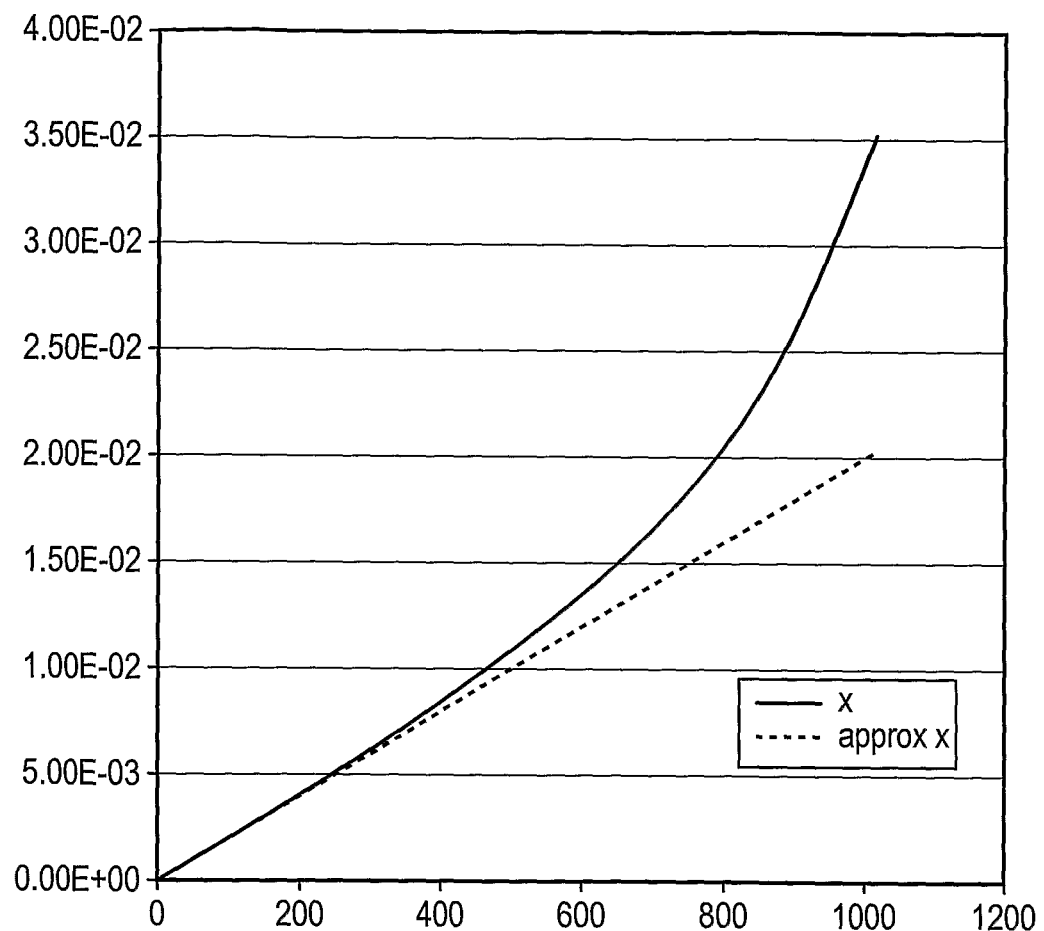
FIG. 18 shows a plot of x against n.
Figure 19:
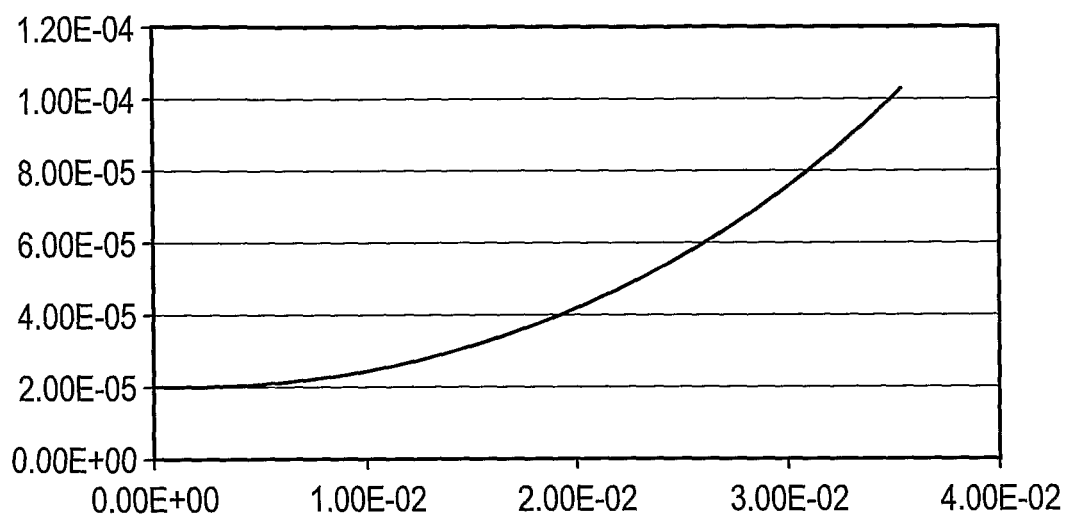
FIG. 19 shows a plot of δx against x for same conditions as in FIG. 18.

The exact and approximate expressions may be compared graphically, as shown in FIG. 18 which shows a plot of x (ordinate) against n (abscissa) for λ=532 nm, c=333 μm, y=25 mm n=0 to 1000 corresponding to on-axis spacing of 20 μm. In FIG. 18 it can be seen that the approximate expression for fringe spacing underestimates spacing at large angles. For example, when the angle is 45° (corresponding to x=y) the fringe spacing has increased from 20 μm on axis to 56.5 μm at 45°. The sampling theorem is therefore satisfied for all incident angles if the fringe spacing is calculated for imaging system pixel spacing on axis. It also suggests that the departure of fringe spacing from equal spacing may act as a measure of angle between detector and optical axis, as illustrated in FIG. 19, which shows a plot of δx (ordinate) against x (abscissa) for same conditions as in FIG. 18. The expression for δx against n is probably well represented by an even order polynomial.

One key uncertainty inherent in the use of a cheap laser for the system is the wavelength of light emitted by the laser. In the case of a simple diode laser, the wavelength may only be known to within about 1%. A Nd:YLF microlaser may perhaps provide performance about 10 times better than this. The use of a stable laser (gas laser, such as HeNe, nonplanar resonator YAG or DFB diode laser etc.) would be much more expensive, and, in some cases, would result in significantly larger physical size of the system, increased power consumption, etc. However, in the embodiment described below, the system does not necessarily need the laser used to be of high quality.

As discussed in detail above, the fringe spacing of the diffraction pattern is typically much larger than half a wavelength. Thus the coherence length requirement is considerably relaxed. The need for a single mode laser is also avoided for the same reason. However, the need for an accurate determination of the average wavelength remains.

Figure 20A:
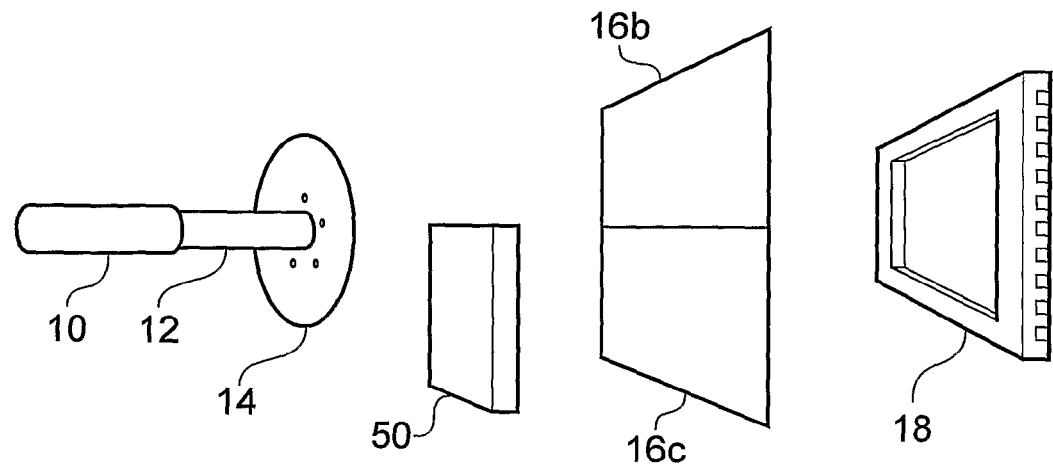
FIG. 20A shows a modified embodiment based on FIG. 3A.
Figure 20B:
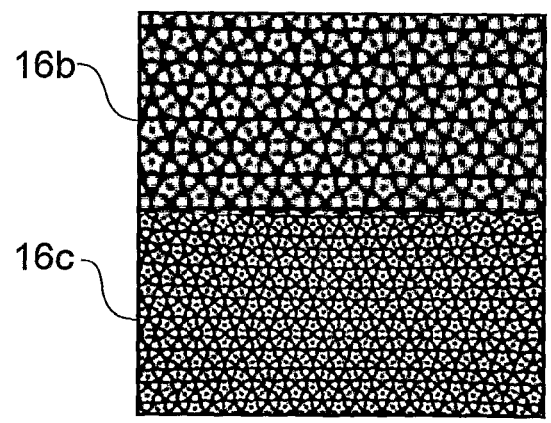
FIG. 20B shows a schematic view of the diffraction pattern captured at planer 16b,16c in FIG. 20A.

A possible solution is the use of a thick sheet of glass as an "etalon" in front of the detector, intercepting part of the light incident from the pinhole array. In effect, the detector is then two detectors—a first detector without etalon and a second detector with etalon, the detectors being coplanar and adjacent. The etalon has antireflective coatings to reduce multiple internal reflections (similar to a zero-Q etalon). This arrangement is illustrated in FIG. 20A, which shows similar features to those shown in FIG. 3 (identically numbered and not discussed further here) but additionally shows an etalon 50 intercepting the optical path between a second part of the detector 18 but not a first part of the detector 18. The consequential effect on the intensity pattern is shown as an unaffected part 16*b* and an affected part 16*c*. In effect, the affected part appears to be closer to the optic 14 than the unaffected part 16*b*.

The etalon 50 has the effect of reducing the effective distance from the optic 14 to the detector 18. Since the optical thickness of the etalon may be determined accurately and cheaply (there is typically a single calibration for a wafer of etalons which are then diced), the change in effective spacing measured at the top and bottom of the image is accurately known. The apparent change will depend on the wavelength of the laser. Thus the difference in apparent distances serves to calibrate the laser wavelength. The distance may then be determined with great accuracy using a cheap laser, since the wavelength is known. It is preferred in this case that the laser has a single transverse optical mode. This is an easy requirement to satisfy for a wide range of laser sources.

Using the conventional (approximate) dual-slit calculation, the fringe spacing is reduced by a "real-over-apparent-depth" argument. For an etalon having refractive index $n_e$ and thickness $t_e$ then the change in separation is only:

$$\frac{t_e(n_e - 1)}{n_e}$$

Off axis, more elaborate numerical calculations are required (Snell's law/ray tracing). Since the physical distance and orientation are known (to within the accuracy of the wavelength determination; iterative solution required), these calculations are readily performed.

In a preferred embodiment, the system is pumped using a YFL microlaser (DPY). In this case, the pump diode laser wavelength may be used to provide a second, coarse pattern for gross alignment. The collimating optic (if zone plates are used) can be used to selectively focus the different wavelengths (in this case green and red light) onto separate pinhole arrays in the same generator optic.

Figure 21A:
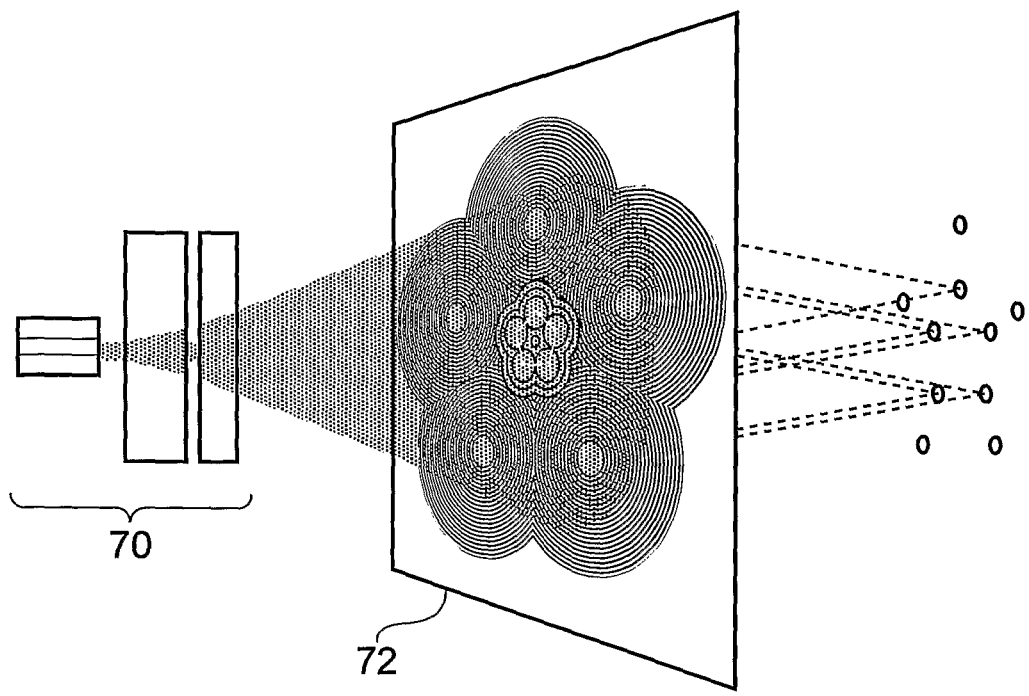
FIGS. 21A and 21B show a conventional frequency-doubled YLF microlaser used to illuminate a collimation optic for the generation of two intensity patterns (not shown) of differing wavelength.
Figure 21B:
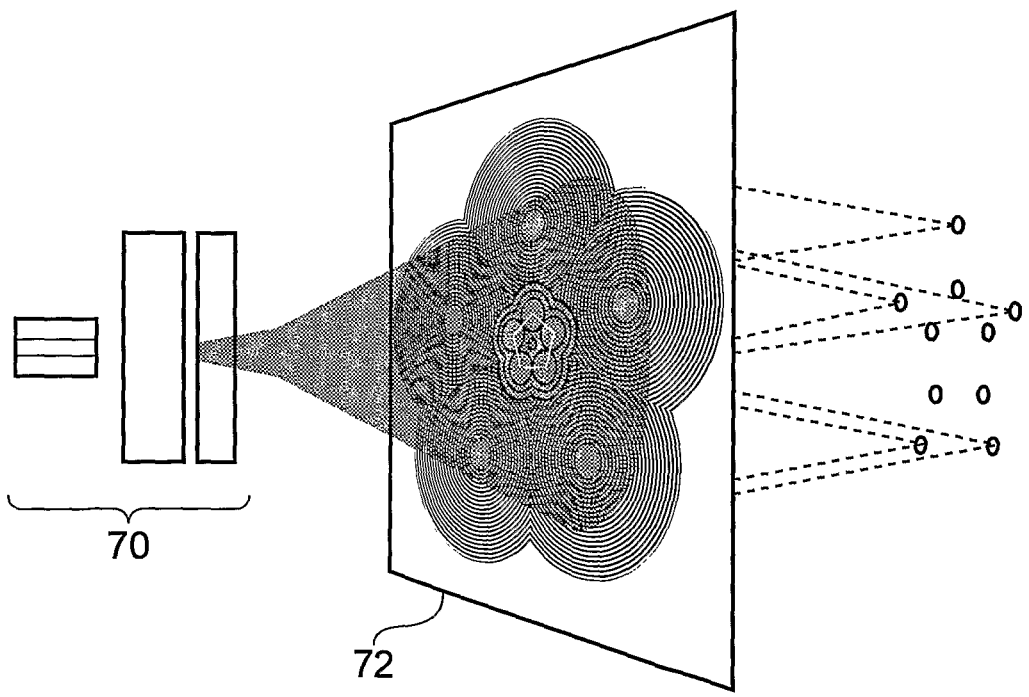

An example of this is shown in FIGS. 21A and 21B, in which a conventional frequency-doubled Nd:YLF microlaser 70 is used to illuminate a collimation optic 72. In the case depicted the coarse array (diode laser wavelength, intended for red light) is one 5-fold symmetric pattern and the fine array (laser wavelength, intended for green light) is another 5-fold symmetric pattern. However, as will be understood, different patterns (e.g. higher order patterns) might be used to eliminate or reduce rotational ambiguity about the optical axis. The coarser array collimates light towards a finer array of pinholes and the finer array collimates light towards a coarser array of pinholes.

In the case of the single wavelength system discussed above, the diffraction pattern is translationally aperiodic, but a certain minimum area of the field must be intercepted to give an unambiguous position. Also, some coarse indication of position aids in the rapid processing of the data. Since the diffraction pattern typically has rotational symmetry, there may be ambiguity in the positional information in terms of the angle around the optical axis.

When a second wavelength is used to generate a lower precision pattern, possibly having a different symmetry (e.g. 7-fold), the above problems may be eliminated. The second wavelength may be distinguished either by spatial filtering (numerical method) or by the use of a colour detector or filter (already present on commercial camera chips), or both.

In the case of a doubled YAG microlaser, a convenient extra source of the second wavelength is the pump diode laser (typically 860 nm). This is normally filtered out by a short-pass filter after the YLF crystal, although traces usually remain. Large amounts of red light are available simply by removing the filter, if the leakage power is found to be inadequate. The collimating optic can be diffractive, in which case the different wavelengths are brought to a focus on different pinholes, which act as the output "slits", monochromating the sources, and eliminating crosstalk. This is a highly convenient way of generating the additional pattern.

The present inventors further consider that suitable interference diffraction patterns for use with the invention may have some degree of translational periodicity, the period being relatively long in relation to the spacing of the maxima and minima of the pattern. As an example, a suitable diffraction pattern may be generated using a square of apertures of spacing two integers with one corner displaced from the geometric square by an integer fraction. It is intended here that the periodicity is determined in relation to the pattern produced by a single wavelength of light and not in relation to beat patterns that may be produced in the event that the pattern generator operates using more than one light wavelength. In another modification, in which the intensity pattern reaches the detector via a reflector, it is of interest to include at the reflector at least one area of modified refractive index. In a similar manner to the embodiments described above, this allows the detected pattern to include corresponding artefacts that can be used to assist in distinguishing between different parts of the intensity pattern.

Turning again to the issue of wavelength measurement, the inventors note that the measurement of wavelength is an important problem in optics. Coherent sources of electromagnetic radiation having very narrow linewidth are readily fabricated, but the absolute value of wavelength is not necessarily known with adequate accuracy. Examples of sources in the visible and near-infrared are Distributed Bragg Reflector (DBR) and Distributed Feedback (DFB) semiconductor laser diodes. For example, a suitable laser is available from Eagleyard Photonics GmbH (Rudower Chaussee 29, 12489 Berlin, Germany). Such lasers have many important uses. These include absorption spectroscopy for sensing applications (e.g. $O_2$ sensing), isotope separation by tuning to hyperfine levels in an atomic spectrum (AVLIS—see "Overview of Uranium Atomic Vapour Laser Isotope Separation" R. M. Feinberg and R. S. Hargrove, UCRL ID114-671 (1993)), Dense Wavelength Division Multiplexed (DWDM) fiber communications, spatial metrology etc. Unfortunately, although the linewidth of such a laser might be better than 1 MHz, the wavelength is strongly shifted by changes in drive current and temperature. Even if these are held constant, the wavelength of such a laser might be expected to drift by about 0.5% over the device lifetime. Measurement of the wavelength of such a laser requires the use of an expensive spectrometer, or else locking to a known spectral absorption line (see "Frequency stabilization of a 1.54 μm DFB-laser diode to Doppler-free lines of acetylene" Kurosu, T.; Sterr, U. Precision Electromagnetic Measurements Digest, 2000 Page(s):511-512). Both methods are complex and require bulky and complex external systems, effectively turning a cheap source of accurately tuned light into a very expensive one.

The resolution of a grating spectrometer, for example, is directly determined by the grating size. Thus a (relatively) conservative) 1 GHz resolution would require a grating of size corresponding to 0.5 ns time difference, or 15 cm. Optics to illuminate such a grating without significant aberrations are very expensive, and the system is likely to be physically large, making the attainment of adequate mechanical stability challenging. Spectrometers cost about £10 k or more even for this level of precision. One known method for achieving high precision without recourse to large systems is to use a Fabry Perot etalon. Such devices operate by allowing the light to perform multiple passes through a resonant cavity, so that the effective length of the cavity from the standpoint of resolution is increased by the number of round trips performed by the light (the "finesse" of the cavity). Thus if the wavelength incident divides the cavity length exactly a whole number of times, the Fabry Perot etalon will pass the light readily. If the light does not quite fit a whole number of wavelengths into the cavity, the light is reflected, not transmitted. A particular problem with this approach, however, is that the Fabry Perot etalon produces maximum transmission for many wavelengths. Thus a 1 cm long Fabry Perot used to investigate red light at an approximate wavelength of 632.82 nm (HeNe) will pass light at wavelengths of 632.831, 632.811 and 632.791 nm, corresponding to frequencies of $4.7373204213 \times 10^{14}$ Hz and adjacent frequencies spaced at 15 GHz intervals (the free spectral range). There is therefore a conflict between using a long etalon to achieve high accuracy in the measurement of wavelength and the use of a short etalon to increase the free spectral range and hence avoid accidentally locking the tunable laser to the wrong resonance.

Figure 22:
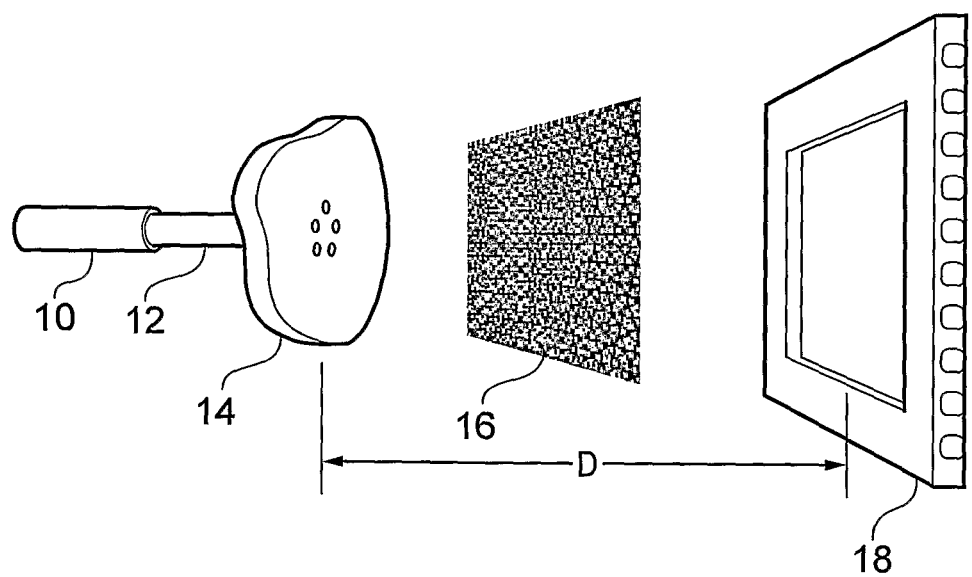
FIG. 22 shows a schematic view of an embodiment optically equivalent to FIG. 3 in which the separation of detector and optic are fixed, so that the spatial frequencies present in the aperiodic diffraction pattern impinging upon the detector can be used to measure of the wavelength of the input laser beam.

In one embodiment, a wavelength measurement system has many similar features to the embodiment described with reference to FIG. 3. However, this system is modified in order to perform an extremely precise and unambiguous measurement of laser wavelength. One embodiment of the wavelength measurement system is shown at FIG. 22. This differs from the system of FIG. 3 in that the diffractive optic is held at a fixed distance D from the detector.

In FIG. 22, when the distance from the diffractive optic to the detector is fixed, then the "magnification" of the diffracted pattern imaged at the detector will vary monotonically with wavelength. Referring again to the position determination systems discussed above, the measurement of distance between the generator and the detector is scaled to the laser wavelength used. Thus if the distance is physically held constant, then the measurement of "distance" becomes a measure of wavelength.

In order to hold fixed the distance between the generator and the detector, the generator (at least the optical element of the generator) and the detector are held in a thermally stable mechanical system, such as a frame or box made of quartz, zerodur, invar or other dimensionally stable material. Typically, before use, the separation between the optical element and the detector is calibrated (typically only one calibration required) using a single known wavelength (such as a stabilized helium-neon (HeNe) laser). Following this calibration, the system is able to measure wavelength with high accuracy at all wavelengths accessible to the optic and detector.

Figure 23:
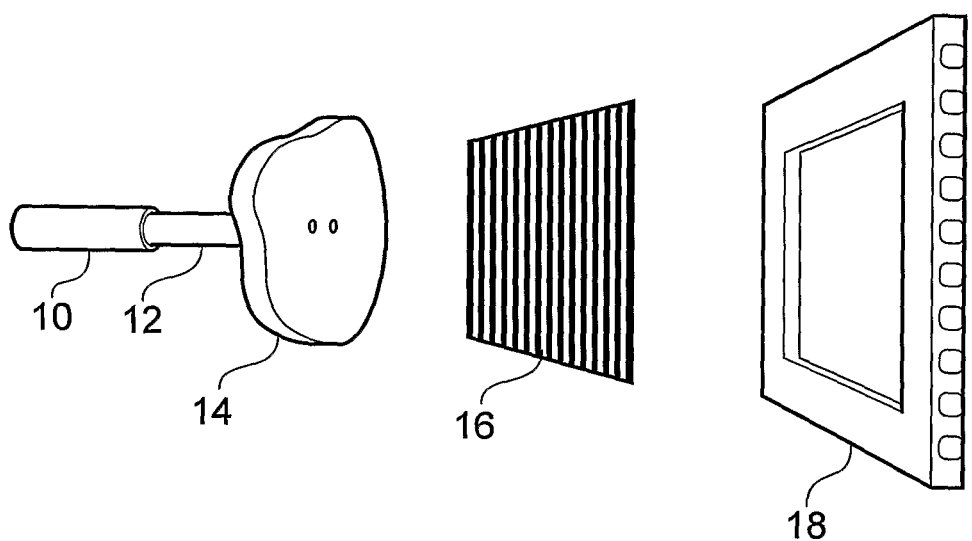
FIG. 23 shows a modification of the embodiment of FIG. 22 in that the fringes produced by the generator are approximately periodic in one dimension.

The embodiment described above can be simplified by using a less elaborate diffractive optical element. For example, if an element consisting of two pinholes is used, then the diffracted optical field is a sinusoidal ("Young's slits") pattern, as illustrated in FIG. 23. This is an example of a one dimensional diffraction pattern.

The interference pattern at the detector consists of sinusoidal fringes. The frequency of the sinusoid varies slowly across the detector, in the well-known fashion for two slit interference when not in the Fraunhoffer regime. Such a variation can be removed by a simple conformal mapping of the image such that the period of the fringes be rendered uniform. Once the fringe spacing had been rendered uniform, the frequency can be measured for example by use of a Discrete Fourier Transform (DFT), preferably using an efficient algorithm, such as the Fast Fourier Transform (FFT). The spatial frequency of the fringes may be estimated with very high accuracy by means of an interpolating algorithm, such as that defined in Xue and Yang 2003 ("Optimal interpolating windowed discrete Fourier transform algorithms for harmonic analysis in power systems" H. Xue and R. Yang IEE Proc. Gener. Transm. Distrib., 150, (5) p. 583-587 (2003)). In this way, the frequency of a waveform sampled in an FFT of only a thousand or so points may be determined to parts per billion accuracy.

In the case of a pair of apertures (2-pinhole case, e.g. FIG. 23), the pattern is essentially uniform in the direction perpendicular to the pinhole spacing, and hence the detector used may be a simple linear array (i.e. a one dimensional array of detection elements). This has the advantage that the numerical calculations can be performed using a 1-dimensional transform, not a 2-dimensional transform, resulting in a very significant saving in computational time. It should also be noted that the pixel readout rate of 1-dimensional detectors is approximately the same as that achieved in 2-dimensional detectors, so that the number of samples per second obtained can be much higher. This is a distinct advantage when the system were to be used to control the wavelength of the laser in real-time within a feedback loop. Alternatively, if the approximate wavelength is known to within one or a few integer spatial frequencies, then the processing required can require the calculation of only a very small number of spatial frequencies, also resulting in a very significant saving in time.

It is of interest to consider errors that may be associated with measurements carried out using the embodiments of FIGS. 22 and 23. When implemented as described above, there are a number of potential errors associated with the wavelength measurement system. For the purposes of illustration, calculations will be based on a hypothetical 2 cm spacing between the optical element (the "optic") and the detector.

Firstly, the differential expansion of the silicon detector and packaging (PCB) is typically of the order a few ppm/K for an expanding object of order 1 mm thick. The predicted temperature rise of the sensor is of the order of 10K, giving an expansion of 1 mm×2.6 ppm/K (silicon)×10K=26 nm in 2 cm, or about 1 part in $10^7$. Expansion of a spacer determining the distance between the optic and the detector may be made substantially zero by the use of low expansion materials and thermostatic control. Air pressure variations due to extreme weather variations typically result in index changes of 100 ppm, although the use of a simple pressure gauge or a sealed volume can readily eliminate any errors from this source. For a 2-dimensional detector having 1024 pixels square, 60 dB SNR (approximately saturated sensor) and twin slit fringes at the Nyquist limit the energy in the fringes is of the order of $10^{11}$ times larger than the random noise in a single frequency bin wide bandwidth. Interpolation can then give a random noise limited fringe frequency measurement of order $3\times10^{-6}$ minimum frequency bins, corresponding to $3\times10^{-9}$ fractional error (3 ppb) for short term measurements. Such an accuracy corresponds to a laser frequency jitter of just over 1 MHz. It is seen that the overall error is likely to be dominated by thermal expansion of the detector (0.1 ppm=50 MHz) where an optical sensor chip is used which suffers from significant thermal expansion as part of the distance reference.

Figure 24:
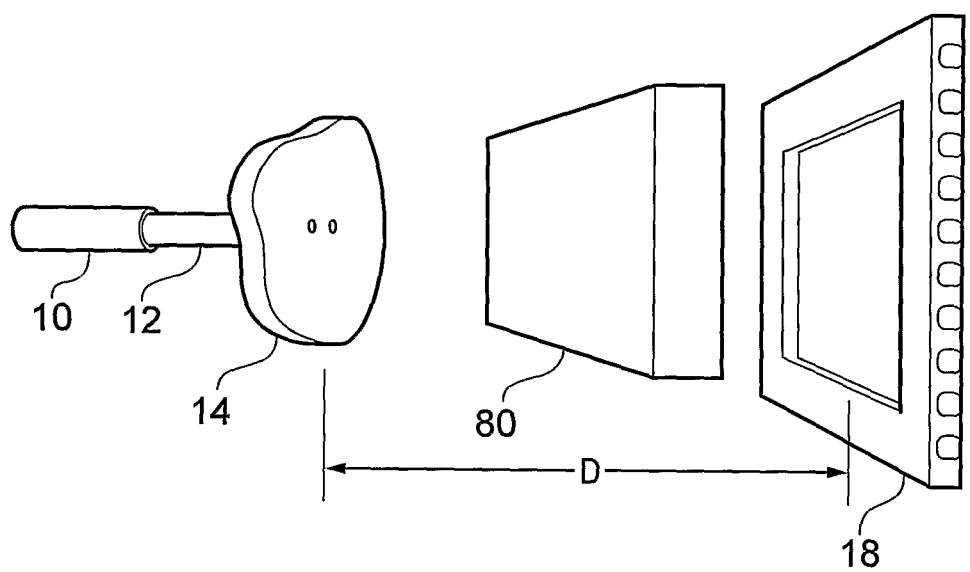
FIG. 24 shows a modification of the embodiment of FIG. 23 with an etalon 80 placed between the generator and the detector, so that successive passes of light through the etalon result in increasingly coarse fringes on the detector. Since the geometry of the etalon is known, the wavelength of the light forming the fringes may be inferred. The separation of optic and detector may therefore be measured using a laser having poorly defined wavelength.

One solution to the problem of thermal expansion of the detector is to use a passive optical element as a length standard. A good choice in this case is a low finesse solid etalon. Such an arrangement is shown in FIG. 24. In this case the separation between optic 14 and detector 18 is not critical, and indeed this distance may be varied in use. In operation of the system, use is made of the multiple round trip paths made within the etalon 80. After correction for geometric "chirp" of the fringe spacing each round trip will produce a fringe pattern at the detector which has a larger fringe spacing than the one before. The change in fringe spacing approximately corresponds to the double round trip distance in the etalon, scaled for refractive index.

Thus, since the etalon thickness is known and stable, the differences in apparent path length are an accurate measure of wavelength. Note that discrimination between subsequent round trip patterns is readily made in the Fourier domain, since they have different spatial frequencies. Also note that, unlike the case in a classical Fabry Perot interferometer, there is no ambiguity concerning the order of the fringes detected, since the system measures the path directly, rather than relying on resonance. The use of a low finesse cavity minimises reliance on patterns which have suffered many round trips, since these are likely to have inconveniently small spatial frequencies which will be uncomfortably close to those for subsequent round trips.

Thermal control is much simpler in this embodiment than in embodiments without the etalon, since the etalon does not necessarily dissipate any power (for example a quartz etalon with dielectric coatings) and hence may, if desired, be subjected to thermostatic control with negligible power load.

As mentioned above, the detector may be a linear array of detection elements (pixels). In this case the number of pixels associated with a single measurement is reduced compared with a two dimensional array of detection elements, but for equal data rate the total noise signal per second is the same (linear and area CODs are both clocked at similar numbers of pixels per second). This provides a means for the incorporation of the wavelength measurement system within a fast feedback loop for control of a tunable electromagnetic radiation source.

Figure 25:
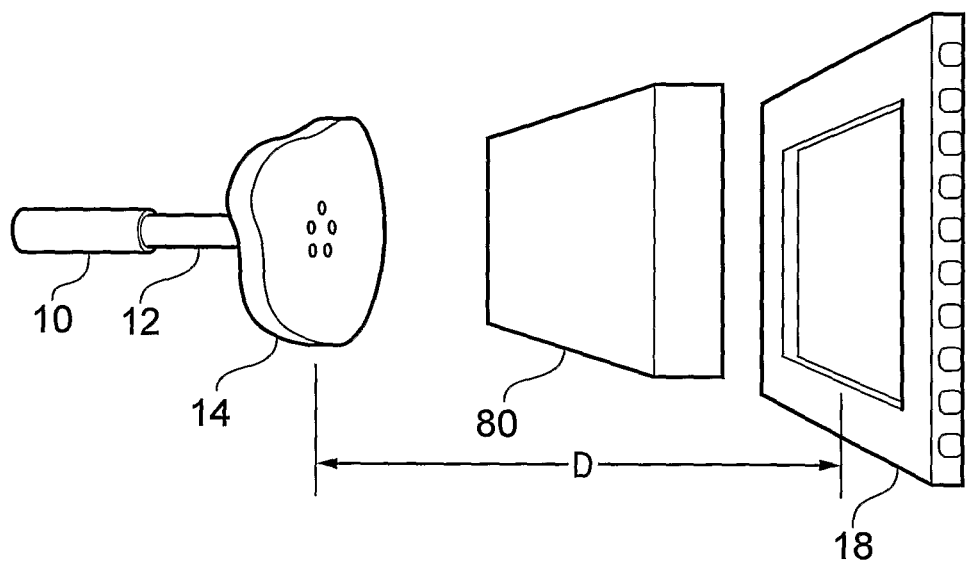
FIG. 25 shows a modification of the embodiment of FIG. 24 in which the detected fringe pattern is aperiodic.

The use of an etalon to accurately measure the wavelength of the laser also allows the measurement of the laser wavelength in a position determination system as described above. Thus, modifying the embodiment of FIG. 3 as shown in FIG. 25, to insert an etalon 80 into the optical path between the generator and the detector, then the diffracted field will consist of a set of interference patterns (e.g. translationally aperiodic interference patterns in this embodiment) corresponding to the measured field as in the embodiment of FIG. 3, but further including replicas of that field corresponding to increasing distance from the sensor due to a number of "double round trip" passes through the etalon. The distance between successive replicas is defined by the physical dimensions and refractive index of the etalon. The apparent distance, however, is also scaled by variations in the average wavelength of the laser used. Thus, since the separation between subsequent round trips is accurately known, then the wavelength is readily calculated and hence the physical distance to the first instance of the optic is also calculable.

Figure 26:
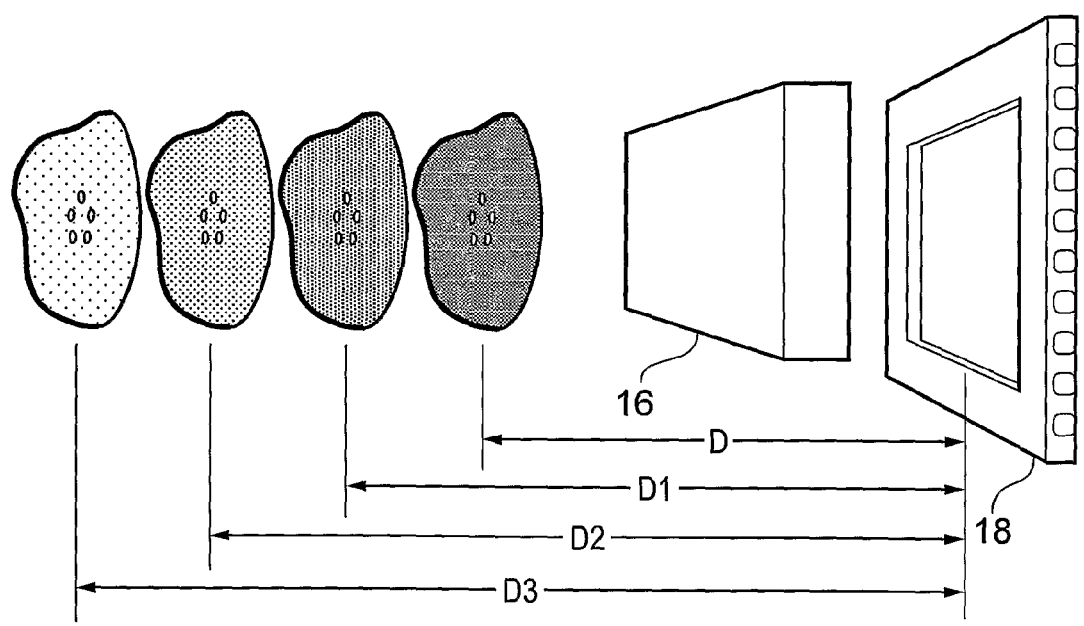
FIG. 26 illustrates the mode of operation of the embodiment of FIG. 25. A series of interference patterns are measured, of decreasing intensity and spatial frequency, corresponding to the formation of "images" of the pinholes at increasing distances from the detector. Subsequent images are spaced by approximately twice the etalon optical thickness.

FIG. 26 illustrates schematically the operation of the embodiment of FIG. 25. The apparent position of the optic (as "seen" from the detector) after one round trip is spaced by twice the etalon thickness from the physical optic position, total distance D1. Subsequent (weaker) positions are additionally spaced by the same amount, total distances D2, D3, etc. Determination of the spacing gives a measure of wavelength λ.

The use of an etalon to dynamically measure the laser wavelength is important since it allow the use of many different types of lasers in a position determination system or other system according to an embodiment of the present invention. For example, low cost lasers may be used (such as Fabry Perot cavity diode lasers), or narrow linewidth lasers of poorly determined wavelength (such as DFB/DBR diode lasers), or short pulse lasers (with wide bandwidth and poorly defined centre wavelength) may be used. Thus, following on from the calculations above, a position determination system, used to measure position in up to 6 axes, can have a wavelength-defined accuracy equal to that of the wavelength measurement (parts per million), even if the laser used has a variable wavelength. Note also that the previously defined calculations concerning random errors in wavelength (due to shot noise in the detector) referred to a single measurement. In the case of position measurement, changes in wavelength of the laser are expected to be slow. Random errors may therefore be reduced significantly by averaging, interpolating and/or predicting the measured value for wavelength over more than one cycle of positional measurement. Thus extreme accuracy in wavelength measurement may be made even with a relatively thin etalon. Note also that the use of an etalon in a single frame measurement allows the use of a laser which changes wavelength rapidly in time, for example if a measurement is made immediately after turning on the laser. This fits well with a notable characteristic of the embodiments of the present invention, which is that there is no need to count fringes in moving away from zero position. A single pulse of laser light is sufficient to fix absolute position in space. Thus the use of in situ wavelength measurement enables accurate measurement of position or refractive index when these properties are varying rapidly (for example in ballistics studies).

Figure 27:
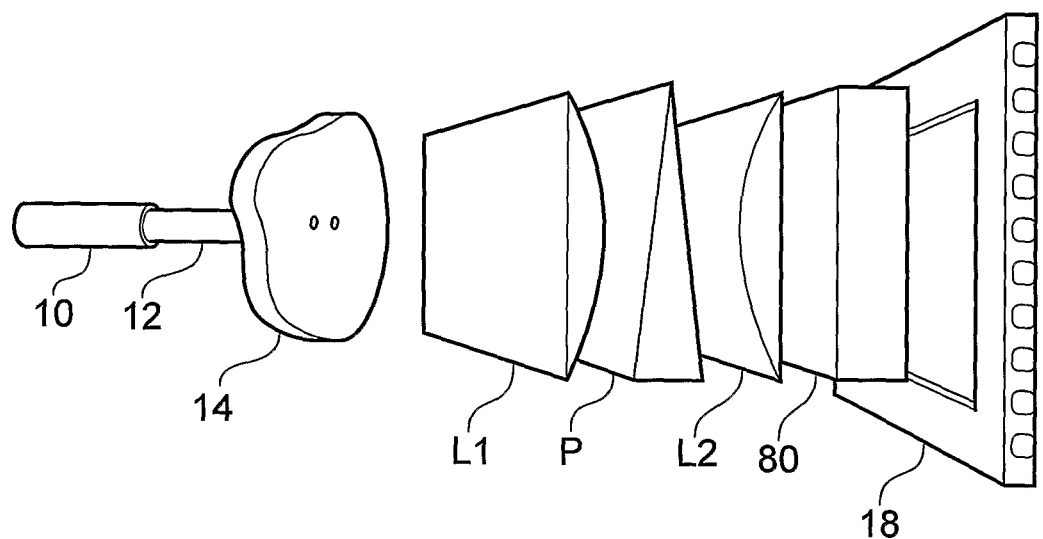
FIG. 27 shows a modification of the embodiment of FIG. 23 in which a system of cylindrical lenses (L1,L2) is interposed between the generator and the detector.

In another embodiment, there is provided another application of a similar principle to the measurement of wavelength with high accuracy for more than one wavelength, typically for a number of relatively widely spaced wavelengths. In this case wavelengths may be measured accurately by use of a 1-dimensional diffraction pattern. The use of a low resolution dispersive element (such as a grating, prism, etc.) allows the separation of the widely spaced frequencies on the detector in a direction perpendicular to that of the diffraction pattern. This is illustrated in FIG. 27 in which a twin slit diffractive element is used to generate the diffraction pattern used for precision wavelength measurement. Different colours of light (e.g. red and green) are dispersed in this case using a 1-dimensional "spectrometer" (actually a prism spectrograph), consisting of two cylindrical lenses, L1 and L2, and a prism, P. These elements can be replaced by corresponding arrangements of mirrors or gratings etc. Alternatively, interference or other filters may be placed at different positions on the detector, to discriminate between colours.

In FIG. 27, which is a modification of the embodiment of FIG. 23, a system of cylindrical lenses (L1,L2) is used to form a real-space image of the pinholes in one dimension (i.e. a stripe across the detector). The stripe is dispersed by a prism (or grating) (P) such that widely separated wavelengths are spatially separated on the detector, in a manner similar to a conventional spectrograph. For each wavelength thus dispersed, the fringe spacing (perpendicular to the direction in which wavelengths are separated by means of the prism) is used to measure the wavelength with very high accuracy and precision. The use of an etalon (80) may provide additional accuracy, since the optical thickness of L1, L2 and P is poorly defined.

Applications of this technique include the measurement and control of all the wavelengths in a wavelength division multiplexed (WDM) communications channel. The "spectrometer" splits the channels up and the etalon (if present) and diffraction pattern would be used to perform the precision measurement of centre wavelength.

In the embodiments described above, the etalon has a fixed and known thickness and refractive index, so that the optical thickness of the etalon is known, the etalon in effect providing means for calibrating the system. In an alternative embodiment, the "etalon" may be replaced by a cell filled with a substance of unknown index, or a slab of unknown material, then the optical thickness of the "etalon" would be the measurand. If the physical dimension of the etalon were fixed (e.g. as a cuvette) then the system can be used to determine refractive index. Alternatively, when the whole volume between the optic and the detector is filled with the material, and if the spacing between the optic and the detector is fixed, then the apparent distance between the optic and the detector would be a measure of index, provided that the wavelength is fixed.

In a further modification, it is possible to provide in the system an etalon of known thickness and refractive index to measure the wavelength and a block/cuvette of unknown material of known dimensions to measure the refractive index of the unknown material. Typically, the block/cuvette is located in the volume between the etalon and the detector. A calibration measurement may be taken with the block/cuvette absent or empty. A subsequent measurement taken with the block/cuvette present or filled would give an apparent distance change, which in turn provides a measure of refractive index. For example, this technique may be applied to measure the pressure in a gas, for example.

In a still further embodiment, there is provided a position measurement system adapted to measure rotation around a principal axis.

The measurement of rotation angle is fundamental to many areas of technology. Whilst there are several known convenient methods for the measurement of linear displacement, the precise measurement of arbitrary angles is generally less well served. Low precision measurements are readily made using simple sensors such as rotary potentiometers, variable capacitors or Rotational Variable Differential Transformers (RVDTs). More accurate measurements are generally made using rotary encoders, which can be accurate, but often have rather limited precision. For example, the most precise rotary encoders feature accuracy of approximately ±5 μrad. These are expensive and large systems (for example the Renishaw REXM encoder (available from Renishaw plc, New Mills, Wotton-under-Edge, Gloucestershire, GL12 8JR, United Kingdom) achieves this accuracy only for encoder sizes over 100 mm).

In the rotational measurement embodiment, it is preferred that the interference pattern simply has one or more periodic patterns of stripes or fringes, having a strong spatial frequency component in one or more directions. For example, a one dimensional interference pattern such as from two apertures can be used. Such a pattern at a planar detector, suffers a well-defined geometric distortion which is a simple function of the distance of the detector from the apertures. The detected pattern may be distorted during processing of the data from the detector in the opposite direction to that imposed by the geometry to make the fringes straight and parallel across the field. The rotation angle may then be measured by performing a discrete Fourier transform or related transform on the image. By use of a suitable interpolating algorithm the peaks of the transformed pattern may be determined to an accuracy which is much less than the interval between discrete frequencies, using the analysis provided by Xue and Yang 2003 (see reference above).

The accuracy to which the angular position of the sensor relative to the aperture axis may be determined is then limited by noise in the photodetector. See the analysis set out above with respect to the accuracy during position measurement/wavelength measurement.

It is now useful to consider in more detail the interpolation in order to locate very precisely the maxima (or minima) of the interference pattern. This interpolation is based on the window functions provided by Xue and Yang 2003.

Xue and Yang 2003 derive forms for the window functions giving the maximum rate roll off in intensity for single frequency spots in a Fourier transform where the frequency of the sampled waveform has a non-integer number of cycles over the length of the transform. Thus, if there are a number of frequencies present, the spot in the Fourier domain from one frequency will not bleed over into the others. It follows that different frequencies are well resolved. This is very useful in positional determination (and in measurements of other physical parameters) because it means that a complex optical interference field can be analysed relatively simply and considered as a set of independent non-interacting two-pinhole diffraction patterns. Note that this is of particular utility for relatively complex interference patterns—when the interference pattern is formed from only two pinholes, then the present analysis provides a lesser advantage.

Xue and Yang 2003 also give expressions for interpolation of the centre frequency from the values near the peak in the FFT. Thus if the frequency of a sampled waveform would be 78.6 cycles per record length (i.e. a whole number of cycles would not fit in to a sequence that will be transformed), Xue and Yang 2003 give a simple expression to get the value 78.6, even though the FFT decomposes the waveform into integer frequencies only (77, 78, 79 etc.). In practice this is exceptionally accurate, so that whereas the resolution of a simple 256-long FFT is only to the nearest 256th of the maximum frequency input, a simple test in Microsoft Excel for pure sinewaves gives an accuracy in the parts per billion range. Thus, a real frequency of 50.15 gave an interpolated value of 50.150000000192, limited by the accuracy of floating point numbers in Microsoft Excel.

In use of the system, it is possible to detect several few cycles of the interference pattern and use interpolation to measure the centre frequency with exceptional precision. A typical conventional view is that it is possible to count a number of fringes to about 1/10th of a fringe. Using the approach outlined above, it is possible to count to a very small fraction of a fringe, assuming that the signal to noise ratio is acceptable (see below). Note that in the case that the fringes are subject to a variation in frequency over the transform length the simple interpolation function provided by Xue et. al. is inadequate. In this case it is possible to derive a more complex interpolation function based on numerical modelling of the lineshape as a function of centre frequency and change in instantaneous frequency over a transform. The use of other interpolating functions in no way affects the fundamental conclusion that the extraction of the characteristics of a wave from its transform may be performed with an accuracy limited only by noise in the detector and any numerical approximations made.

In the case of where the interference pattern is produced using only one pair of pinholes, the signal to noise ratio is increased by a factor of 10 (since fewer sine waves provides better dynamic range). Thus it is possible to measure fringe spacing to about 1/5000 of a minimum frequency. At the Nyquist limit (800 fringes across a 1600 pixel sensor along a line) this is 1 part in 800*5000, i.e. 0.25 ppm. In rotation terms this is an angle of 1/(2*pi*800*5000)=40 nradians. This is 10 marcsec precision, or 100× better than the quoted accuracy of the best known rotary encoders, such as the Heidenhain RPN 886 (available from Heidenhain Inc., of 333 East State Parkway Schaumburg, Ill. 60173-5337, USA) and even better than that quoted for rotary calibration systems such as the Renishaw RX10 (available from Renishaw plc, New Mills, Wotton-under-Edge, Gloucestershire, GL12 8JR, United Kingdom).

Note that accuracy (as opposed to precision) can be compromised by the orthogonality of the axes of the pixels in the camera sensor, defined by the lithography system used to make it. For a known stepper such as the Nikon NSR2205i11D, a 0.35 μm machine, this is 0.1 arcsec on stage motion, and the distortion over a field is 45 nm (15 nm after calibration). In the worst case scenario where this distortion is all orthogonality error, the accuracy would be 15 nm in 25 mm angle, or 0.124 arcsec. The present inventors consider that this is still better than the base accuracy of a machine tool "calibration" system.

Consideration of Random Errors

It is of interest to consider the random errors provided by systems according to the preferred embodiments.

The different motions detectable by the system are differently sensitive to random errors and the characteristics of the detector. The present analysis is concerned with the influence of random errors due to detector noise on the results obtained.

CCD and CMOS detectors with arrays of pixels are susceptible to pattern specific noise (i.e. the sensitivity of individual pixels may differ from each other) and to random noise arising from readout electronics and the quantized nature of light (shot noise). The analysis of data from the patterns detected at the detector is based on the use of 2-dimensional discrete Fourier transforms and window functions having optimised roll-off in the frequency domain. As a result, defects in the detector may be expected to be averaged away in the process of transformation. For example a single dead pixel transforms to a uniform (white) signal which has the least possible influence on the (large) signal produced by coherent signals which transform to an approximate delta function in the spatial frequency domain.

The key theorem to be used in this analysis is the known Wiener-Khinchine Theorem, which broadly relates the energy present in the transform to that in the spatial domain. Thus if the total energy in the signal is $E_{sig}$ and the total noise energy is $E_{noise}$ then the ratio $$\frac{E_{signal}}{E_{noise}}$$

is the same in both spatial frequency and real-space domains.

It is now necessary to define the sensor parameters. The characteristics of the sensor are as follows:

Single pixel signal-to noise ratio is $SNR_{SP}$. A typical value is $10^3$ (i.e. 60 dB) for a good sensor.

Number of x-pixels $N_x$. A typical value is 1600.

Number of y-pixels $N_y$. A typical value is 1200.

Pixel spacing L. A typical value is 6 μm.

Now turning to the key properties of signal detected at the detector, the noise component is assumed to transform to a uniform amplitude random phase signal. The signal component consists of the interference pattern caused by ten cosinusoidal waves at distinct angles. For the purpose of this analysis the ten cosinusoids are assumed to have uniform spatial frequency. The cosinusoids are assumed to have equal amplitude and the sensor is assumed to be just saturated for maximum input amplitude (at position in the sensor corresponding to the centre of the pattern). Thus if a position on the sensor is expressed as $\underline{r}=(x,y)$ where x and y are positions in meters the signal (amplitude) is given by:

$$a(\underline{r}) = \sum_{i=0}^{9} 1 + \cos(\underline{r} \cdot \underline{k_i})$$

where $\{\underline{k_i}\}$ is the set of wave vectors representing the five cosinusoids. Thus the maximum amplitude is 20 and the average amplitude (i.e. the DC value) is 10. The DC offset is present because the electrical signal generated at the sensor is proportional to the intensity of an optical signal, which is always positive.

The DC component of the sum of the cosinusoids transforms as $10 \leftrightarrow 10\delta(k)$ The oscillatory component of the individual cosinusoids transforms to a pair of spatial frequencies:

$$\cos(\underline{r} \cdot \underline{k_i}) \leftrightarrow \frac{\delta(\underline{k} \pm \underline{k_i})}{2}$$

so that the spectrum will be of the form $$A(\underline{k}) = 10\delta(\underline{k}) + \frac{1}{2}\sum_{i=0}^{9} \delta(\underline{k} - \underline{k_i}) \quad [11]$$

In practice the transforms are calculated using optimal window functions so that the delta functions are spread over a compact range of spatial frequencies. Since both the random noise and signal are uniformly distributed in space both are attenuated equally by application of the window function, so that the ratio of total signal energy to noise energy is conserved. Spatially localised "noise" sources such as dust particles will be subject to a range of attenuations (for example the influence of a speck of dust at the corner of the sensor will be attenuated to zero by the window function), but assuming there are a number of defects uniformly distributed over the sensor we may regard them as being equivalent to a spatially uniform error signal.

Turning now to the window function, since the Fourier analysis is accomplished on discrete data there is a question as to the nature of the "delta functions" described above. After application of the window function the "delta function" will be smeared out to cover a number of points in the transform. Looking at the window functions described by Xue and Yang 2003, we have that the distribution of amplitudes close to the maximum are given by the following expression:

$$X_K(n) = \sum_{i=0}^{K} (-1)^i \frac{a_i}{2}[X(n-i) + X(n+i)]$$

where
X is the amplitude of the spectral component before windowing
$X_K$ is the amplitude of the spectral component after windowing
K is the order of the window
$a_i$ is weight function of the window function
n is the discrete spatial frequency
The values of $a_i$ are given by

| K | $a_0$ | $a_1$ | $a_2$ | $a_3$ |
|---|---|---|---|---|
| 1 | 1/2 | 1/2 | | |
| 2 | 1/4 | -1/3 | 1/12 | |
| 3 | 1 | -3/2 | 3/5 | -1/10 |

We may scale the values of $a_i$ such that the total sum of squares is 1 (i.e. equal total energy in the spectral line):

| K | $a_0$ | $a_1$ | $a_2$ | $a_3$ |
|---|---|---|---|---|
| 1 | 0.707106781 | 0.707106781 | 0 | 0 |
| 2 | 0.588348405 | -0.784464541 | 0.196116135 | 0 |
| 3 | 0.525588331 | -0.788382497 | 0.315352999 | -0.052558833 |

The frequency is obtained by analysis of amplitude of the maximum amplitude component and the next highest one. Random noise will degrade the measurement of the amplitude of the spectral components, causing an error in the apparent centre of the peak. If the spatial frequency is given by $m=m_1+r$, where $m_1$ is the integer spatial frequency corresponding to maximum amplitude and m is the (non-integer) spatial frequency of the signal sampled by the pixel array then it is shown by Xue and Yang 2003 that the value of the fractional component of spatial frequency is given by $$K = 1: r = \frac{2-a}{1+a} \text{ where } a = \frac{|X_1(m1)|}{|X_1(m1+1)|}$$

$$K = 2: r = \frac{3-2a}{1+a} \text{ where } a = \frac{|X_2(m1)|}{|X_2(m1+1)|}$$

And hence, for a small error in a:

$$K = 1: \frac{dr}{da} = \frac{2-a}{(1+a)^2} - \frac{1}{1+a}$$

$$K = 2: \frac{dr}{da} = \frac{3-2a}{(1+a)^2} - \frac{2}{1+a}$$

The two limiting cases are for r=0.5 and r=0.
The numerical amplitudes for the two cases (1-D) are as follows:

| K | r | X1(m1-2) | X1(m1-1) | X1(m1) | X1(m1+1) | X1(m1+2) |
|---|---|---|---|---|---|---|
| 1 | 0 | 0.000 | 0.408 | 0.816 | 0.408 | 0.000 |
| 1 | 0.5 | 0.020 | 0.139 | 0.693 | 0.693 | 0.139 |
| 2 | 0 | 0.120 | 0.478 | 0.717 | 0.478 | 0.120 |
| 2 | 0.5 | 0.031 | 0.278 | 0.649 | 0.649 | 0.278 |

In the case of r=0 K=1 the energy of the m1+1 component is minimum, being $0.408^2$ of the total, or 16.7% of the total energy in the peak. The energy of the m1 component is 0.816²=66.7% of the total and the value of the ratio of the peaks is a=2, so $$\frac{dr}{da} = -\frac{1}{3}.$$

In the second case (r=0.5 K=1), where the spatial frequency lies exactly mid-way between two integer frequencies, both amplitudes are equal and they each contain 48% of the total energy and $$a = 1 \text{ and } \frac{dr}{da} = -\frac{1}{4}.$$

In the third case (r=0 K=2), the energy of the m1+1 component is minimum, being 0.478² of the total, or 22.9% of the total energy in the peak. The energy of the m1 component is 0.717²=51.4% of the total and the value of the ratio of the peaks is a=1.5, so that $$\frac{dr}{da} = -\frac{4}{5}.$$

In the last case (r=0.5 K=2), where the spatial frequency again lies exactly mid-way between two integer frequencies so that once more both amplitudes are equal, each contains 42.2% of the total energy and a=1, so that $$\frac{dr}{da} = -\frac{3}{4}.$$

In two dimensions, the energy within the peaks is spread out in the same way as explained above with respect to the one dimensional analysis above, but in two dimensions. Thus the total energy measured in the peaks is reduced by a similar amount, so that we expect about half of the total energy in the two dimensional peak to be useful in measuring the peak position in each dimension.

Bringing this analysis together to consider the signal to noise in the transform domain, the amplitude of each peak in the Fourier domain is 0.5 (from [11]), where the maximum signal in any pixel (where they all line up) is 20. The average signal level for a particular Fourier component in each pixel is therefore given by $$A_i = 0.5 \cdot \frac{SNR_{SP}}{20}$$

with respect to the noise level in each pixel. The noise level in each pixel in the transform domain is the same as in the time domain (white noise), but the signal in the Fourier peak is increased by the total number of pixels (since it is coherent), i.e.

$$\frac{\text{Total signal energy in Fourier peak}}{\text{Noise energy in an individual spatial frequency bin}} = \left(0.5 \cdot \frac{SNR_{SP}}{20}\right)^2 \cdot N_x N_y$$

This gives us an estimate of the error expected in determining the value of a, and hence of r, which is what is wanted here.

It is apparent that the worst case value for the determination of a is when the amplitude of the m1+1 value is minimum. In this case the 1-dimensional proportion of the total signal power present in the measured frequency bin is:
K=1 16%
K=2 22.9%
so that in a 2-d transform the proportion of the total energy in the peak will be reduced to, respectively:
$P_{bin}$=K=1 8%
K2 11.5%

The signal to noise ratio of the measurements of amplitude will then be given by the proportion of the total signal power in the bin divided by the noise power in the bin. This is given by:

$$SNR_{bin} = \sqrt{\left(0.5 \cdot \frac{SNR_{SP}}{20}\right)^2 \cdot N_x N_y \cdot P_{bin}} = 0.5 \cdot \frac{SNR_{SP}}{20} \sqrt{N_x N_y \cdot P_{bin}}$$

and the error in the determination of the value of r will be $$\varepsilon(r) = \left|\frac{dr}{da}\right| / SNR_{bin} = \begin{array}{l} K = 1: \frac{1}{3} / 0.5 \cdot \frac{SNR_{SP}}{20} \sqrt{N_x N_y \cdot 0.16} \\ K = 2: \frac{4}{5} / 0.5 \cdot \frac{SNR_{SP}}{20} \sqrt{N_x N_y \cdot 0.229} \end{array}$$

Thus, if:

$$K = 1 \ SNR_{bin} = 0.5 \cdot \frac{10^3}{20} \sqrt{1600 \cdot 1200 \cdot 0.08} = 490$$

$$K = 2 \ SNR_{bin} = 0.5 \cdot \frac{10^3}{20} \sqrt{1600 \cdot 1200 \cdot 0.115} = 587$$

and $$\varepsilon(r) = \begin{array}{l} K = 1 \ 6.8 \cdot 10^{-4} \\ K = 2 \ 1.36 \cdot 10^{-3} \end{array}$$

Note that the error in measuring r is worse with K=2; this is because the spectral line is slightly fatter, so that variation in the value of a (due to noise) gives a larger change in r. The tradeoff is simply that for K=1, we have sharper lines, with worse crosstalk but better precision in the presence of random noise, and for K=2 we have fatter lines, with less precision in measuring the centre frequency, but greatly improved immunity to adjacent spectral features.

Turning now to the effect of noise on individual axes of measurement, noise in the FFT will lead to noise in the inferred values of the different coordinates measured by the system.

z measurement: This is limited by the accuracy with which the period of the different waves can be measured over the whole sensor after appropriate conformal (or other) mappings have been done. For each pair of pinholes we get two frequencies (positive and negative frequency) with uncorrelated noise. This reduces the error in the average frequency measurement by a factor of $\sqrt{2}$. Alternatively, if we look at all 20 frequencies, the noise in frequency measurement is improved by averaging by a factor of $\sqrt{20}$.

At a given distance, the approximate period of the diffraction pattern for a pair of pinholes is given by the textbook twin slit interference calculation, illustrated in FIG. 17.

[We note here that θ is used elsewhere in this document to denote rotation about the z-axis. The use of this symbol is local to the discussion here and to FIG. 17.]

So, for small θ and y>>x we have that the path difference is $$n\lambda \approx 2c\sin\theta \approx 2c\frac{x}{z}$$

And hence the spacing between fringes is given by $$\frac{x}{z} \approx \frac{n\lambda}{2c} \Rightarrow \frac{\delta x}{z} \approx \frac{(n+1)\lambda}{2c} - \frac{n\lambda}{2c} = \frac{\lambda}{2c} \therefore \delta x \approx \frac{\lambda z}{2c}$$

The closest useable separation between pinholes and sensor is when the fringes are at the Nyquist limit. In this case $\delta x = 2L$. In this case the maximum spatial frequency of the fringes in the FFT is approximately:

$N_x/2$ in the x direction $N_y/2$ in the y direction.

The error in the value of r for a single pair of pinholes is given by $$\varepsilon(r) = \left|\frac{dr}{da}\right| / SNR_{bin} = \begin{matrix} K=1: \frac{1}{3} / 0.5 \cdot \frac{SNR_{SP}}{20}\sqrt{N_x N_y \cdot 0.16} \\ K=2: \frac{4}{5} / 0.5 \cdot \frac{SNR_{SP}}{20}\sqrt{N_x N_y \cdot 0.229} \end{matrix}$$

and this corresponds directly to the error in the frequency in the Fourier domain.

So we have that the measured frequency will be:

$$\frac{N_x}{2} \pm \varepsilon(r) \text{ or } \frac{N_y}{2} \pm \varepsilon(r)$$

The fractional error in z is equal to the fractional error in frequency, so $$\frac{\varepsilon(z)}{z} = \begin{matrix} K=1: \frac{1}{3} / 0.5 \cdot \frac{SNR_{SP}}{20}\sqrt{N_x N_y \cdot 0.16} \cdot N_{(x \text{ or } y)}/2 \\ K=2: \frac{4}{5} / 0.5 \cdot \frac{SNR_{SP}}{20}\sqrt{N_x N_y \cdot 0.229} \cdot N_{(x \text{ or } y)}/2 \end{matrix}$$

Thus:

$$\frac{\varepsilon(z)}{z} = \begin{matrix} K=1: \frac{80}{3 SNR_{SP}\sqrt{N_x N_y \cdot 0.16} \cdot N_{(x \text{ or } y)}} \\ K=2: \frac{64}{SNR_{SP}\sqrt{N_x N_y \cdot 0.229} \cdot N_{(x \text{ or } y)}} \end{matrix}$$

Typical numbers are (use $N_y$ as this is the worst case)

$$\frac{\varepsilon(z)}{z} = \begin{matrix} K=1: \frac{80}{3000\sqrt{1600 \cdot 1200 \cdot 0.16} \cdot 1200} = 40 \cdot 10^{-9} \\ K=2: \frac{64}{1000\sqrt{1600 \cdot 1200 \cdot 0.229} \cdot 1200} = 80 \cdot 10^{-9} \end{matrix}$$

For a typical distance of 1 inch this corresponds to 1 or 2 nm.

If we use all 20 spectral lines this improves by a factor of $\sqrt{20}$, giving 0.23 or 0.46 nm.

x and y measurement: For x and y we have an accuracy defined by the phase error in our measurement of the spectral lines. This is given by $\pi \cdot \in(r)$. Since the period of the fringes at the Nyquist limit is 2L this phase error corresponds to a positional error of $$\frac{2L}{2\pi} \cdot \pi\varepsilon(r) = L\varepsilon(r).$$

Substituting in our expression for $\in(r)$ $$\varepsilon(\langle x \text{ or } y\rangle) = \begin{matrix} K=1: L\cdot\frac{1}{3} / 0.5 \cdot \frac{SNR_{SP}}{20}\sqrt{N_x N_y \cdot 0.16} \\ K=2: L\cdot\frac{4}{5} / 0.5 \cdot \frac{SNR_{SP}}{20}\sqrt{N_x N_y \cdot 0.229} \end{matrix}$$

Thus:

$$\varepsilon(\langle x \text{ or } y\rangle) = \begin{matrix} K=1: L\cdot\frac{40}{3 SNR_{SP}\sqrt{N_x N_y \cdot 0.16}} \\ K=2: L\cdot\frac{32}{SNR_{SP}\sqrt{N_x N_y \cdot 0.229}} \end{matrix}$$

Putting in typical numbers we get $$\varepsilon(\langle x \text{ or } y\rangle) = \begin{matrix} K=1: 6\,\mu m \cdot \frac{40}{3000\sqrt{1600 \cdot 1200 \cdot 0.16}} = 0.144\,nm \\ K=2: 6\,\mu m \cdot \frac{32}{1000\sqrt{1600 \cdot 1200 \cdot 0.229}} = 0.289\,nm \end{matrix}$$

Figure 28:
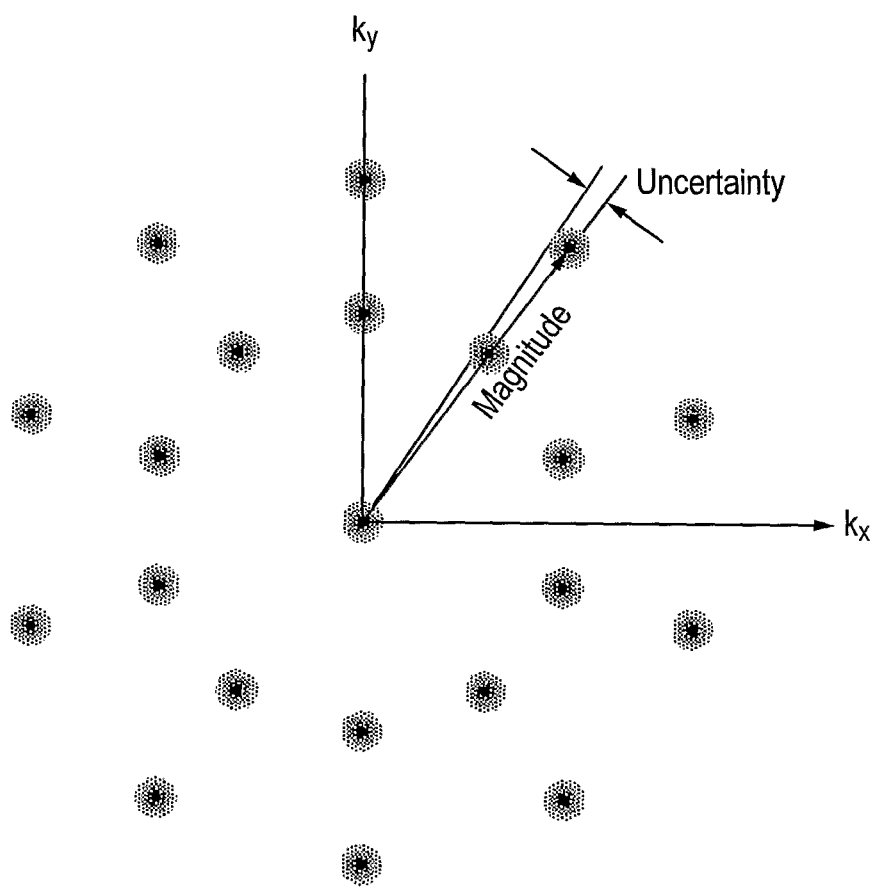
FIG. 28 illustrates the determination of the measurement precision of a rotational measurement in the Fourier domain.

In this case half of the pinholes will be pointing in the wrong direction to give information as to position, so we get an improvement of $\sqrt{10}$ due to using all the spots, or 0.046 and 0.092 nm respectively.

θ: This is the angle about the z-axis, [not to be confused with the previous use of theta in the derivation of the double slit interference pattern]. The value of the rotation can be obtained as a rotation of the Fourier components around the origin. Hence the measurement precision is simply the precision of peak find divided by the magnitude of the spatial frequency, as illustrated in FIG. 28.

So, as before when calculating z, the error in finding the location of the peak divided by the magnitude of the peak is $$\frac{\varepsilon(\theta)}{\theta} = \frac{\varepsilon(z)}{z} = \begin{array}{l} K=1: \dfrac{80}{3000\sqrt{1600 \cdot 1200 \cdot 0.16} \cdot 1200} = 40 \cdot 10^{-9} \\[6pt] K=2: \dfrac{64}{1000\sqrt{1600 \cdot 1200 \cdot 0.229} \cdot 1200} = 80 \cdot 10^{-9} \end{array}$$

Translating into degrees, $40 \cdot 10^{-9}$ radians=40 nrad=2.3 µdegree=8.25 marcsec.

For K=2, angular precision is 16.5 marcsec. Note: θ rotation accuracy is the same number as z accuracy.

Figure 29:
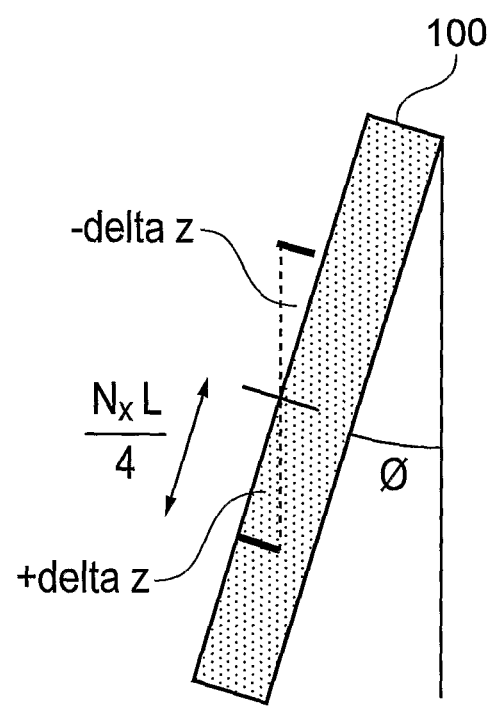
FIG. 29 illustrates the definition of tilt angles $\psi$ and $\phi$ as the rate of change of z with x and y respectively.

Tilt angles, ψ and φ: These angles correspond to a measurement of the rate of change of z with x and y respectively, as illustrated in FIG. 29, in which the tilt of detector 100 is schematically illustrated.

So for one pair of pinholes we have two errors in z measurement for the two halves of the sensor. These two halves are separated by a distance of half the sensor size, which is $$\frac{N_x L}{2} \text{ or } \frac{N_y L}{2},$$

depending on which angle we are measuring. The error in z measurement is that corresponding to a half sensor. Remembering that the error in z measurement for a full sensor is:

$$\frac{\varepsilon(z)}{z} = \begin{array}{l} K=1: \dfrac{80}{3 SNR_{SP}\sqrt{N_x N_y \cdot 0.16} \cdot N_{(x\,or\,y)}} \\[6pt] K=2: \dfrac{64}{SNR_{SP}\sqrt{N_x N_y \cdot 0.229} \cdot N_{(x\,or\,y)}} \end{array}$$

We have that the error for a half sensor is $$\frac{\varepsilon_{half}(z)}{z} = \begin{array}{l} K=1: \dfrac{80}{3 SNR_{SP}\sqrt{\dfrac{N_x N_y}{2} \cdot 0.16} \cdot \dfrac{N_{(x\,or\,y)}}{2}} \\[6pt] K=2: \dfrac{64}{SNR_{SP}\sqrt{\dfrac{N_x N_y}{2} \cdot 0.229} \cdot \dfrac{N_{(x\,or\,y)}}{2}} \end{array}$$

And the error in the angular measurement is given by $$\varepsilon(\phi) = \varepsilon_{half}(z) \div \frac{N_x L}{4}$$

which is (substituting in):

$$\varepsilon(\phi) = \begin{array}{l} K=1: \dfrac{320 z}{3 SNR_{SP}\sqrt{\dfrac{N_x N_y}{2} \cdot 0.16} \cdot \dfrac{N_x^2 L}{2}} \\[6pt] K=2: \dfrac{256 z}{SNR_{SP}\sqrt{\dfrac{N_x N_y}{2} \cdot 0.229} \cdot \dfrac{N_x^2 L}{2}} \end{array}$$

Numerically this is, at 1 inch using typical values, as before:

$$\varepsilon(\phi) = \begin{array}{l} K=1: \dfrac{320 \cdot 25.4 \cdot 10^{-3}\,m}{3000\sqrt{\dfrac{1600 \cdot 1200}{2} \cdot 0.16} \cdot \dfrac{1600^2 \cdot 6 \cdot 10^{-6}\,m}{2}} = 1.25\,\mu rad \\[10pt] K=2: \dfrac{256 \cdot 25.4 \cdot 10^{-3}\,m}{1000\sqrt{\dfrac{1600 \cdot 1200}{2} \cdot 0.229} \cdot \dfrac{1600^2 \cdot 6 \cdot 10^{-6}\,m}{2}} = 1.8\,\mu rad \end{array}$$

These numbers are reduced by averaging over the number of spots in the transform. in this case only half contribute on average (the others are parallel to the axis, so no change with tilt), so the final numbers are $$\frac{1.25\,\mu rad}{\sqrt{10}} = 0.4\,\mu rad = 82\,marc\,sec$$

and $$\frac{1.8\,\mu rad}{\sqrt{10}} = 0.57\,\mu rad = 120\,marc\,sec$$

These are the worst numbers of all, and they are still very good. A caveat concerning the values for z, φ and ψ is that they all degrade in direct proportion with increasing z. This is because they depend critically on the measurement of the relative change in the magnitude of the spatial frequency. A solution for high-value applications is to use more camera chips separated by a larger baseline. The baseline now acts in the same way as the width of the chip in the above calculations, giving an essentially arbitrary improvement in sensitivity.

Optical Element Specification

Figure 30:
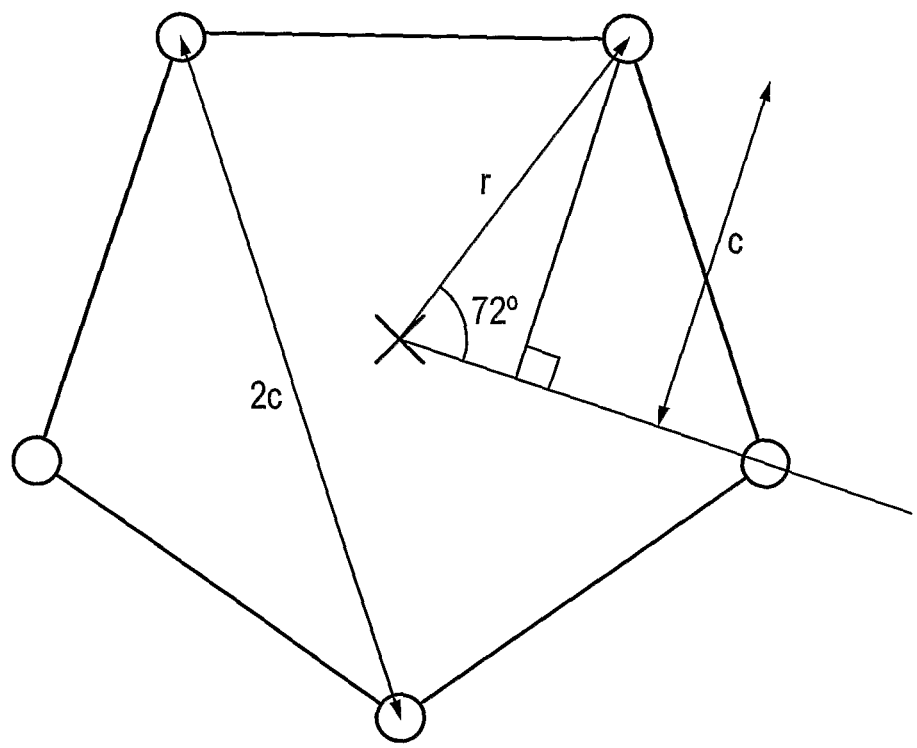
FIG. 30 shows a schematic view of the pentagonal layout of pinholes for an optical element for use in an interference pattern generator in an embodiment of the invention.

The optical element of the preferred embodiments has 5 pinholes disposed in a regular pentagonal array (with 5-fold rotational symmetry, e.g. as shown in FIG. 30) and an associated collimation structure.

Pinhole spacing: The pinhole spacing is determined by the maximum spatial frequency which can be accurately imaged by the detector. The maximum spatial frequency is produced on-axis and hence is given by the normal Young's slit expression:

| Property | Symbol |
|---|---|
| Wavelength | λ |
| Fringe period | $\delta x = \dfrac{\lambda z}{2c}$ |
| Aperture spacing | 2c |
| Distance to sensor | z |
| Spatial frequency | $k_{max} = \dfrac{1}{\delta x}$ |

If the size of the sensor pixel (assumed to be square) is L, then at minimum distance $z_{min}$ we have that $$\delta x = \frac{\lambda z_{min}}{2c} = 2L$$

so that $$2c = \frac{\lambda z_{min}}{2L}$$

From FIG. 30 we see that $r \sin(36°)=c$ so that $$2r\sin(72°) = \frac{\lambda z_{min}}{2L} \therefore r = \frac{\lambda z_{min}}{4L\sin(72°)}$$

For a first detector used in one embodiment of the invention, the pixel spacing is of order 6.8 µm, so that the minimum fringe spacing is 13.6 µm (15 µm used). For a second detector used in another embodiment of the invention, the pixel spacing is 2.2 µm so that the minimum fringe spacing is 4.4 µm (5 µm used). A number of indicative results for standard conditions is shown in Table 3 below:

TABLE 3

| Wavelength, nm | zmin, mm | L, µm | 2c, mm | r, mm |
|---|---|---|---|---|
| 532 | 25 | 7.5 | 0.887 | 0.466 |
| 532 | 50 | 7.5 | 1.773 | 0.932 |
| 532 | 100 | 7.5 | 3.547 | 1.865 |
| 532 | 25 | 2.5 | 2.660 | 1.398 |
| 532 | 50 | 2.5 | 5.320 | 2.797 |
| 532 | 100 | 2.5 | 10.640 | 5.594 |
| 710 | 25 | 2.5 | 3.550 | 1.866 |
| 710 | 50 | 2.5 | 7.100 | 3.733 |
| 710 | 100 | 2.5 | 14.200 | 7.465 |
| 860 | 25 | 2.5 | 4.300 | 2.261 |
| 860 | 50 | 2.5 | 8.600 | 4.521 |
| 860 | 100 | 2.5 | 17.200 | 9.043 |

It is apparent that the size of the optical element for larger spacing with smaller camera pixels increases quite rapidly. Although the optical element can be produced by e-beam lithography, larger optical elements are preferably produced by other fabrication procedures, as discussed above.

Figure 31:
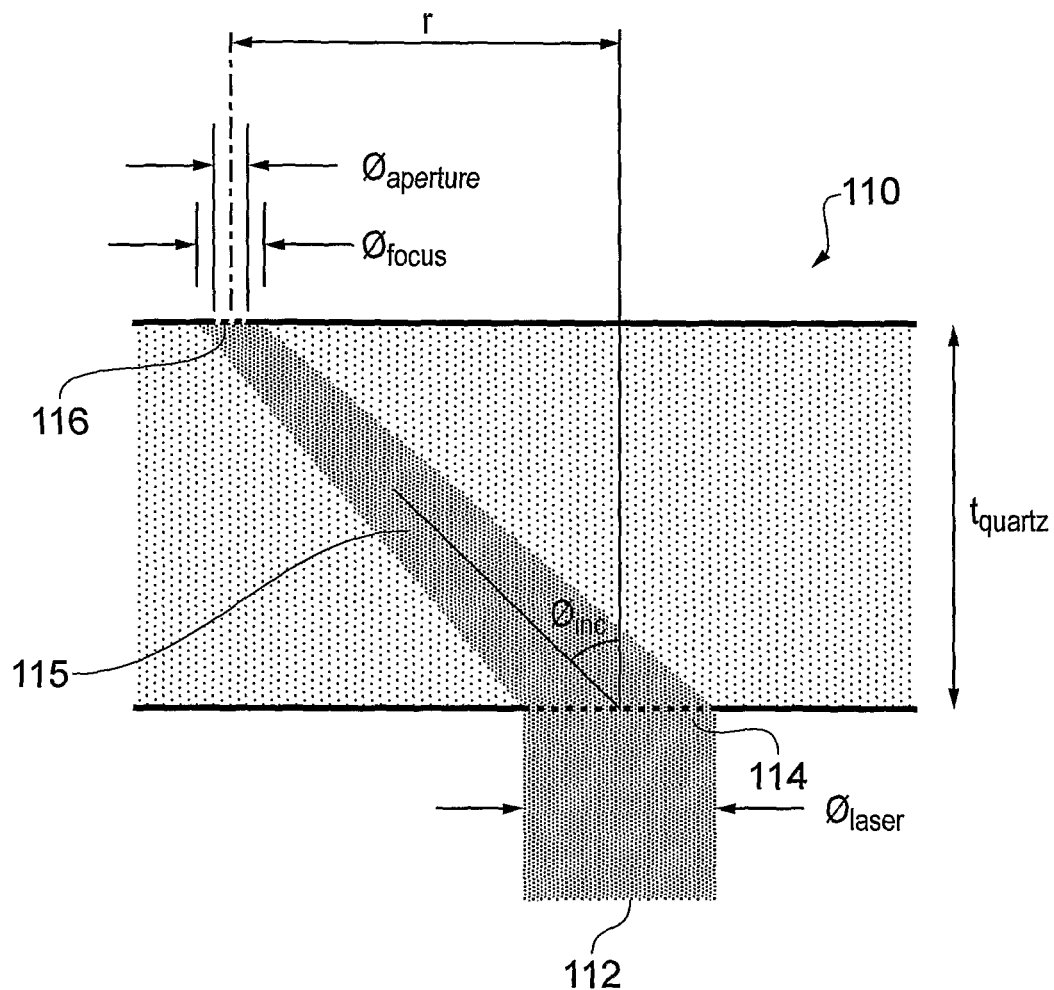
FIG. 31 shows a schematic cross sectional partial view through an optical elements for use with an embodiment of the invention, illustrating the path of the input beam through a holographic collimator to the aperture.

FIG. 31 shows a schematic cross sectional partial view through an optical element 110 formed on a quartz substrate for use with an embodiment of the invention, illustrating the path of the input beam 112 through a holographic collimator 114 to the aperture 116. It is seen from FIG. 31 that as the radius, r, increases, so does $\theta_{inc}$, potentially increasing above the angle at which the light is totally internally reflected. Although there is a grating present at the aperture to scatter the light incident on the aperture into the forward direction, the use of a very large value of $\theta_{inc}$ is possibly still a problem. It is also clear that if the angle is very large, the focused spot will be very elliptical, again reducing the power exiting the aperture.

The value of $\theta_{inc}$ such that the beam is just totally internally reflected is given by Snell's law such that $n_{quartz} \sin(\theta_{inc}) \geq 1 = n_{air} \sin(\theta_{exiting})$, where $n_{quartz}$ is the refractive index of quartz, $n_{air}$ is the refractive index of air (=1), and $\theta_{exiting}$ is the angle of the light leaving the quartz. Total internal reflection occurs when this angle becomes imaginary ($\sin(\theta_{exiting}) > 1$). Thus, Table 4 shows the maximum values for $\theta_{inc}$ in a few cases.

TABLE 4

| Wavelength (nm) | $n_{quartz}$ (approx) | $\theta_{inc}$ (degrees) |
|---|---|---|
| 532 | 1.46071 | 43.20404646 |
| 710 | 1.45515 | 43.41000523 |
| 860 | 1.45247 | 43.5100958 |

Hence, if we limit the incident angle to 40°, we obtain an expression for the minimum quartz thickness. From FIG. 31 we see that $r = t_{quartz} \tan(\theta_{inc})$, so that $$t_{quartz} = \frac{r}{\tan(\theta_{inc})}.$$

Putting this into Table 3 (indicative values) we obtain Table 5.

TABLE 5

| Wavelength, nm | zmin, mm | L, µm | 2c, mm | r, mm | tquartz, mm |
|---|---|---|---|---|---|
| 532 | 25 | 7.5 | 0.887 | 0.466 | 0.556 |
| 532 | 50 | 7.5 | 1.773 | 0.932 | 1.111 |
| 532 | 100 | 7.5 | 3.547 | 1.865 | 2.222 |
| 532 | 25 | 2.5 | 2.660 | 1.398 | 1.667 |
| 532 | 50 | 2.5 | 5.320 | 2.797 | 3.333 |
| 532 | 100 | 2.5 | 10.640 | 5.594 | 6.666 |
| 710 | 25 | 2.5 | 3.550 | 1.866 | 2.224 |
| 710 | 50 | 2.5 | 7.100 | 3.733 | 4.448 |
| 710 | 100 | 2.5 | 14.200 | 7.465 | 8.897 |
| 860 | 25 | 2.5 | 4.300 | 2.261 | 2.694 |
| 860 | 50 | 2.5 | 8.600 | 4.521 | 5.388 |
| 860 | 100 | 2.5 | 17.200 | 9.043 | 10.777 |

It is interesting to note that these values are comparable to that of a conventional mask plate. A normal (4 or 5 inch) plate is 0.09 inch thick (2.3±0.1 mm), with a tolerance on thickness (variation across the plate) of ≤5 µm. The blocks used for nanoimprint lithography are a quarter inch thick. A typical supplier suggests 6.35 mm ±0.1 mm with no defined parallelism tolerance.

The two options for manufacture of the optical element are therefore, either to use a monolithic block (this is the presently preferred method) with measurement of thickness and adaptive patterns, or else to use separate hologram and aperture plate, with alignment individually between the two.

Aperture: A hologram can be used to focus the input light onto all five apertures at once. The resolution of the focal spot is given by the usual Abbe limit (although the tilted incidence angle will make the spot somewhat elliptical; another good reason to control $\theta_{inc}$). It is strongly preferred in the present invention that the position of the light transmitted by the aperture be well defined. Consequently, the aperture is arranged to be somewhat smaller than the focal spot of the hologram. (i.e. $\emptyset_{aperture} < \emptyset_{focus}$ in FIG. 31). In this way the pinhole is located by the sharp metallic edges of the metal film, not the fuzzy, blurred Gaussian spot produced by the hologram.

The aperture serves three functions:

1 To define the position of the light source with high accuracy.
2 To scatter the light over a large enough range of angles to fill the volume of space in which the detector will move relative to the generator.
3 To scatter the light such that a substantial fraction of the light from the apertures is in the forward direction.

The first requirement can be achieved by the use of a high resolution, high accuracy fabrication process. The location of the apertures is limited by the accuracy of the lithography tool used (about 10 nm for a VB6 UHR EWF) and by the precision of the etch. Results on a similar process used for the definition of aperture near-field optical microscope AFM probes has demonstrated a reproducibility of approximately ±5 nm in the diameter of 100 nm apertures. The reproducibility of the large apertures used in some embodiments of the invention can be better than that of subwavelength apertures defined in thick metal.

Figure 32:
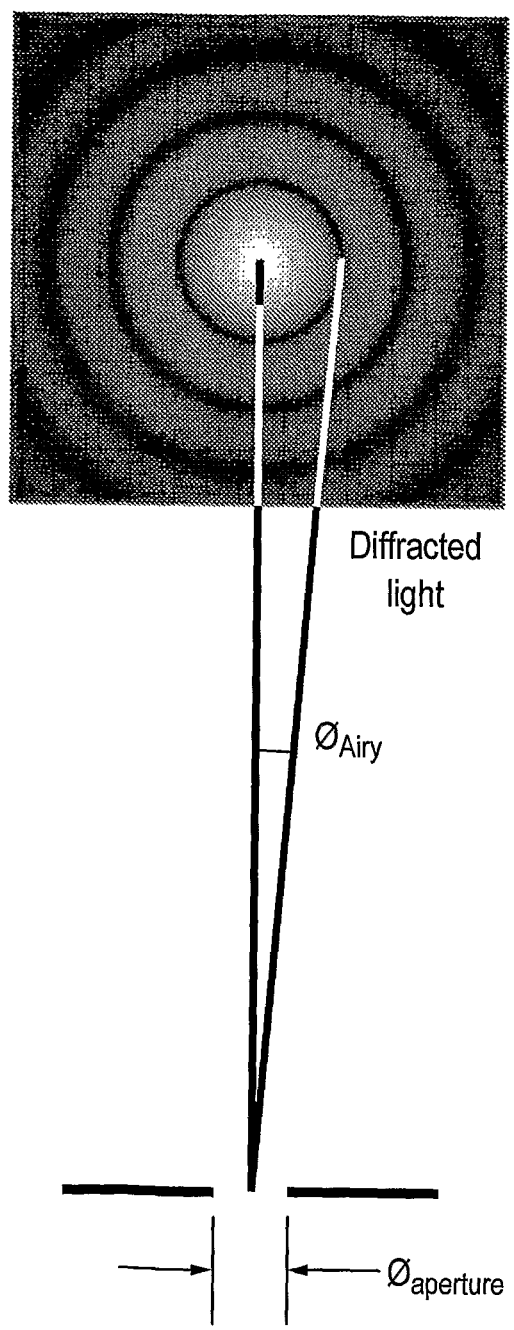
FIG. 32 illustrates the Airy disk resulting from diffraction by a circular aperture.

The second requirement is achieved by making the apertures have a small diameter. If light is passed through a circular pinhole of diameter $d_{aperture}$, then the light output will be spread into a range of angles, the "Airy disk", such that $$\sin(\theta_{Airy}) = 1.22 \frac{\lambda}{\phi_{aperture}}$$

to the first minimum in the pattern. This is illustrated in FIG. 32. If we require that the light exiting the aperture 116 should fill a volume within ±45° of the optical axis, this implies that $$\phi_{aperture} = 1.22 \frac{\lambda}{\sin(\theta_{Airy})} = 1.22 \frac{\lambda}{\sin(45°)} = 1.73\lambda.$$

Alternatively, if we require that the optical intensity should be at the half maximum at 45° to the axis we have that $$\phi_{aperture} = 0.5145 \frac{\lambda}{\sin(\theta_{Airy})} = 0.5145 \frac{\lambda}{\sin(45°)} = 0.728\lambda$$

Thus for the three indicative wavelengths, we obtain Table 6:

TABLE 6

| Lambda | $\phi_{aperture}$ {45° = zero intensity} | $\phi_{aperture}$ {45° = half intensity} |
|---|---|---|
| 532 nm | 917 nm | 387 nm |
| 710 nm | 1.22 μm | 517 nm |
| 860 nm | 1.48 μm | 626 nm |

The third function of the aperture is to make sure that a significant fraction of the light is scattered into the forward direction. For this to occur we need the incident wave to impinge on a structure which will impart the appropriate phase shift across the aperture so as to turn the beam into the correct direction. This could be achieved by the use of a very small prism (not readily fabricated), a diffraction grating or a kinoform. The simplest case (since the aperture is already a hole in a metallic sheet) is to use a metallic diffraction grating. The construction for calculation of the grating period is shown in FIG. 33, indicating the path of the beam 115 between the hologram 114 and the aperture 116.

Figure 33:
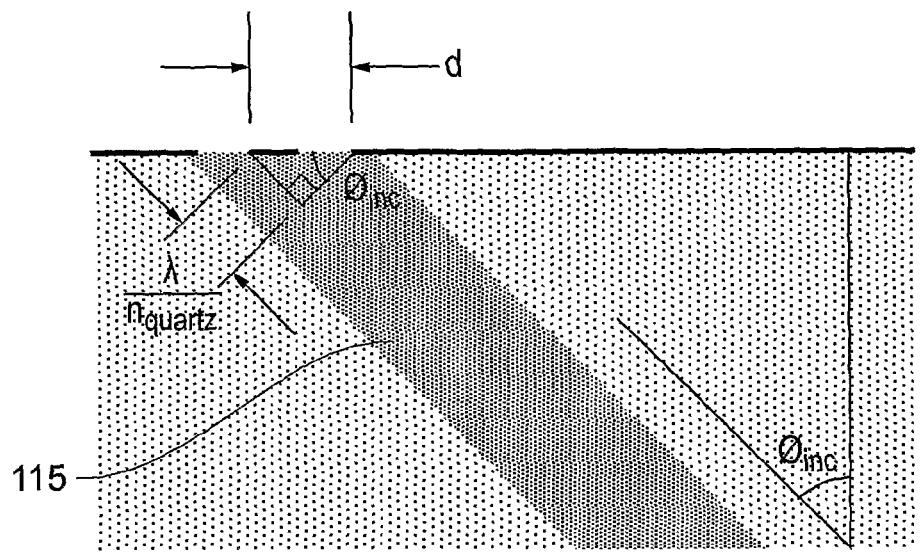
FIG. 33 shows a construction for the calculation of the grating period for use at an optical element used in the generator in an embodiment of the invention.

From FIG. 33, we see that $$d\sin(\theta_{inc}) = \frac{\lambda}{n_{quartz}}$$

so that $$d = \frac{\lambda}{\sin(\theta_{inc}) \cdot n_{quartz}}.$$

Figure 34:
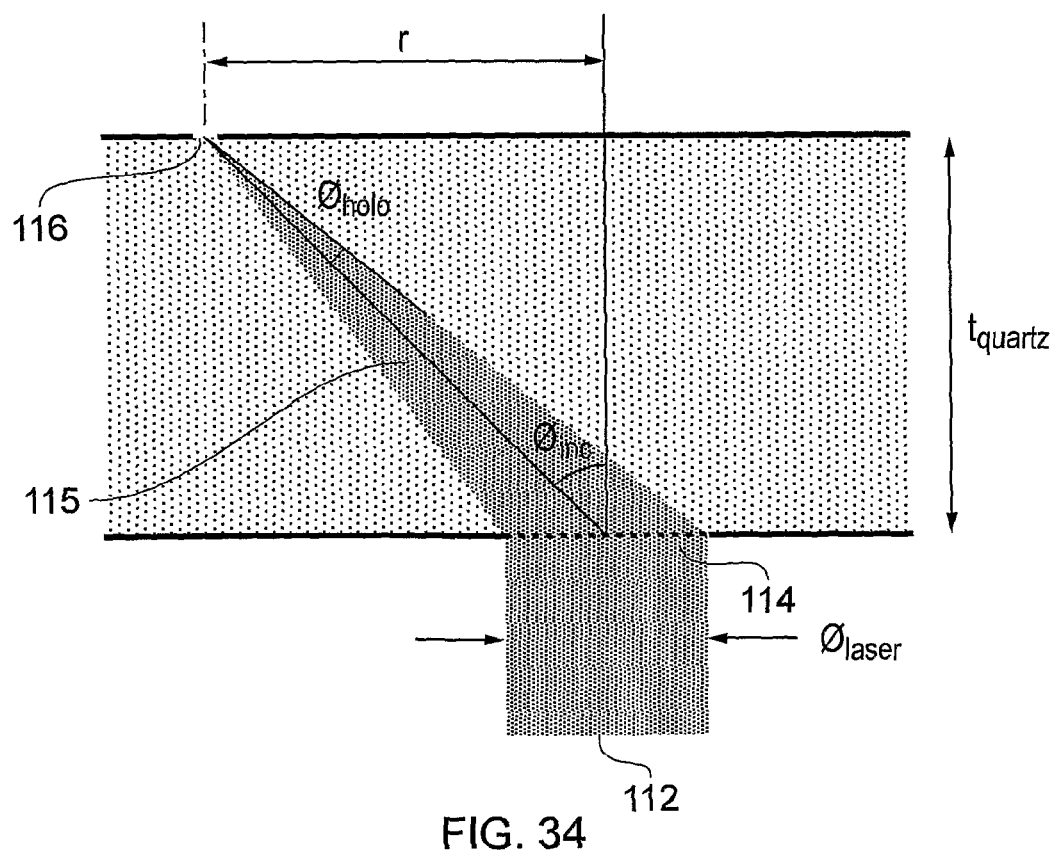
FIG. 34 shows a construction to determine numerical aperture for use in designing an optical elements used in the generator in an embodiment of the invention.

Hologram: The hologram is calculated in the usual way by adding up the phases from each aperture referred to the position at the hologram (ray tracing). The size of the focal spot is determined in the normal way for the resolution of an optical microscope. Thus we can estimate the spot size from the angle subtended by the hologram as seen from the aperture. From FIG. 34, we see that $$t_{quartz}\tan(\theta_{inc}) = r$$

$$t_{quartz}\tan(\theta_{inc} + \theta_{holo}) = r + \frac{\phi_{laser}}{2}$$

and if we make the assumption that $\theta_{holo}$ is not too large, we have that $$t_{quartz}\tan(\theta_{inc} + \theta_{holo}) = r + \frac{\phi_{laser}}{2} \approx t_{quartz}\left(\tan(\theta_{inc}) + \frac{d\tan(\theta_{inc})}{d\theta_{inc}}\theta_{holo}\right) =$$

$$t_{quartz}(\tan(\theta_{inc}) + \sec^2(\theta_{inc})\theta_{holo}) = r + t_{quartz}\sec^2(\theta_{inc})\theta_{holo}$$

hence $t_{quartz}\sec^2(\theta_{inc})\theta_{holo} \approx \frac{\phi_{laser}}{2}$ so $\theta_{holo} \approx \frac{\phi_{laser}}{2t_{quartz}\sec^2(\theta_{inc})}$ And hence we have that $$NA = \sin(\theta_{holo}) \approx \sin\left(\frac{\phi_{laser}}{2t_{quartz}\sec^2(\theta_{inc})}\right) \approx \frac{\phi_{laser}}{2t_{quartz}\sec^2(\theta_{inc})}.$$

The size of the spot at the aperture is therefore given by $$\phi_{\perp focus} = \frac{\lambda}{2NA \cdot n_{quartz}} \approx \frac{\lambda \cdot 2t_{quartz}\sec^2(\theta_{inc})}{2\phi_{laser} \cdot n_{quartz}} = \frac{\lambda \cdot t_{quartz}\sec^2(\theta_{inc})}{\phi_{laser} \cdot n_{quartz}}$$

where $\phi_{\perp focus}$ is the focal spot size in the direction perpendicular to the page in FIG. 31. The dimension indicated on the diagram as $\phi_{focus}$ is a little larger than this, since the beam is incident at angle $\theta_{inc}$.

The size of the focal spot for a given optical element thickness is controlled by $\phi_{laser}$ which is varied either by expansion of the beam or else by truncating the area of the hologram. The latter wastes the light which is not incident on the hologram. For a diode laser, beam expansion is readily achieved by using the natural divergence of the light from the laser facet: the hologram is simply recalculated to take account of the curvature of the incident wavefronts.

The hologram is preferably a kinoform [see "The Kinoform: A New Wavefront Reconstruction Device" L. B. Lesem, P. M. Hirsch, J. A. Jordan, Jr. *IBM J. Res. Dev.* 13 (2) p. 150 (1969)], formed by etching the binary hologram pattern half a wavelength deep into the quartz. This would give a factor of 4 improvement in throughput for not much more fabrication (and is compatible with nano imprint lithography). Multilevel kinoforms are harder to make, but can diffract all of the light into the focal spots.

Wavelength sensitivity: The hologram used in the preferred embodiments of the invention is a diffractive optic. As a result the position of the focal spot will change as the wavelength changes. If we assume that the system is perfectly aligned at a wavelength of $\lambda_0$, then a change in wavelength of $\delta\lambda$ will shift the focal spot by a distance of $$\frac{\phi_{\perp focus}}{2},$$

resulting in extinction of the output from that spot. The shift in position is caused by a change in deflection angle $\delta\theta_{inc}$. If we assume that this shift corresponds to a normal diffraction grating action on the part of the hologram, ascribing an effective grating period $d_{eff}$ to the hologram, we have that $$d_{eff}\sin(\theta_{inc}) = \lambda_0 \therefore \frac{d\lambda_0}{d\theta_{inc}} = d_{eff}\cos(\theta_{inc}) = \frac{\lambda_0\cos(\theta_{inc})}{\sin(\theta_{inc})}$$

and the change in $\theta_{inc}$ is given by $$\delta\theta_{inc} = \frac{\phi_{\perp focus}}{2} \div \frac{r}{\sin(\theta_{inc})} = \frac{\lambda_0 \cdot t_{quartz}\sec^2(\theta_{inc})\sin(\theta_{inc})}{2r\phi_{laser} \cdot n_{quartz}}$$

Hence $$\delta\lambda_0 \approx \frac{d\lambda_0}{d\theta_{inc}} \cdot \delta\theta_{inc} =$$

$$\frac{\lambda_0\cos(\theta_{inc})}{\sin(\theta_{inc})} \cdot \frac{\lambda_0 \cdot t_{quartz}\sec^2(\theta_{inc})\sin(\theta_{inc})}{2r\phi_{laser} \cdot n_{quartz}} = \lambda_0^2 \frac{t_{quartz}\sec(\theta_{inc})}{2r\phi_{laser} \cdot n_{quartz}}$$

and $t_{quartz}\tan(\theta_{inc}) = r$ so $$\frac{\delta\lambda_0}{\lambda_0} \approx \lambda_0 \frac{t_{quartz}\sec(\theta_{inc})}{2t_{quartz}\tan(\theta_{inc})\phi_{laser} \cdot n_{quartz}} = \frac{\lambda_0}{2\sin(\theta_{inc})\phi_{laser} \cdot n_{quartz}}$$

If we now limit the size of the spot to $\phi_{\perp focus} = 2\phi_{aperture}$ and put in the numbers as before, solving for $$\phi_{laser} \text{ and } \frac{\delta\lambda_0}{\lambda_0}$$

we obtain Table 7.

TABLE 7

| $\lambda_0$, nm | $Z_{min}$, mm | L, μm | 2c, mm | r, mm | $t_{quartz}$, mm | $\emptyset_{aperture}$, μm | $\emptyset_{laser}$, mm | $\delta\lambda_0/\lambda_0$ |
|---|---|---|---|---|---|---|---|---|
| 532 | 25 | 7.5 | 0.887 | 0.466 | 0.556 | 0.917 | 0.188 | $1.51 \cdot 10^{-3}$ |
| 532 | 50 | 7.5 | 1.773 | 0.932 | 1.111 | 0.917 | 0.376 | $7.53 \cdot 10^{-4}$ |
| 532 | 100 | 7.5 | 3.547 | 1.865 | 2.222 | 0.917 | 0.752 | $3.77 \cdot 10^{-4}$ |
| 532 | 25 | 2.5 | 2.660 | 1.398 | 1.667 | 0.917 | 0.564 | $5.02 \cdot 10^{-4}$ |
| 532 | 50 | 2.5 | 5.320 | 2.797 | 3.333 | 0.917 | 1.128 | $2.51 \cdot 10^{-4}$ |
| 532 | 100 | 2.5 | 10.640 | 5.594 | 6.666 | 0.917 | 2.256 | $1.26 \cdot 10^{-4}$ |
| 710 | 25 | 2.5 | 3.550 | 1.866 | 2.224 | 1.22 | 0.758 | $5.01 \cdot 10^{-4}$ |
| 710 | 50 | 2.5 | 7.100 | 3.733 | 4.448 | 1.22 | 1.516 | $2.50 \cdot 10^{-4}$ |
| 710 | 100 | 2.5 | 14.200 | 7.465 | 8.897 | 1.22 | 3.032 | $1.25 \cdot 10^{-4}$ |
| 860 | 25 | 2.5 | 4.300 | 2.261 | 2.694 | 1.48 | 0.918 | $5.02 \cdot 10^{-4}$ |
| 860 | 50 | 2.5 | 8.600 | 4.521 | 5.388 | 1.48 | 1.837 | $2.51 \cdot 10^{-4}$ |
| 860 | 100 | 2.5 | 17.200 | 9.043 | 10.777 | 1.48 | 3.673 | $1.25 \cdot 10^{-4}$ |

As can be seen, longer range optics require the use of more expanded laser beams. They also place increasingly stringent requirements on the wavelength of the laser.

In the case of a YLF laser the longitudinal mode spacing will be of order ¼ nm, so that if $\delta\lambda_0/\lambda_0$ is less than $5 \cdot 10^{-4}$ the optic itself will begin to select only a single mode from the input beam. This renders the use of wavelength measurement important since we can no longer rely on an average wavelength over all the modes; the laser becomes strictly monochromatic, with a wavelength uncertainty of about ±2 parts in ten thousand. In the worst case, temperature induced shifts in mode position might result in no light throughput at all. This can be fixed by reducing the expansion of the beam, at the expense of light throughput.

In the case of a single-mode diode laser, the situation is better. The beam expansion is obtained trivially by moving the uncollimated laser output closer to or further away from the hologram. In operation the fact that the optical element only passes light if it is close to a particular wavelength can be used as a simple method of controlling the wavelength of the diode laser—it is necessary only to optimise throughput to be within 200 ppm. Any wavelength measurement system (etalon) then has a narrow range of correction which must be applied.

* * *

The preferred embodiments have been described by way of example. Modifications of these embodiments, further embodiments and modifications thereof will be apparent to the skilled person on reading this disclosure and as such are within the scope of the present invention.

The invention claimed is:

1. A measurement system comprising:
   an electromagnetic radiation diffraction pattern generator for generating a diffraction pattern including intensity maxima and intensity minima, wherein the diffraction pattern generator includes an arrangement of light-transmitting apertures for the transmission and diffraction of light to generate the diffraction pattern; and
   an electromagnetic radiation detector, operable to detect at least a part of the diffraction pattern produced by said generator, the detector having an array of detection elements arranged to detect a location of each of a plurality of the intensity maxima and/or intensity minima of the diffraction pattern substantially simultaneously;
   wherein the electromagnetic radiation diffraction pattern generator comprises a laser attached to a pinhole array;
   wherein the arrangement of light-transmitting apertures comprises five pinholes arranged on the vertices of a regular pentagon or a ring of nineteen pinholes;
   wherein the detected locations of the plurality of the intensity maxima and/or intensity minima are substantially translationally aperiodic;
   wherein the diffraction pattern is a two dimensional diffraction pattern;
   wherein the detection elements are arranged in a two dimensional array at the detector;
   wherein the maxima of the diffraction pattern are spaced apart at a pitch equal to at least twice the pitch of the detection elements;
   wherein the detector intercepts at least 10 maxima and/or minima in a single detection event;
   wherein the detector has at least 10,000 pixels; and
   wherein the system is capable of determining a physical property of the system, or a change in a physical property of the system, based on the detected locations of the plurality of the intensity maxima and/or intensity minima.

2. The measurement system according to claim 1, further comprising an object whose position is to be measured, wherein the object whose position is to be measured is the physical property to be determined by the system.

3. The measurement system according to claim 2 wherein the object whose position is to be determined has a fixed spatial relationship with either:
(i) the electromagnetic radiation diffraction pattern generator, or
(ii) the electromagnetic radiation detector.

4. The measurement system according to claim 3 wherein in use, movement of the object from a first to a second position causes a change of the diffraction pattern captured at the detector, and
wherein the object is movable by:
(i) a movement corresponding to translation along at least one of three orthogonal translational axes; or
(ii) a movement corresponding to rotation about at least one of three orthogonal rotational axes,
said movement of the object, or any combination of said movements providing a variation in the diffraction pattern or the part of the diffraction pattern detected by the detector.

5. The measurement system according to claim 1, wherein the diffraction pattern generator comprises a light source, the electromagnetic radiation provided by the diffraction pattern generator being spatially coherent.

6. The measurement system according to claim 1, wherein the system further comprises a second detector, the second detector being for detecting a different part of the diffraction pattern than the first detector.

7. The measurement system according to claim 6 wherein the first detector and the second detector are parts of a single main detector.

8. The measurement system according to claim 1, wherein the system further comprises a second electromagnetic radiation detector, the first and second detectors each being operable to detect a respective part of the diffraction pattern produced by said generator, and wherein the refractive index of the respective optical paths between the generator and the first and second detectors is deliberately made to be different by a known amount, the patterns detected by the first and second detectors being usable to determine the wavelength of the electromagnetic radiation.

9. The measurement system according to claim 1, further comprising path modification means to provide at least two different path lengths for the electromagnetic radiation from the generator to the detector, so as to provide at least two diffraction patterns at the detector, corresponding to the at least two different path lengths.

10. The measurement system according to claim 9, wherein the path modification means provides a difference in reflection of the electromagnetic radiation along the respective path lengths.

11. The measurement system according to claim 10 wherein an etalon is provided between the generator and the detector, the different path length being provided in use by different numbers of transits of the electromagnetic radiation across the etalon before reaching the detector.

12. A position determination apparatus comprising a measurement system comprising:
an electromagnetic radiation diffraction pattern generator for generating an diffraction pattern including intensity maxima and intensity minima, wherein the diffraction pattern generator includes an arrangement of light-transmitting apertures for the transmission and diffraction of light to generate the diffraction pattern; and
an electromagnetic radiation detector, operable to detect at least a part of the diffraction pattern produced by said generator, the detector having an array of detection elements arranged to detect a location of each of a plurality of the intensity maxima and/or intensity minima of the diffraction pattern substantially simultaneously;
wherein the electromagnetic radiation diffraction pattern generator comprises a laser attached to a pinhole array;
wherein the arrangement of light-transmitting apertures comprises five pinholes arranged on the vertices of a regular pentagon or a ring of nineteen pinholes;
wherein the detected locations of the plurality of the intensity maxima and/or intensity minima are substantially translationally aperiodic diffraction pattern;
wherein the diffraction pattern is a two dimensional diffraction pattern;
wherein the detection elements are arranged in a two dimensional array at the detector;
wherein the maxima of the diffraction pattern are spaced apart at a pitch equal to at least twice the pitch of the detection elements;
wherein the detector intercepts at least 10 maxima and/or minima in a single detection event;
wherein the detector has at least 10,000 pixels; and
wherein and the system is capable of determining a physical property of the system, or a change in a physical property of the system, based on the detected locations of the plurality of the intensity maxima and/or intensity minima.

13. A wavelength determination apparatus comprising a measurement system comprising:
an electromagnetic radiation diffraction pattern generator for generating an diffraction pattern including intensity maxima and intensity minima, wherein the diffraction pattern generator includes an arrangement of light-transmitting apertures for the transmission and diffraction of light to generate the diffraction pattern; and
an electromagnetic radiation detector, operable to detect at least a part of the diffraction pattern produced by said generator, the detector having an array of detection elements arranged to detect a location of a plurality of the intensity maxima and/or intensity minima of the diffraction pattern substantially simultaneously,
wherein the electromagnetic radiation diffraction pattern generator comprises a laser attached to a pinhole array;
wherein the arrangement of light-transmitting apertures comprises five pinholes arranged on the vertices of a regular pentagon or a ring of nineteen pinholes;
wherein the detected locations of the plurality of the intensity maxima and/or intensity minima are substantially translationally aperiodic;
wherein the diffraction pattern is a two dimensional diffraction pattern;
wherein the detection elements are arranged in a two dimensional array at the detector;
wherein the maxima of the diffraction pattern are spaced apart at a pitch equal to at least twice the pitch of the detection elements;
wherein the detector intercepts at least 10 maxima and/or minima in a single detection event;
wherein the detector has at least 10,000 pixels; and
wherein the system is capable of determining a physical property of the system, or a change in a physical property of the system, based on the detected locations of the plurality of the intensity maxima and/or intensity minima.

14. A refractive index determination apparatus comprising a measurement system comprising:
- an electromagnetic radiation diffraction pattern generator for generating an diffraction pattern including intensity maxima and intensity minima, wherein the diffraction pattern generator includes an arrangement of light-transmitting apertures for the transmission and diffraction of light to generate the diffraction pattern; and
- an electromagnetic radiation detector, operable to detect at least a part of the diffraction pattern produced by said generator, the detector having an array of detection elements arranged to detect a location of each of a plurality of the intensity maxima and/or intensity minima of the diffraction pattern substantially simultaneously,
- wherein the electromagnetic radiation diffraction pattern generator comprises a laser attached to a pinhole array;
- wherein the arrangement of light-transmitting apertures comprises five pinholes arranged on the vertices of a regular pentagon or a ring of nineteen pinholes;
- wherein the detected locations of the plurality of the intensity maxima and/or intensity minima are substantially translationally aperiodic;
- wherein the diffraction pattern is a two dimensional diffraction pattern;
- wherein the detection elements are arranged in a two dimensional array at the detector;
- wherein the maxima of the diffraction pattern are spaced apart at a pitch equal to at least twice the pitch of the detection elements;
- wherein the detector intercepts at least 10 maxima and/or minima in a single detection event;
- wherein the detector has at least 10,000 pixels; and
- wherein the system is capable of determining a physical property of the system, or a change in a physical property of the system, based on the detected locations of the plurality of the intensity maxima and/or intensity minima.

* * * * *